(12) United States Patent
Yamaki et al.

(10) Patent No.: US 7,595,184 B2
(45) Date of Patent: Sep. 29, 2009

(54) NITRILE HYDRATASE VARIANT

(75) Inventors: Toshifumi Yamaki, Mobara (JP); Shinichi Banba, Mobara (JP); Kaori Matoishi, Mobara (JP); Kiyoshi Ito, Sodegaura (JP); Hideki Kobayashi, Mobara (JP); Eishi Tanaka, Sodegaura (JP); Toshihiro Oikawa, Mobara (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 248 days.

(21) Appl. No.: 10/539,560

(22) PCT Filed: Dec. 15, 2003

(86) PCT No.: PCT/JP03/16014

§ 371 (c)(1),
(2), (4) Date: Jun. 17, 2005

(87) PCT Pub. No.: WO2004/056990

PCT Pub. Date: Jul. 8, 2004

(65) Prior Publication Data

US 2007/0009985 A1 Jan. 11, 2007

(30) Foreign Application Priority Data

Dec. 19, 2002 (JP) .............................. 2002-368360
Nov. 10, 2003 (JP) .............................. 2003-379280

(51) Int. Cl.
*C12N 9/88* (2006.01)
*C12N 5/10* (2006.01)
*C12N 1/21* (2006.01)
*C07K 14/00* (2006.01)
*C12P 21/00* (2006.01)
*C12N 15/00* (2006.01)
*C12Q 1/527* (2006.01)
*C07H 21/00* (2006.01)

(52) U.S. Cl. .................. 435/232; 435/69.1; 435/320.1; 435/325; 435/252.3; 435/4; 530/350; 536/23.2

(58) Field of Classification Search .................. 435/232, 435/69.1, 320.1, 252.3, 350, 4; 530/350; 536/23.2
See application file for complete search history.

(56) References Cited

U.S. PATENT DOCUMENTS 5,334,519 A 8/1994 Yamada et al.
5,910,432 A 6/1999 Ito et al.

6,730,508 B1 5/2004 Ito et al.

FOREIGN PATENT DOCUMENTS

| EP | 0 445 646 A2 | 9/1991 |
| EP | 0 790 310 A2 | 8/1997 |
| JP | 02-000470 A | 1/1990 |
| JP | 04-211379 A | 8/1992 |
| JP | 08-056684 A | 3/1996 |
| JP | 09-275978 A | 10/1997 |
| JP | 11-253168 A | 9/1999 |

OTHER PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Kobayashi et al., "Cloning, nucleotide sequence and expression in *Escherichia coli* of two cobalt-containing nitrile hydratase genes from *Rhodococcus rhodochrous* J1," *Biochim et Biophysica Acta*, Dec. 2, 1991, pp. 23-33, vol. 1129(1), Elsevier Science Publishers B.V.
Huang et al., "Crystal structure of nitrile hydratase reveals a novel iron centre in a novel fold," *Structure*, 1997, pp. 691-699, vol. 5, No. 5.
"Novel non-heme iron center of nitrile hydratase with a claw setting of oxygen atoms," *Nature Structural Biology*, May 1998, pp. 347-351, vol. 5, No. 5.
Miyanaga et al., "Crystal Structure of Cobalt-Containing Nitrite Hydratase," *Biochemical and Biophysical Research Communications*, 2001, pp. 1169-1174, vol. 288(5), Academic Press.
Supplementary European Search Report dated Feb. 20, 2008.
Hashimoto et al., "Site-Directed Mutagenesis for Cysteine Residues of Cobalt-Containing Nitrile Hydratase", Journal of Inorganic Biochemistry, vol. 91, No. 1, pp. 70-77, Jul. 25, 2002.
Yamaki et al., "Cloning and Sequencing of Nitrile Hydratase Gene from *Pseudonocardia Thermophila* JCM3095", Journal of Fermentation and Bioengineering, vol. 83, No. 5, pp. 474-477, 1997.

* cited by examiner

*Primary Examiner*—Delia M Ramirez
(74) *Attorney, Agent, or Firm*—Buchanan Ingersoll & Rooney PC

(57) ABSTRACT

The amino acid sequence of a mutant which is obtained by introducing a novel mutation into a *Pseudonocardia thermophila* JCM3095-derived nitrile hydratase consisting of two types of heterogeneous subunits, and the base sequence of the gene are provided. The nitrile hydratase is modified by specifying the region to be modified in the stereostructure/amino acid sequence of the nitrile hydratase, and applying alteration such as substitution, insertion, deletion or the like, to the amino acids in the amino acid sequence which are corresponding to the amino acid residues forming the region. Also provided is a method for modifying an enzyme having a nitrile hydratase activity.

12 Claims, 2 Drawing Sheets

US 7,595,184 B2

SEQUENCE LISTING

<160> NUMBER OF SEQ ID NOS: 142

<210> SEQ ID NO 1
<211> LENGTH: 205
<212> TYPE: PRT
<213> ORGANISM: Pseudonocardia thermophila

<400> SEQUENCE: 1

```
Met Thr Glu Asn Ile Leu Arg Lys Ser Asp Glu Glu Ile Gln Lys Glu
  1               5                  10                  15

Ile Thr Ala Arg Val Lys Ala Leu Glu Ser Met Leu Ile Glu Gln Gly
             20                  25                  30

Ile Leu Thr Thr Ser Met Ile Asp Arg Met Ala Glu Ile Tyr Glu Asn
         35                  40                  45

Glu Val Gly Pro His Leu Gly Ala Lys Val Val Val Lys Ala Trp Thr
     50                  55                  60

Asp Pro Glu Phe Lys Lys Arg Leu Leu Ala Asp Gly Thr Glu Ala Cys
 65                  70                  75                  80

Lys Glu Leu Gly Ile Gly Gly Leu Gln Gly Glu Asp Met Met Trp Val
                 85                  90                  95

Glu Asn Thr Asp Glu Val His His Val Val Cys Thr Leu Cys Ser
            100                 105                 110

Cys Tyr Pro Trp Pro Val Leu Gly Leu Pro Pro Asn Trp Phe Lys Glu
        115                 120                 125
```

```
Pro Gln Tyr Arg Ser Arg Val Val Arg Glu Pro Arg Gln Leu Leu Lys
        130                 135                 140

Glu Glu Phe Gly Phe Glu Val Pro Pro Ser Lys Glu Ile Lys Val Trp
145                 150                 155                 160

Asp Ser Ser Ser Glu Met Arg Phe Val Val Leu Pro Gln Arg Pro Ala
                165                 170                 175

Gly Thr Asp Gly Trp Ser Glu Glu Leu Ala Thr Leu Val Thr Arg
            180                 185                 190

Glu Ser Met Ile Gly Val Glu Pro Ala Lys Ala Val Ala
        195                 200                 205

<210> SEQ ID NO 2
<211> LENGTH: 233
<212> TYPE: PRT
<213> ORGANISM: Pseudonocardia thermophila

<400> SEQUENCE: 2

Met Asn Gly Val Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
            20                  25                  30

Ala Phe Ala Met Phe Pro Ala Thr Phe Arg Ala Gly Phe Met Gly Leu
        35                  40                  45

Asp Glu Phe Arg Phe Gly Ile Glu Gln Met Asn Pro Ala Glu Tyr Leu
    50                  55                  60

Glu Ser Pro Tyr Tyr Trp His Trp Ile Arg Thr Tyr Ile His His Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Glu His Glu Gln Lys
            100                 105                 110

Pro Glu Leu Ile Glu Phe Val Asn Gln Ala Val Tyr Gly Gly Leu Pro
        115                 120                 125

Ala Ser Arg Glu Val Asp Arg Pro Pro Lys Phe Lys Glu Gly Asp Val
    130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Ala Gln Glu Leu Trp Gly Pro Glu Gly
        195                 200                 205

Asp Pro Asn Ser Ser Val Tyr Tyr Asp Cys Trp Glu Pro Tyr Ile Glu
    210                 215                 220

Leu Val Asp Thr Lys Ala Ala Ala
225                 230

<210> SEQ ID NO 3
<211> LENGTH: 618
<212> TYPE: DNA
<213> ORGANISM: Pseudonocardia thermophila

<400> SEQUENCE: 3
atgaccgaga acatcctgcg caagtcggac gaggagatcc agaaggagat cacggcgcgg      60
```

```
gtcaaggccc tggagtcgat gctcatcgaa cagggcatcc tcaccacgtc gatgatcgac      120
cggatggccg agatctacga gaacgaggtc ggcccgcacc tcggcgcgaa ggtcgtcgtg      180
aaggcctgga ccgaccccgga gttcaagaag cgtctgctcg ccgacggcac cgaggcctgc      240
aaggagctcg gcatcggcgg cctgcaggc gaggacatga tgtgggtgga gaacaccgac       300
gaggtccacc acgtcgtcgt gtgcacgctc tgctcctgct accgtggcc ggtgctgggg        360 ctgccgccga actggttcaa ggagccgcag taccgctccc gcgtggtgcg tgagccccgg      420
cagctgctca aggaggagtt cggcttcgag gtcccgccga gcaaggagat caaggtctgg      480
gactccagct ccgagatgcg cttcgtcgtc ctcccgcagc gccccgcggg caccgacggg      540
tggagcgagg aggagctcgc caccctcgtc acccgcgagt cgatgatcgg cgtcgaaccg      600
gcgaaggcgg tcgcgtga                                                    618

<210> SEQ ID NO 4
<211> LENGTH: 702
<212> TYPE: DNA
<213> ORGANISM: Pseudonocardia thermophila

<400> SEQUENCE: 4
atgaacggcg tgtacgacgt cggcggcacc gatgggctgg gcccgatcaa ccggcccgcg       60
gacgaaccgg tcttccgcgc cgagtgggag aaggtcgcgt tcgcgatgtt cccggcgacg      120
ttccgggccg gcttcatggg cctggacgag ttccggttcg gcatcgagca gatgaacccg      180
gccgagtacc tcgagtcgcc gtactactgg cactggatcc gcacctacat ccaccacggc      240
gtccgcaccg gcaagatcga tctcgaggag ctggagcgcc gcacgcagta ctaccgggag      300
aaccccgacg ccccgctgcc cgagcacgag cagaagccgg agttgatcga gttcgtcaac      360
caggccgtct acggcgggct gcccgcaagc cgggaggtcg accgaccgcc caagttcaag      420
gagggcgacg tggtgcggtt ctccaccgcg agcccgaagg gccacgcccg gcgcgcgcgg      480
tacgtgcgcg gcaagaccgg gacggtggtc aagcaccacg gcgcgtacat ctacccggac      540
accgccggca acggcctggg cgagtgcccc gagcacctct acaccgtccg cttcacggcc      600
caggagctgt gggggccgga aggggacccg aactccagcg tctactacga ctgctgggag      660
ccctacatcg agctcgtcga cacgaaggcg gccgcggcat ga                         702

<210> SEQ ID NO 5
<211> LENGTH: 144
<212> TYPE: PRT
<213> ORGANISM: Pseudonocardia thermophila

<400> SEQUENCE: 5

Met Ser Ala Glu Ala Lys Val Arg Leu Lys His Cys Pro Thr Ala Glu
  1               5                  10                  15

Asp Arg Ala Ala Ala Asp Ala Leu Leu Ala Gln Leu Pro Gly Gly Asp
                 20                  25                  30

Arg Ala Leu Asp Arg Gly Phe Asp Glu Pro Trp Gln Leu Arg Ala Phe
             35                  40                  45

Ala Leu Ala Val Ala Ala Cys Arg Ala Gly Arg Phe Glu Trp Lys Gln
         50                  55                  60

Leu Gln Gln Ala Leu Ile Ser Ser Ile Gly Glu Trp Glu Arg Thr His
 65                  70                  75                  80

Asp Leu Asp Asp Pro Ser Trp Ser Tyr Tyr Glu His Phe Val Ala Ala
                 85                  90                  95

Leu Glu Ser Val Leu Gly Glu Glu Gly Ile Val Glu Pro Glu Ala Leu
```

```
              100                 105                 110
Asp Glu Arg Thr Ala Glu Val Leu Ala Asn Pro Pro Asn Lys Asp His
        115                 120                 125

His Gly Pro His Leu Glu Pro Val Ala Val His Pro Ala Val Arg Ser
    130                 135                 140
```

<210> SEQ ID NO 6
<211> LENGTH: 435
<212> TYPE: DNA
<213> ORGANISM: Pseudonocardia thermophila

<400> SEQUENCE: 6

```
gtgagcgccg aggcgaaggt ccgcctgaag cactgcccca cggccgagga ccgggcggcg    60
gccgacgcgc tgctcgcgca gctgcccggc ggcgaccgcg cgctcgaccg cggcttcgac   120
gagccgtggc agctgcgggc gttcgcgctg gcggtcgcgg cgtgcagggc gggccggttc   180
gagtggaagc agctgcagca ggcgctgatc tcctcgatcg gggagtggga gcgcacccac   240
gatctcgacg atccgagctg gtcctactac gagcacttcg tcgccgcgct ggaatccgtg   300
ctcggcgagg aagggatcgt cgagccgagg gcgctggacg agcgcaccgc ggaggtcttg   360
gccaacccgc gaacaagga tcaccatgga ccgcatctgg agcccgtcgc ggtccacccg    420
gccgtgcggt cctga                                                    435
```

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aacatcatgc gcaagtcg                                                  18

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gttttcccag tcacgac                                                   17

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggccagtgcc tagcttacat                                                20

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 10
caggaaacag ctatgac                                                  17

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aacatcacgc gcaagtcg                                                 18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aacatcgcgc gcaagtcg                                                 18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aacatcgtgc gcaagtcg                                                 18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
atcacggtgc gggtcaag                                                 18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
acgtcgttga tcgaccgg                                                 18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 16
gacggctccg aggcctgc                                              18

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ctgcaggccg aggacatg                                              18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gacgaggccc accacgtc                                              18

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cacgtcatcg tgtgcacg                                              18

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aactggtaca aggagccg                                              18

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gagccggagt accgctcc                                              18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
```
cggcaggtgc tcaaggag                                                         18

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aaggaggact tcggcttc                                                         18

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gagctcacca ccctcgtc                                                         18

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cgcgagttga tgatcggc                                                         18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcgaaggagg tcgcgtga                                                         18

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cggcccgtgg acgaaccg                                                         18

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

-continued

```
cccgcgaacg aaccggtc                                                 18

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ctgcccgatc acgagcag                                                 18

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30 ctgccccgc acgagcag                                                  18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ctgccctcgc acgagcag                                                 18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ctgccccggc acgagcag                                                 18

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ctgccctgcc acgagcag                                                 18

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ctgcccctgc acgagcag                                                 18
```

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
ctgcccacgc acgagcag                                                 18

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
ttcacggacc aggagctg                                                 18

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
ttcacgatcc aggagctg                                                 18

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
ttcacggtcc aggagctg                                                 18

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
ttcacggagc aggagctg                                                 18

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
ccgaactaca gcgtctac                                                 18

```
<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ctcaccatgt cgatgatc                                                 18

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
aagaagcatc tgctcgcc                                                 18

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gagttcgact tcgaggtc                                                 18

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
aaggcgcgcg cgtgagcg                                                 18

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
aaggcgaaag cgtgagcg                                                 18

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
aaggcgtggg cgtgagcg                                                 18
```

```
<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
aaggcgaccg cgtgagcg                                                 18

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ggcggcgacg atgggctg                                                 18

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ggcggcgaag atgggctg                                                 18

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ggcggctggg atgggctg                                                 18

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ggcggcggcg atgggctg                                                 18

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ggcggctacg atgggctg                                                 18

<210> SEQ ID NO 53
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ggcggctgcg atgggctg                                                 18

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gagaagggcg cgttcgcg                                                 18

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gcgatgaccc cggcgacg                                                 18

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gcgatggccc cggcgacg                                                 18

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gcgatgctcc cggcgacg                                                 18

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gcgatgatcc cggcgacg                                                 18

<210> SEQ ID NO 59
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gcgatggtcc cggcgacg                                                 18

<210> SEQ ID NO 60
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gcgacggaac gggccggc                                                 18

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gcgacgaccc gggccggc                                                 18

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gcgacggccc gggccggc                                                 18

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gcgacgctcc gggccggc                                                 18

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gcgacgatcc gggccggc                                                 18

<210> SEQ ID NO 65
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 65
gcgacggtcc gggccggc                                                    18

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ggcttcgggg gcctggac                                                    18

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ggcttctatg gcctggac                                                    18

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ggcttcctgg gcctggac                                                    18

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ggcttcaagg gcctggac                                                    18

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ggcttcgatg gcctggac                                                    18

<210> SEQ ID NO 71
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 71
atgggcgggg acgagttc                                                 18

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
atgggcgcgg acgagttc                                                 18

<210> SEQ ID NO 73
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
atgggcgtgg acgagttc                                                 18

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
atgggctcgg acgagttc                                                 18

<210> SEQ ID NO 75
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
atgggcacgg acgagttc                                                 18

<210> SEQ ID NO 76
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
atgggccggg acgagttc                                                 18

<210> SEQ ID NO 77
<211> LENGTH: 18
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 77
gacgaggccc ggttcggc                                                 18

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gacgagtccc ggttcggc                                                 18

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
tggcacttta tccgcacc                                                 18

<210> SEQ ID NO 80
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
atcgaggccg tcaaccag                                                 18

<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
atcgagctcg tcaaccag                                                 18

<210> SEQ ID NO 82
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
atcgagctcg tcaaccag                                                 18

<210> SEQ ID NO 83
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 83
atcgaggtcg tcaaccag                                                 18

<210> SEQ ID NO 84
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ggcggggcgc ccgcaagc                                                 18

<210> SEQ ID NO 85
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
ggcggggtgc ccgcaagc                                                 18

<210> SEQ ID NO 86
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
ggcgggtcgc ccgcaagc                                                 18

<210> SEQ ID NO 87
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gtggtggggt tctccacc                                                 18

<210> SEQ ID NO 88
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
cgcgcgctgt acgtgcgc                                                 18

<210> SEQ ID NO 89
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 89
cgcgcgtggt acgtgcgc                                             18

<210> SEQ ID NO 90
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
aacggcgagg gcgagtgc                                             18

<210> SEQ ID NO 91
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
aacggcgatg gcgagtgc                                             18

<210> SEQ ID NO 92
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
aacggcaagg gcgagtgc                                             18

<210> SEQ ID NO 93
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
aacggccggg gcgagtgc                                             18

<210> SEQ ID NO 94
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
aacggcaacg gcgagtgc                                             18

<210> SEQ ID NO 95
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 95
aacggctcgg gcgagtgc                                                    18

<210> SEQ ID NO 96
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
aacggcgggg gcgagtgc                                                    18

<210> SEQ ID NO 97
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
tactacggct gctgggag                                                    18

<210> SEQ ID NO 98
<211> LENGTH: 205
<212> TYPE: PRT
<213> ORGANISM: Pseudonocardia thermophila

<400> SEQUENCE: 98

Met Thr Glu Asn Ile Leu Arg Lys Ser Asp Glu Glu Ile Gln Lys Glu
  1               5                  10                  15

Ile Thr Ala Arg Val Lys Ala Leu Glu Ser Met Leu Ile Glu Gln Gly
                 20                  25                  30

Ile Leu Thr Thr Ser Met Ile Asp Arg Met Ala Glu Ile Tyr Glu Asn
             35                  40                  45

Glu Val Gly Pro His Leu Gly Ala Lys Val Val Lys Ala Trp Thr
         50                  55                  60

Asp Pro Glu Phe Lys Lys Arg Leu Leu Ala Asp Gly Thr Glu Ala Cys
 65                  70                  75                  80

Lys Glu Leu Gly Ile Gly Gly Leu Gln Gly Glu Asp Met Met Trp Val
                 85                  90                  95

Glu Asn Thr Asp Glu Val His His Val Val Cys Thr Leu Cys Ser
                100                 105                 110

Cys Tyr Pro Trp Pro Val Leu Gly Leu Pro Pro Asn Trp Phe Lys Glu
            115                 120                 125

Pro Gln Tyr Arg Ser Arg Val Val Arg Glu Pro Arg Gln Leu Leu Lys
        130                 135                 140

Glu Glu Phe Gly Phe Glu Val Pro Pro Ser Lys Glu Ile Lys Val Trp
145                 150                 155                 160

Asp Ser Ser Ser Glu Met Arg Phe Val Val Leu Pro Gln Arg Pro Ala
                165                 170                 175

Gly Thr Asp Gly Trp Ser Glu Glu Leu Ala Thr Leu Val Thr Arg
            180                 185                 190

Glu Ser Met Ile Gly Val Glu Pro Ala Lys Ala Val Ala
        195                 200                 205

<210> SEQ ID NO 99
```

<211> LENGTH: 233
<212> TYPE: PRT
<213> ORGANISM: Pseudonocardia thermophila

<400> SEQUENCE: 99

Met Asn Gly Val Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
            20                  25                  30

Ala Phe Ala Met Phe Pro Ala Thr Phe Arg Ala Gly Phe Met Gly Leu
        35                  40                  45

Asp Glu Phe Arg Phe Gly Ile Glu Gln Met Asn Pro Ala Glu Tyr Leu
    50                  55                  60

Glu Ser Pro Tyr Tyr Trp His Trp Ile Arg Thr Tyr Ile His His Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Glu His Glu Gln Lys
            100                 105                 110

Pro Glu Leu Ile Glu Phe Val Asn Gln Ala Val Tyr Gly Gly Leu Pro
        115                 120                 125

Ala Ser Arg Glu Val Asp Arg Pro Lys Phe Lys Glu Gly Asp Val
    130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Ala Gln Glu Leu Trp Gly Pro Glu Gly
        195                 200                 205

Asp Pro Asn Ser Ser Val Tyr Tyr Asp Cys Trp Glu Pro Tyr Ile Glu
    210                 215                 220

Leu Val Asp Thr Lys Ala Ala Ala Ala
225                 230

<210> SEQ ID NO 100
<211> LENGTH: 618
<212> TYPE: DNA
<213> ORGANISM: Pseudonocardia thermophila

<400> SEQUENCE: 100
atgaccgaga acatcctgcg caagtcggac gaggagatcc agaaggagat cacggcgcgg        60
gtcaaggccc tggagtcgat gctcatcgaa cagggcatcc tcaccacgtc gatgatcgac      120
cggatggccg agatctacga gaacgaggtc ggcccgcacc tcggcgcgaa ggtcgtcgtg      180
aaggcctgga ccgacccgga gttcaagaag cgtctgctcg ccgacggcac cgaggcctgc      240
aaggagctcg gcatcggcgg cctgcagggc gaggacatga tgtgggtgga gaacaccgac      300
gaggtccacc acgtcgtcgt gtgcacgctc tgctcctgct acccgtggcc ggtgctgggg      360
ctgccgccga actggttcaa ggagccgcag taccgctccc gcgtggtgcg tgagccccgg      420
cagctgctca aggaggagtt cggcttcgag gtccgccga gcaaggagat caaggtctgg      480
gactccagct ccgagatgcg cttcgtcgtc ctccccgcagc gccccgcggg caccgacggg      540
tggagcgagg aggagctcgc caccctcgtc acccgcgagt cgatgatcgg cgtcgaaccg      600

```
gcgaaggcgg tcgcgtga                                                    618
```

<210> SEQ ID NO 101
<211> LENGTH: 702
<212> TYPE: DNA
<213> ORGANISM: Pseudonocardia thermophila

<400> SEQUENCE: 101

```
atgaacggcg tgtacgacgt cggcggcacc gatgggctgg gcccgatcaa ccggcccgcg    60
gacgaaccgg tcttccgcgc cgagtgggag aaggtcgcgt tcgcgatgtt cccggcgacg   120
ttccgggccg gcttcatggg cctgacgag ttccggttcg gcatcgagca gatgaacccg    180
gccgagtacc tcgagtcgcc gtactactgg cactggatcc gcacctacat ccaccacggc   240
gtccgcaccg gcaagatcga tctcgaggag ctggagcgcc gcacgcagta ctaccgggag   300
aaccccgacg ccccgctgcc cgagcacgag cagaagccgg agttgatcga gttcgtcaac   360
caggccgtct acgcgggct gcccgcaagc cgggaggtcg accgaccgcc caagttcaag   420
gagggcgacg tggtgcggtt ctccaccgcg agcccgaagg ccacgcccg gcgcgcgcgg    480 tacgtgcgcg gcaagaccgg gacggtggtc aagcaccacg gcgcgtacat ctacccggac   540
accgccggca acggcctggg cgagtgcccc gagcacctct acaccgtccg cttcacggcc   600
caggagctgt gggggccgga aggggacccg aactccagcg tctactacga ctgctgggag   660
ccctacatcg agctcgtcga cacgaaggcg gccgcggcat ga                      702
```

<210> SEQ ID NO 102
<211> LENGTH: 144
<212> TYPE: PRT
<213> ORGANISM: Pseudonocardia thermophila

<400> SEQUENCE: 102

```
Met Ser Ala Glu Ala Lys Val Arg Leu Lys His Cys Pro Thr Ala Glu
  1               5                  10                  15

Asp Arg Ala Ala Ala Asp Ala Leu Leu Ala Gln Leu Pro Gly Gly Asp
             20                  25                  30

Arg Ala Leu Asp Arg Gly Phe Asp Glu Pro Trp Gln Leu Arg Ala Phe
         35                  40                  45

Ala Leu Ala Val Ala Ala Cys Arg Ala Gly Arg Phe Glu Trp Lys Gln
     50                  55                  60

Leu Gln Gln Ala Leu Ile Ser Ser Ile Gly Glu Trp Glu Arg Thr His
 65                  70                  75                  80

Asp Leu Asp Asp Pro Ser Trp Ser Tyr Tyr Glu His Phe Val Ala Ala
                 85                  90                  95

Leu Glu Ser Val Leu Gly Glu Glu Gly Ile Val Glu Pro Glu Ala Leu
            100                 105                 110

Asp Glu Arg Thr Ala Glu Val Leu Ala Asn Pro Pro Asn Lys Asp His
        115                 120                 125

His Gly Pro His Leu Glu Pro Val Ala Val His Pro Ala Val Arg Ser
    130                 135                 140
```

<210> SEQ ID NO 103
<211> LENGTH: 435
<212> TYPE: DNA
<213> ORGANISM: Pseudonocardia thermophila

<400> SEQUENCE: 103

```
rtgagcgccg aggcgaaggt ccgcctgaag cactgcccca cggccgagga ccgggcggcg    60
```

-continued

```
gccgacgcgc tgctcgcgca gctgcccggc ggcgaccgcg cgctcgaccg cggcttcgac      120
gagccgtggc agctgcgggc gttcgcgctg cggtcgcggc gtgcagggc gggccggttc       180 gagtggaagc agctgcagca ggcgctgatc tcctcgatcg gggagtggga gcgcacccac      240
gatctcgacg atccgagctg gtcctactac gagcacttcg tcgccgcgct ggaatccgtg      300
ctcggcgagg aagggatcgt cgagccggag gcgctggacg agcgcaccgc ggaggtcttg      360
gccaacccgc cgaacaagga tcaccatgga ccgcatctgg agcccgtcgc ggtccacccg      420
gccgtgcggt cctga                                                      435
```

<210> SEQ ID NO 104
<211> LENGTH: 1315
<212> TYPE: DNA
<213> ORGANISM: Rhodococcus rhodochrous
<220> FEATURE:
<221> NAME/KEY: CDS
<222> LOCATION: (1)..(690)
<220> FEATURE:
<221> NAME/KEY: CDS
<222> LOCATION: (704)..(1315)

<400> SEQUENCE: 104

```
atg gat ggt atc cac gac aca ggc ggc atg acc gga tac gga ccg gtc       48
Met Asp Gly Ile His Asp Thr Gly Gly Met Thr Gly Tyr Gly Pro Val
1               5                   10                  15 ccc tat cag aag gac gag ccc ttc ttc cac tac gag tgg gag ggt cgg       96
Pro Tyr Gln Lys Asp Glu Pro Phe Phe His Tyr Glu Trp Glu Gly Arg
                20                  25                  30 acc ctg tca att ctg act tgg atg cat ctc aag ggc ata tcg tgg tgg      144
Thr Leu Ser Ile Leu Thr Trp Met His Leu Lys Gly Ile Ser Trp Trp
            35                  40                  45 gac aag tcg cgg ttc ttc cgg gag tcg atg ggg aac gaa aac tac gtc      192
Asp Lys Ser Arg Phe Phe Arg Glu Ser Met Gly Asn Glu Asn Tyr Val
        50                  55                  60 aac gag att cgc aac tcg tac tac acc cac tgg ctg agt gcg gca gaa      240
Asn Glu Ile Arg Asn Ser Tyr Tyr Thr His Trp Leu Ser Ala Ala Glu
65                  70                  75                  80 cgt atc ctc gtc gcc gac aag atc atc acc gaa gaa gag cga aag cac      288
Arg Ile Leu Val Ala Asp Lys Ile Ile Thr Glu Glu Glu Arg Lys His
                85                  90                  95 cgt gtg caa gag atc ctt gag ggt cgg tac acg gac agg aag ccg tcg      336
Arg Val Gln Glu Ile Leu Glu Gly Arg Tyr Thr Asp Arg Lys Pro Ser
                100                 105                 110 cgg aag ttc gat ccg gcc cag atc gag aag gcg atc gaa cgg ctt cac      384
Arg Lys Phe Asp Pro Ala Gln Ile Glu Lys Ala Ile Glu Arg Leu His
            115                 120                 125 gag ccc cac tcc cta gcg ctt cca gga gcg gag ccg agt ttc tct ctc      432
Glu Pro His Ser Leu Ala Leu Pro Gly Ala Glu Pro Ser Phe Ser Leu
        130                 135                 140 ggt gac aag atc aaa gtg aag agt atg aac ccg ctg gga cac aca cgg      480
Gly Asp Lys Ile Lys Val Lys Ser Met Asn Pro Leu Gly His Thr Arg
145                 150                 155                 160 tgc ccg aaa tat gtg cgg aac aag atc ggg gaa atc gtc gcc tac cac      528
Cys Pro Lys Tyr Val Arg Asn Lys Ile Gly Glu Ile Val Ala Tyr His
                165                 170                 175 ggc tgc cag atc tat ccc gag agc agc tcc gcc ggc ctc ggc gac gat      576
Gly Cys Gln Ile Tyr Pro Glu Ser Ser Ser Ala Gly Leu Gly Asp Asp
                180                 185                 190 cct cgc ccg ctc tac acg gtc gcg ttt tcc gcc cag gaa ctg tgg ggc      624
Pro Arg Pro Leu Tyr Thr Val Ala Phe Ser Ala Gln Glu Leu Trp Gly
            195                 200                 205
```

-continued

| | | |
|---|---|---|
| gac gac gga aac ggg aaa gac gta gtg tgc gtc gat ctc tgg gaa ccg<br>Asp Asp Gly Asn Gly Lys Asp Val Val Cys Val Asp Leu Trp Glu Pro<br>210                              215                     220 | | 672 |
| tac ctg atc tct gcg tgaaaggaat acgata gtg agc gag cac gtc aat aag<br>Tyr Leu Ile Ser Ala                            Met Ser Glu His Val Asn Lys<br>225                                                 1                          5 | | 724 |

```
gac gac gga aac ggg aaa gac gta gtg tgc gtc gat ctc tgg gaa ccg      672
Asp Asp Gly Asn Gly Lys Asp Val Val Cys Val Asp Leu Trp Glu Pro
210                 215                 220 tac ctg atc tct gcg tgaaaggaat acgata gtg agc gag cac gtc aat aag    724
Tyr Leu Ile Ser Ala                    Met Ser Glu His Val Asn Lys
225                                      1               5 tac acg gag tac gag gca cgt acc aag gcg atc gaa acc ttg ctg tac      772
Tyr Thr Glu Tyr Glu Ala Arg Thr Lys Ala Ile Glu Thr Leu Leu Tyr
         10                  15                  20 gag cga ggg ctc atc acg ccc gcg gtc gac cga gtc gtt tcg tac          820
Glu Arg Gly Leu Ile Thr Pro Ala Val Asp Arg Val Val Ser Tyr
 25                  30                  35 tac gag aac gag atc ggc ccg atg ggc ggt gcc aag gtc gtg gcc aag      868
Tyr Glu Asn Glu Ile Gly Pro Met Gly Gly Ala Lys Val Val Ala Lys
 40                  45                  50                  55 tcc tgg gtg gac cct gag tac cgc aag tgg ctc gaa gag gac gcg acg      916
Ser Trp Val Asp Pro Glu Tyr Arg Lys Trp Leu Glu Glu Asp Ala Thr
                 60                  65                  70 gcc gcg atg gcg tca ttg ggc tat gcc ggt gag cag gca cac caa att      964
Ala Ala Met Ala Ser Leu Gly Tyr Ala Gly Glu Gln Ala His Gln Ile
             75                  80                  85 tcg gcg gtc ttc aac gac tcc caa acg cat cac gtg gtg gtg tgc act     1012
Ser Ala Val Phe Asn Asp Ser Gln Thr His His Val Val Val Cys Thr
         90                  95                 100 ctg tgt tcg tgc tat ccg tgg ccg gtg ctt ggt ctc ccg ccc gcc tgg     1060
Leu Cys Ser Cys Tyr Pro Trp Pro Val Leu Gly Leu Pro Pro Ala Trp
105                 110                 115 tac aag agc atg gag tac cgg tcc cga gtg gta gcg gac cct cgt gga     1108
Tyr Lys Ser Met Glu Tyr Arg Ser Arg Val Val Ala Asp Pro Arg Gly
120                 125                 130                 135 gtg ctc aag cgc gat ttc ggt ttc gac atc ccc gat gag gtg gag gtc     1156
Val Leu Lys Arg Asp Phe Gly Phe Asp Ile Pro Asp Glu Val Glu Val
                140                 145                 150 agg gtt tgg gac agc agc tcc gaa atc cgc tac atc gtc atc ccg gaa     1204
Arg Val Trp Asp Ser Ser Ser Glu Ile Arg Tyr Ile Val Ile Pro Glu
            155                 160                 165 cgg ccg gcc ggc acc gac ggt tgg tcc gag gag gag ctg acg aag ctg     1252
Arg Pro Ala Gly Thr Asp Gly Trp Ser Glu Glu Glu Leu Thr Lys Leu
        170                 175                 180 gtg agc cgg gac tcg atg atc ggt gtc agt aat gcg ctc aca ccg cag     1300
Val Ser Arg Asp Ser Met Ile Gly Val Ser Asn Ala Leu Thr Pro Gln
185                 190                 195 gaa gtg atc gta tga                                                 1315
Glu Val Ile Val
200

<210> SEQ ID NO 105
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
ccggaattcg aaaggaatga ggaaatgga                                       29

<210> SEQ ID NO 106
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 106
aaaaagtact catacgatca cttcctgc                                           28

<210> SEQ ID NO 107
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
gttttcccag tcacgac                                                       17

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
ggccagtgcc tagcttacat                                                    20

<210> SEQ ID NO 109
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
caggaaacag ctatgac                                                       17

<210> SEQ ID NO 110
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(16)
<223> OTHER INFORMATION: a, c, g, t, unknown or other

<400> SEQUENCE: 110
gggcatatcg tggnnngaca agtcgcggt                                          29

<210> SEQ ID NO 111
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(9)
<223> OTHER INFORMATION: a, c, g, t, unknown or other

<400> SEQUENCE: 111
```

```
ctcaccnnnt cgatgatc                                                 18
```

<210> SEQ ID NO 112
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(9)
<223> OTHER INFORMATION: a, c, g, t, unknown or other

<400> SEQUENCE: 112

```
tacgagnnng aggtcggc                                                 18
```

<210> SEQ ID NO 113
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(9)
<223> OTHER INFORMATION: a, c, g, t, unknown or other

<400> SEQUENCE: 113

```
aagaagnnnc tgctcgcc                                                 18
```

<210> SEQ ID NO 114
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(9)
<223> OTHER INFORMATION: a, c, g, t, unknown or other

<400> SEQUENCE: 114

```
gagttcnnnt tcgaggtc                                                 18
```

<210> SEQ ID NO 115
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(9)
<223> OTHER INFORMATION: a, c, g, t, unknown or other

<400> SEQUENCE: 115

```
ctcgccnnnc tcgtcact                                                 18
```

<210> SEQ ID NO 116
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:

<221> NAME/KEY: modified_base
<222> LOCATION: (7)..(9)
<223> OTHER INFORMATION: a, c, g, t, unknown or other

<400> SEQUENCE: 116
aaggcgnnng cgtgagcg                                                 18

<210> SEQ ID NO 117
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(9)
<223> OTHER INFORMATION: a, c, g, t, unknown or other

<400> SEQUENCE: 117
ggcggcnnng atgggctg                                                 18

<210> SEQ ID NO 118
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(9)
<223> OTHER INFORMATION: a, c, g, t, unknown or other

<400> SEQUENCE: 118
gagaagnnng cgttcgcg                                                 18

<210> SEQ ID NO 119
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(9)
<223> OTHER INFORMATION: a, c, g, t, unknown or other

<400> SEQUENCE: 119
aaggtcnnnt tcgcgatg                                                 18

<210> SEQ ID NO 120
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(9)
<223> OTHER INFORMATION: a, c, g, t, unknown or other

<400> SEQUENCE: 120
gcgatgnnnc cggcgacg                                                 18

<210> SEQ ID NO 121
<211> LENGTH: 18

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(9)
<223> OTHER INFORMATION: a, c, g, t, unknown or other

<400> SEQUENCE: 121
ccggcgnnnt tccgggcc                                                     18

<210> SEQ ID NO 122
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(9)
<223> OTHER INFORMATION: a, c, g, t, unknown or other

<400> SEQUENCE: 122
gcgacgnnnc gggccggc                                                     18

<210> SEQ ID NO 123
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(9)
<223> OTHER INFORMATION: a, c, g, t, unknown or other

<400> SEQUENCE: 123
ggcttcnnng gcctggac                                                     18

<210> SEQ ID NO 124
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(9)
<223> OTHER INFORMATION: a, c, g, t, unknown or other

<400> SEQUENCE: 124
atgggcnnng acgagttc                                                     18

<210> SEQ ID NO 125
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(9)
<223> OTHER INFORMATION: a, c, g, t, unknown or other

<400> SEQUENCE: 125
```
gacgagnnnc ggttcggc                                            18

<210> SEQ ID NO 126
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(9)
<223> OTHER INFORMATION: a, c, g, t, unknown or other

<400> SEQUENCE: 126
aacccgnnng agtacctc                                            18

<210> SEQ ID NO 127
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(9)
<223> OTHER INFORMATION: a, c, g, t, unknown or other

<400> SEQUENCE: 127
tggcacnnna tccgcacc                                            18

<210> SEQ ID NO 128
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(9)
<223> OTHER INFORMATION: a, c, g, t, unknown or other

<400> SEQUENCE: 128
gagcagnnnc cggagttg                                            18

<210> SEQ ID NO 129
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(9)
<223> OTHER INFORMATION: a, c, g, t, unknown or other

<400> SEQUENCE: 129
atcgagnnng tcaaccag                                            18

<210> SEQ ID NO 130
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

```
<220> FEATURE:
<221> NAME/KEY: modified_base
<222> LOCATION: (7)..(9)
<223> OTHER INFORMATION: a, c, g, t, unknown or other

<400> SEQUENCE: 130
ggcgggnnnc ccgcaagc                                                 18

<210> SEQ ID NO 131
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(9)
<223> OTHER INFORMATION: a, c, g, t, unknown or other

<400> SEQUENCE: 131
gtggtgnnnt tctccacc                                                 18

<210> SEQ ID NO 132
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(9)
<223> OTHER INFORMATION: a, c, g, t, unknown or other

<400> SEQUENCE: 132
tccaccnnna gcccgaag                                                 18

<210> SEQ ID NO 133
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(9)
<223> OTHER INFORMATION: a, c, g, t, unknown or other

<400> SEQUENCE: 133
cgcgcgnnnt acgtgcgc                                                 18

<210> SEQ ID NO 134
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(9)
<223> OTHER INFORMATION: a, c, g, t, unknown or other

<400> SEQUENCE: 134
accgggnnng tggtcaag                                                 18

<210> SEQ ID NO 135
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(9)
<223> OTHER INFORMATION: a, c, g, t, unknown or other

<400> SEQUENCE: 135
gtggtcnnnc accacggc                                                18

<210> SEQ ID NO 136
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(9)
<223> OTHER INFORMATION: a, c, g, t, unknown or other

<400> SEQUENCE: 136
ggcgcgnnna tctacccg                                                18

<210> SEQ ID NO 137
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(9)
<223> OTHER INFORMATION: a, c, g, t, unknown or other

<400> SEQUENCE: 137
aacggcnnng gcgagtgc                                                18

<210> SEQ ID NO 138
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(9)
<223> OTHER INFORMATION: a, c, g, t, unknown or other

<400> SEQUENCE: 138
tactacnnnt gctgggag                                                18

<210> SEQ ID NO 139
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (7)..(9)
<223> OTHER INFORMATION: a, c, g, t, unknown or other
```

<400> SEQUENCE: 139
tacgacnnnt gggagccc                                                                                  18

<210> SEQ ID NO 140
<211> LENGTH: 229
<212> TYPE: PRT
<213> ORGANISM: Rhodococcus rhodochrous

<400> SEQUENCE: 140

Met Asp Gly Ile His Asp Thr Gly Gly Met Thr Gly Tyr Gly Pro Val
1               5                   10                  15

Pro Tyr Gln Lys Asp Glu Pro Phe Phe His Tyr Glu Trp Glu Gly Arg
            20                  25                  30

Thr Leu Ser Ile Leu Thr Trp Met His Leu Lys Gly Ile Ser Trp Trp
        35                  40                  45

Asp Lys Ser Arg Phe Phe Arg Glu Ser Met Gly Asn Glu Asn Tyr Val
    50                  55                  60

Asn Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Arg Lys His
            85                  90                  95

Arg Val Gln Glu Ile Leu Glu Gly Arg Tyr Thr Asp Arg Lys Pro Ser
            100                 105                 110

Arg Lys Phe Asp Pro Ala Gln Ile Glu Lys Ala Ile Glu Arg Leu His
        115                 120                 125

Glu Pro His Ser Leu Ala Leu Pro Gly Ala Glu Pro Ser Phe Ser Leu
    130                 135                 140

Gly Asp Lys Ile Lys Val Lys Ser Met Asn Pro Leu Gly His Thr Arg
145                 150                 155                 160

Cys Pro Lys Tyr Val Arg Asn Lys Ile Gly Glu Ile Val Ala Tyr His
                165                 170                 175

Gly Cys Gln Ile Tyr Pro Glu Ser Ser Ser Ala Gly Leu Gly Asp Asp
            180                 185                 190

Pro Arg Pro Leu Tyr Thr Val Ala Phe Ser Ala Gln Glu Leu Trp Gly
        195                 200                 205

Asp Asp Gly Asn Gly Lys Asp Val Val Cys Val Asp Leu Trp Glu Pro
    210                 215                 220

Tyr Leu Ile Ser Ala
225

<210> SEQ ID NO 141
<211> LENGTH: 203
<212> TYPE: PRT
<213> ORGANISM: Rhodococcus rhodochrous

<400> SEQUENCE: 141

Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Met Ala Ser Leu Gly Tyr Ala
65                  70                  75                  80

```
Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
        130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175

Glu Glu Glu Leu Thr Lys Leu Val Ser Arg Asp Ser Met Ile Gly Val
            180                 185                 190

Ser Asn Ala Leu Thr Pro Gln Glu Val Ile Val
        195                 200

<210> SEQ ID NO 142
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: variable amino acid
<220> FEATURE:
<221> NAME/KEY: MOD_RES
<222> LOCATION: (3)
<223> OTHER INFORMATION: Ser or Thr
<220> FEATURE:
<221> NAME/KEY: MOD_RES
<222> LOCATION: (1)
<223> OTHER INFORMATION: variable amino acid
<220> FEATURE:
<221> NAME/KEY: MOD_RES
<222> LOCATION: (5)
<223> OTHER INFORMATION: cysteine sulfinic acid
<220> FEATURE:
<221> NAME/KEY: MOD_RES
<222> LOCATION: (7)
<223> OTHER INFORMATION: cysteine sulfenic acid
<220> FEATURE:
<221> NAME/KEY: MOD_RES
<222> LOCATION: (8)..(11)
<223> OTHER INFORMATION: variable amino acid

<400> SEQUENCE: 142

Xaa Cys Xaa Leu Cys Ser Cys Xaa Xaa Xaa Xaa
 1               5                  10
```

NITRILE HYDRATASE VARIANT

TECHNICAL FIELD

The present invention relates to a novel nitrile hydratase, as well as to a gene encoding the enzyme, to a plasmid containing the gene, to a transformant strain as transformed with the plasmid, to a method for producing a nitrile hydratase using the transformant strain, and to a method for processing a nitrile compound with a culture obtained from cultivating the transformant strain, with the cultivated cells or with a product obtained by processing the cultivated cells, to produce a corresponding amide compound.

Further, the invention relates to a process for modifying the properties of an enzyme having the activity of nitrile hydratase. Furthermore, the invention relates to an enzyme with modified properties, as well as to a gene encoding the enzyme, to a plasmid containing the gene, to a transformant strain transformed with the plasmid, to a method for producing a nitrile hydratase using the transformant strain, and to a method for processing a nitrile compound with a culture obtained from cultivating the transformant strain, with the cultivated cells or with a product obtained by processing the cultivated cells, to produce a corresponding amide compound. The invention is useful in the field of material production using a biological catalyst.

BACKGROUND ART

A nitrile hydratase has been discovered which is an enzyme having the nitrile-hydrating activity to convert a nitrile group of various compounds to an amide group by hydration, and a number of microorganism strains producing the above-mentioned enzyme have been introduced. In order to produce an amide compound from a nitrile compound using a nitrile hydratase on an industrial scale, it is important to reduce the proportion of the production costs for this enzyme in the total production costs for producing the amide compound. More specifically, it is necessary to increase the content of the enzyme in a unit weight of the preparation obtained from the enzyme production. Thus, attempts have been being made to clone the gene of the enzyme for the purpose of expressing a large amount of the enzyme through genetic engineering means using the gene of the enzyme.

As the microorganisms having the activity of nitrile hydratase, *Rhodococcus rhodochrous* strain J1 (deposited under the Budapest Treaty with the International Patent Organism Depositary at the National Institute of Advanced Industrial Science and Technology, Tsukuba Central 6, 1-1-1 Higashi, Tsukuba-shi, Ibaraki-ken, Japan, under the deposit number FERM BP-1478) and *Pseudonocardia thermophila* (this strain is in storage in the Japan collection of Microorganisms at RIKEN BioResource Center, 2-1 Hirosawa, Wako-shi, Saitama-ken 351-0198, Japan, under the accession number JCM3095 and may be freely distributed to anyone upon request. Also, it is deposited under the Budapest Treaty with the International Patent Organism Depositary at the National Institute of Advanced Industrial Science and Technology, under the deposit number FERM BP-7379) are known (see Patent Documents 1 and 3).

In addition, a nitrile hydratase has been isolated from these strains, and it has been confirmed that this enzyme consists of two types of polypeptides generally referred to as an α-subunit and a β-subunit. Further, the gene of the nitrile hydratase has been isolated from these strains, and the amino acid sequence and the base sequence for the enzyme have been identified. Also, the plasmid which can express the nitrile hydratase in a transformant and the strain transformed with this plasmid (for example, TG1/pNHJ10H and MT-10822: under the Budapest Treaty, the former is deposited with the International Patent Organism Depositary at the National Institute of Advanced Industrial Science and Technology under the deposit number FERM BP-2777, and the latter is deposited with the International Patent Organism Depositary at the National Institute of Advanced Industrial Science and Technology, Tsukuba Central 6, 1-1-1 Higashi, Tsukuba-shi, Ibaraki-ken, Japan, under the deposit number FERM BP-5785, as of Feb. 7, 1996) have been prepared. Additionally, it has been made possible to produce a nitrile hydratase by means of these strains, and to process a nitrile compound to produce a corresponding amide compound by bringing the strain or the nitrile hydratase obtained therefrom into contact with the nitrile compound (see Patent Documents 2 and 4, and Non-patent Document 1).

Also, attempts have been being made to interpret the stereostructure of a nitrile hydratase, and the interpretation results have been disclosed under PDB ID NOs: 1AHJ, 2AHJ and 1IRE. It is clear now that the enzyme comprises a dimer having the α-subunit and the β-subunit which are in association as the fundamental structural unit, and the dimers are further associated to form tetramers, octamers or dodecamers (depending on the biological species of origin) in order to express the activity. Further, the region or structure forming the active center has been identified, and it is known that the active center is not at an exposed position on the external side of the enzyme where direct contact is made with the reaction solvent, but at a position where it looks like being embedded inside the enzyme. Also known is the stereostructure in which a metal atom that is essential for expression of the activity (cobalt atom or iron atom, depending on the biological species of origin) is coordinated to the active center, and it has been disclosed that a cysteine residue in the amino acid sequence that constitutes the region forming the active center undergoes oxidation after transcription, as a phenomenon associated with the coordination of a metal atom. Specifically, a region represented by the sequence $X_1CXLC_1SC_2X_2X_3X_4X_5$ (SEQ ID NO: 142) (wherein, C corresponds to cysteine, X to serine or threonine, L to leucine, $C_1$ to cysteine sulfinic acid (cysteine sulfinic acid.3-sulfinoalanine), S to serine, and $C_2$ to cysteine sulfenic acid (cysteine sulfenic acid S-hydroxy-cysteine); and $X_1$, $X_2$, $X_3$, $X_4$ and $X_5$ represent arbitrary amino acid, respectively) in the amino acid sequence of the α-subunit is known as the region responsible for the coordination of the metal atom to the active center (see Non-patent Documents 2 to 4).

However, with regard to the method of modifying the properties of the nitrile hydratase, without impairing the original activity thereof, such as the enzymatic activity, substrate-specificity, $V_{max}$, $K_m$, thermal stability, stability against the substrate, stability against the product or the like, no invention has been reported which discloses a specific technique therefor. In particular, no attempt has been made regarding the method of modifying the above-mentioned properties by paying attention to the stereostructure of the nitrile hydratase and changing the stereostructure.

Furthermore, it is disclosed in Patent Document 5 that in the case of producing a nitrile hydratase having the enzymatic activity by expressing a gene that codes for nitrile hydratase using a host cell, there exists a protein which is involved in the activation of the enzyme.

Patent Document 1: Japanese Patent Application Laid-Open No. 2-470

Patent Document 2: Japanese Patent Application Laid-Open No. 4-211379

Patent Document 3: Japanese Patent Application Laid-Open No. 8-56684

Patent Document 4: Japanese Patent Application Laid-Open No. 9-275978

Patent Document 5: Japanese Patent Application Laid-Open No. 11-253168

Non-patent Document 1: Kobayashi M, Nishiyama M, Nagasawa T, Horinouchi S, Beppu T, Yamada H. Cloning, nucleotide sequence and expression in *Escherichia coli* of two cobalt-containing nitrile hydratase genes from *Rhodococcus rhodochrous* J1. Biochim Biophys Acta. 1991 Dec. 2; 1129 (1): 23-33.

Non-patent Document 2: Huang W, Jia J, Cummings J, Nelson M, Schneider G, Lindqvist Y. Crystal structure of nitrile hydratase reveals a novel iron centre in a novel fold. Structure. 1997 May 15; 5(5): 691-9.

Non-patent Document 3: Nagashima S, Nakasako M, Dohmae N, Tsujimura M, Takio K, Odaka M, Yohda M, Kamiya N, Endo I. Novel non-heme iron center of nitrile hydratase with a claw setting of oxygen atoms. Nat Struct Biol. 1998 May; 5(5): 347-51.

Non-patent Document 4: Miyanaga, A., Fushinobu, S., Ito, K., and Wakagi, T. Crystal structure of cobalt-containing nitrile hydratase. Biochem. Biochem Biophys Res Commun. 2001 Nov. 16; 288(5): 1169-74.

DISCLOSURE OF INVENTION

It is an advantage of the invention to provide the amino acid sequence of a nitrile hydratase which has a novel substitution mutation site that does not substantially modify the function, and the base sequence of the gene encoding the enzyme. Moreover, it is to provide a plasmid containing the gene, a transformant strain transformed with the plasmid, a process for producing a nitrile hydratase using the transformant strain, and a process for processing a nitrile compound with a culture obtained from cultivating the transformant strain, with the cultivated cells or with a product obtained by processing the cultivated cells, to produce a corresponding amide compound.

Further, another advantage of the invention is to provide a specific technique relating to a method comprising modification of one or more properties of nitrile hydratase such as the enzymatic activity, substrate specificity, $V_{max}$, $K_m$, thermal stability, stability against the substrate, stability against the product or the like, without impairing the enzyme's original activity. More specifically, it is to provide a method for modifying the properties by introducing into the nitrile hydratase gene a mutation which effects a change in the stereostructure of the nitrile hydratase. It is also to provide a nitrile hydratase obtained according to the method for modification, a gene encoding the nitrile hydratase, a plasmid containing the gene, a transformant strain transformed with the gene or the plasmid, a method for producing the nitrile hydratase using the transformant strain, and a method for processing a nitrile compound with a culture obtained from cultivating the transformant strain, with the cultivated cells or with a product obtained by processing the cultivated cells, to produce a corresponding amide compound.

Under these circumstances, the inventors succeeded in introducing into the nitrile hydratase gene disclosed in Japanese Patent Application Laid-Open No. 9-275978 (Patent Document 4), a novel substitution mutation site that is not disclosed in the above-mentioned publication and determined the base sequence of the gene after the introduction of the mutation. Furthermore, they produced a plasmid containing the gene and a transformant strain transformed with the plasmid. They have also made extensive studies on preparing the enzyme using the strain or processing a nitrile compound using a culture obtained from cultivating the transformant strain, with the cultivated cells or with a product obtained by processing the cultivated cells, to produce a corresponding amide compound. As a result, the invention was completed.

The α-subunit of the nitrile hydratase according to the invention is characterized in that it has an amino acid sequence containing mutation in which at least one amino acid of the $36^{th}$, $71^{st}$, $148^{th}$ and $204^{th}$ amino acids in the amino acid sequence of the α-subunit as set forth in SEQ ID NO: 1 in the Sequence Listing is substituted by another amino acid.

The β-subunit of the nitrile hydratase according to the invention is characterized in that it has an amino acid sequence containing mutation in which at least one amino acid of the $10^{th}$, $32^{nd}$, $37^{th}$, $41^{st}$, $46^{th}$, $48^{th}$, $51^{st}$, $72^{nd}$, $118^{th}$, $127^{th}$, $146^{th}$, $160^{th}$, $186^{th}$ and $217^{th}$ amino acids in the amino acid sequence of the β-subunit as set forth in SEQ ID NO: 2 in the Sequence Listing is substituted by another amino acid.

The nitrile hydratase according to the invention is characterized in that it comprises an α-subunit and a β-subunit, and at least one of these subunits has the above-mentioned mutation.

The gene encoding the α-subunit of the nitrile hydratase according to the invention is characterized in that it codes for an amino acid sequence having mutation in the α-subunit. The gene encoding the β-subunit of the nitrile hydratase according to the invention is characterized in that it codes for an amino acid sequence having mutation in the β-subunit.

The gene encoding the nitrile hydratase according to the invention is characterized in that it comprises the gene encoding the α-subunit and the gene encoding the β-subunit, and at least one of these subunits has the above-mentioned mutation.

The plasmid of the invention is characterized in having any one of the above-mentioned genes.

The transformant of the invention is characterized in that it is obtained by transformation of a host cell using the plasmid.

The production of the nitrile hydratase of the invention is characterized in comprising a step of recovering the nitrile hydratase from the transformant, a culture obtained from cultivation of the transformants, or the product obtained from the processing of the transformants or the culture.

The method for producing an amide compound according to the invention is characterized in comprising a step of bringing a nitrile compound into contact with the nitrile hydratase in an aqueous medium to convert the nitrile compound to a corresponding amide compound.

Moreover, under these circumstances, taking an example from the nitrile hydratase genes disclosed in Patent Document 2 and Patent Document 4, the inventors specified a region to be subjected to mutation, based on the aspect of novelty, and implemented the method for modifying a nitrile hydratase by applying alteration such as substitution, insertion or deletion at the amino acids in the amino acid sequence which correspond to the amino acid residues forming the region. Specifically, the inventors specified the region to be modified in accordance with the purpose, by carrying out an assiduous interpretation with reference to the stereostructure of the nitrile hydratase as disclosed in the Non-patent Documents 2, 3 and 4 and in PDB ID NOs: 1AHJ, 2AHJ and 1IRE. More specifically, by the interpretation of the stereostructure, they specified the region which forms a cavity through which a substrate passes from the outside of the enzyme toward the active center or a product passes from the active center toward the outside of the enzyme, and the region which forms an associative interface between the α-subunit and the β-subunit which is involved in the formation of dimers or an interface involved in the association of dimers. The method for applying alteration such as substitution, insertion or deletion into an amino acid sequence is not particularly limited and may be exemplified by the technique of mutagenesis which employs the gene recombination technology.

In addition, the inventors observed how the method for modification changes the properties of nitrile hydratase, by determining the base sequence of the gene after the above-mentioned alteration, producing a plasmid containing the gene and a transformant strain transformed with the gene or the plasmid, and then performing the production of the enzyme using the transformant strain or the processing of a nitrile compound with a culture obtained from cultivating the transformant strain, with the cultivated cells or with a product obtained by processing the cultivated cells, to produce a corresponding amide compound. After a close examination on the alteration at various sites in the amino acid sequence constituting the nitrile hydratase to be modified, and on various modified enzymes obtained therefrom, the inventors eventually accomplished the invention.

Therefore, the invention relates to, in addition to the above-described features, the following [1] to [22]:

[1] a method for modifying an enzyme having the nitrile hydratase activity, which comprises changing one or more properties selected from the enzyme activity, substrate specificity, $V_{max}$, $K_m$, thermal stability, stability against the substrate and stability against the product, by specifying certain amino acid residues and performing substitution, insertion or deletion at one or more sites of the specified amino acid residues according to the following procedure:

(a) aligning the amino acid sequence of the enzyme having the nitrile hydratase activity before modification, with the amino acid sequence as set forth in SEQ ID NO: 98 in the Sequence Listing and the amino acid sequence as set forth in SEQ ID NO: 99 in the Sequence Listing, (b) specifying, based on the results of the alignment, the amino acid residues corresponding to the region extending from the $36^{th}$ threonine to the $48^{th}$ asparagine in the amino acid sequence as set forth in SEQ ID NO: 98 in the Sequence Listing, and to the region extending from the $31^{st}$ lysine to the $51^{st}$ phenylalanine and to the region extending from the $112^{th}$ lysine to the $127^{th}$ leucine in the amino acid sequence as set forth in SEQ ID NO: 99 in the Sequence Listing, and (c) performing substitution, insertion or deletion at one or more sites of the specified amino acid residues;

[2] a method for modifying an enzyme having the nitrile hydratase activity, which comprises changing one or more properties selected from the enzyme activity, substrate specificity, $V_{max}$, $K_m$, thermal stability, stability against the substrate and stability against the product, by specifying certain amino acid residues and performing substitution, insertion or deletion at one or more sites of the specified amino acid residues according to the following procedure:

(d) aligning the amino acid sequence of the enzyme having the nitrile hydratase activity before modification, with the amino acid sequence as set forth in SEQ ID NO: 98 in the Sequence Listing and the amino acid sequence as set forth in SEQ ID NO: 99 in the Sequence Listing, (e) specifying, based on the results of the alignment, the amino acid residues corresponding to the $36^{th}$, $48^{th}$, $71^{st}$, $148^{th}$, $188^{th}$ and $204^{th}$ of the amino acid sequence as set forth in SEQ ID NO: 98 in the Sequence Listing, and of the amino acid residues corresponding to the $10^{th}$, $32^{nd}$, $33^{rd}$, $37^{th}$, $40^{th}$, $41^{st}$, $46^{th}$, $48^{th}$, $51^{st}$, $61^{st}$, $72^{nd}$, $112^{th}$, $118^{th}$, $127^{th}$, $146^{th}$, $150^{th}$, $160^{th}$, $168^{th}$, $171^{st}$, $176^{th}$, $186^{th}$, $217^{th}$ and $218^{th}$ of the amino acid sequence as set forth in SEQ ID NO: 99 in the Sequence Listing, and (f) performing substitution, insertion or deletion at one or more sites of the specified amino acid residues;

[3] a method for modifying an enzyme having the nitrile hydratase activity, which comprises changing one or more properties selected from the enzymatic activity, substrate specificity, $V_{max}$, $K_m$, thermal stability, stability against the substrate and stability against the product, by specifying certain amino acid residues and performing substitution, insertion or deletion at one or more sites of the specified amino acid residues according to the following procedure:

(g) inferring the stereostructure of the enzyme having the nitrile hydratase activity before modification by carrying out an alignment based on the nitrile hydratase stereostructure and the amino acid sequence as set forth in PDB (Protein Data Bank) ID NO: 1IRE, (h) specifying, based on the stereostructure inferred, the amino acid residues in the regions corresponding to the $2^{nd}$ helix as counted from the N-terminal in Chain 1IRE: A, and to the $1^{st}$ helix and the $2^{nd}$ helix as counted from the N-terminal, the loop portions inserted in the latter helices and the $3^{rd}$ helix as counted from the C-terminal in Chain 1IRE: B in the nitrile hydratase stereostructure as set forth in PDB ID NO: 1IRE, and (i) performing substitution, insertion or deletion at one or more sites of the specified amino acid residues;

[4] a method for modifying an enzyme having the nitrile hydratase activity, which comprises changing one or more properties selected from the enzymatic activity, substrate specificity, $V_{max}$, $K_m$, thermal stability, stability against the substrate and stability against the product, by specifying certain amino acid residues and performing substitution, insertion or deletion at one or more sites of the specified amino acid residues according to the following procedure:

(j) inferring the stereostructure of the enzyme having the nitrile hydratase activity before modification by carrying out an alignment based on the nitrile hydratase stereostructure and the amino acid sequence as set forth in PDB ID NO: 1IRE, (k) specifying, based on the stereostructure inferred, the four amino acid residues such as the amino acid residues which correspond to the $89^{th}$ amino acid residue glutamine and the $165^{th}$ amino acid residue glutamic acid as counted from the N-terminal in Chain A, and the amino acid residues which correspond to the $37^{th}$ amino acid residue phenylalanine and the $48^{th}$ amino acid leucine as counted from the N-terminal in Chain B in the nitrile hydratase stereostructure as set forth in PDB ID NO: 1IRE, (l) specifying the amino acid residues whose side-chain front-end heavy atoms are located within 5 Å of radius in the respective stereostructure having each of the side-chain front-end heavy atoms of the four above-specified amino acid residues as the point center, and (m) performing substitution, insertion or deletion at one or more of the amino acid residues specified in the above (l);

[5] a method for modifying an enzyme having the nitrile hydratase activity, which comprises changing one or more properties selected from the enzymatic activity, substrate specificity, $V_{max}$, $K_m$, thermal stability, stability against the substrate and stability against the product, by specifying certain amino acid residues and performing substitution, insertion or deletion at one or more sites of the specified amino acid residues according to the following procedure:

(n) inferring the stereostructure of the enzyme having the nitrile hydratase activity before modification by carrying out an alignment based on the nitrile hydratase stereostructure and the amino acid sequence as set forth in PDB ID NO: 1IRE, (o) specifying, based on the inferred stereostructure, the region which forms a cavity through which a substrate passes from the outside of the enzyme toward the active center, or a product passes from the active center to the outside of the enzyme, (p) specifying, among the amino acid residues constituting the above-specified region, the amino acid residues whose alteration leads to a change in the cavity size and further controls the easiness or difficulty in passing of the substrate/product, and (q) performing substitution, insertion or deletion at one or more of the amino acid residues specified in the above (p);

[6] a method for modifying an enzyme having the nitrile hydratase activity, which comprises changing one or more properties selected from the enzymatic activity, substrate specificity, $V_{max}$, $K_m$, thermal stability, stability against the substrate and stability against the product, by specifying certain amino acid residues and performing substitution, insertion or deletion at one or more sites of the specified amino acid residues according to the following procedure:

(r) inferring the stereostructure of the enzyme having the nitrile hydratase activity before modification by carrying out an alignment based on the nitrile hydratase stereostructure and the amino acid sequence as set forth in PDB ID NO: 1IRE, (s) specifying, based on the stereostructure inferred, the four amino acid residues such as the amino acid residues which correspond to the $89^{th}$ amino acid glutamine (A89Q) and the $165^{th}$ amino acid glutamic acid (A165E) as counted from the N-terminal in Chain A, and the amino acid residues which correspond to the $37^{th}$ amino acid phenylalanine (B37F) and the $48^{th}$ amino acid leucine (B48L) as counted from the N-terminal in Chain B in the nitrile hydratase stereostructure as set forth in PDB ID NO: 1IRE, (t) specifying the amino acid residues which effect a change in at least one of d1 to d3, when the shortest distance between the heavy atoms of the amino acid residue corresponding to A165E and of the amino acid residue corresponding to B48L is designated as d1; the shortest distance between the heavy atoms of the amino acid residue corresponding to A89Q and of the amino acid residue corresponding to B48L as d2; and the shortest distance between the heavy atoms of the amino acid residue corresponding to B37F and of the amino acid residue corresponding to B48L as d3, and (u) performing substitution, insertion or deletion at one or more sites of the specified amino acid residues;

[7] the method for modification according to [6], wherein the step of (t) is replaced by the following step (t'):

(t') specifying the amino acid residues which effect a change in at least one of d1 to d5, when the shortest distance between the heavy atoms of the amino acid residue corresponding to A165E and of the amino acid residue corresponding to B48L is designated as d1; the shortest distance between the heavy atoms of the amino acid residue corresponding to A89Q and of the amino acid residue corresponding to B48L as d2; the shortest distance between the heavy atoms of the amino acid residue corresponding to B37F and of the amino acid residue corresponding to B48L is designated as d3; the shortest distance between the heavy atoms of the amino acid residue corresponding to A165E and of the amino acid residue corresponding to B37F as d4; and the shortest distance between the heavy atoms of the amino acid residue corresponding to A89Q and of the amino acid residue corresponding to B37F as d5;

[8] the method for modification according to any one of [1] to [7], wherein the enzyme having the nitrile hydratase activity before modification comprises the two polypeptides [A] and [B] of the following:

[A] a polypeptide consisting of an amino acid sequence which shows homology of at least 40% with the amino acid sequence as set forth in SEQ ID NO: 98 in the Sequence Listing, and

[B] a polypeptide consisting of an amino acid sequence which shows homology of at least 25% with the amino acid sequence as set forth in SEQ ID NO: 99 in the Sequence Listing;

[9] the method for modification according to [8], wherein the polypeptide of [A] is the polypeptide of the following [C], and the polypeptide of [B] is the polypeptide of the following [D]:

[C] a polypeptide consisting of any amino acid sequence selected from the amino acid sequence as set forth in SEQ ID NO: 98 in the Sequence Listing; the amino acid sequence in which substitution, insertion or deletion has been implemented at one or more sites in the amino acid sequence as set forth in SEQ ID NO: 98 in the Sequence Listing; and the amino acid sequence in which at least one amino acid of the $6^{th}$, $19^{th}$, $38^{th}$, $77^{th}$, $90^{th}$, $102^{th}$, $106^{th}$, $126^{th}$, $130^{th}$, $142^{nd}$, $146^{th}$, $187^{th}$, $194^{th}$ and $203^{rd}$ amino acids in the amino acid sequence as set forth in SEQ ID NO: 98 in the Sequence Listing is substituted by another amino acid, and

[D] a polypeptide consisting of any amino acid sequence selected from the amino acid sequence as set forth in SEQ ID NO: 99 in the Sequence Listing; the amino acid sequence in which substitution, insertion or deletion has been implemented at one or more sites in the amino acid sequence as set forth in SEQ ID NO: 99 in the Sequence Listing; and the amino acid sequence in which at least one amino acid of the $20^{th}$, $21^{st}$, $108^{th}$, $200^{th}$ and $212^{th}$ amino acids in the amino acid sequence as set forth in SEQ ID NO: 99 in the Sequence Listing is substituted by another amino acid;

[10] the method for modification according to [8], wherein the polypeptide of [A] is the polypeptide of the following [E], and the polypeptide of [B] is the polypeptide of the following [F]:

[E] a polypeptide consisting of an amino acid sequence showing homology with the amino acid sequence which is encoded by the open reading frame (ORF) composed of from the $704^{th}$ to $1315^{th}$ of the base sequence as set forth in SEQ ID NO: 104 in the Sequence Listing, and

[F] a polypeptide consisting of an amino acid sequence showing homology with the amino acid sequence which is encoded by the ORF composed of from the $1^{st}$ to $680^{th}$ of the base sequence as set forth in SEQ ID NO: 104 in the Sequence Listing;

[11] a method for modifying an enzyme having the nitrile hydratase activity, which comprises changing one or more properties selected from the enzymatic activity, substrate specificity, $V_{max}$, $K_m$, thermal stability, stability against the substrate and stability against the product, by specifying certain amino acid residues and performing substitution, insertion or deletion at one or more sites of the specified amino acid residues according to the following procedure:

(d') aligning the amino acid sequence of the enzyme having the nitrile hydratase activity before modification, with the amino acid sequence as set forth in SEQ ID NO: 99 in the Sequence Listing, (e') specifying, based on the results of the alignment, the amino acid residues corresponding to the $48^{th}$ and $51^{st}$ in the amino acid sequence as set forth in SEQ ID NO: 99 in the Sequence Listing, and (f') performing substitution, insertion or deletion at one or more sites of the specified amino acid residues.

wherein among the two polypeptides constituting the enzyme having the nitrile hydratase activity before modification, one is the polypeptide of [E] according to [10] and the other is the polypeptide of [F] according to [10];

[12] the method for modification according to [8], wherein the polypeptide of [A] is the polypeptide of the following [G]:

[G] a polypeptide containing the region as represented by the amino acid sequence $X_1CXLC_1SC_2X_2X_3X_4X_5$ (SEQ ID NO: 142) (wherein C corresponds to cysteine, X to serine or threonine, L to leucine, $C_1$ to cysteine sulfinic acid (cysteine sulfinic acid.3-sulfinoalanine), S to serine, and $C_2$ to cysteine sulfenic acid (cysteine sulfenic acid.S-hydroxy-cysteine); and $X_1$, $X_2$, $X_3$, $X_4$ and $X_5$ represent arbitrary amino acid, respectively);

[13] the method for modification according to [12], wherein $X_1$ is valine, $X_4$ is tryptophan, and $X_5$ is proline;

[14] the method for modification according to [13], wherein $X_2$ is tyrosine and $X_3$ is proline;

[15] the method for modification according to any one of [12] to [14], wherein bonding with a metal atom is located in the region represented by $X_1CXLC_1SC_2X_2X_3X_4X_5$ (SEQ ID NO: 142);

[16] the method for modification according to [15], wherein the metal atom is a cobalt atom;

[17] a modified enzyme obtained by the method for modification according to any one of [1] to [16];

[18] a gene encoding the modified enzyme according to [17];

[19] a plasmid containing the gene according to [18];

[20] a transformant obtained by transformation of a microorganism with the gene according to [18] or the plasmid according to [19];

[21] a method for production of a modified enzyme, comprising the step of recovering a modified enzyme from a culture obtained from cultivating the transformant according to [20], the cultivated cells or a product obtained from the processing of the culture or the cultivated cells; and

[22] a method for production of an amide compound, characterized in comprising the step of bringing the modified enzyme that is obtained from a culture obtained from cultivating the transformant according to [20], the cultivated cells or a product obtained from the processing of the culture or the cultivated cells, or the method for production according to [21], into contact with a nitrile compound in a solvent to convert the nitrile compound to a corresponding amide compound.

The invention provides the amino acid sequence and the base sequence of the gene of a *Pseudonocardia thermophila*-derived nitrite hydratase which has a novel mutation point that does not change the fundamental function of nitrile hydratase. It also provides a plasmid containing the gene, a transformant containing the plasmid, a method for producing the enzyme using the transformant, and a method for processing a nitrile compound by using the transformant to produce a corresponding amide compound.

Further, the invention provides a method for modifying an enzyme having the nitrile hydratase activity before modification, by using the means characterized in changing the stereostructure of the enzyme having the nitrile hydratase activity. According to the method for modification using this means, an effect may be achieved that one or more properties selected from the enzyme activity, substrate specificity, $V_{max}$, $K_m$, thermal stability, stability against the substrate, stability against the product or the like is modified. Furthermore, the invention provides a nitrile hydratase having a novel mutation point, and a gene encoding the polypeptide chain constituting the enzyme. Also, the invention provides a plasmid containing the gene, a transformant containing the gene or the plasmid, a method for producing the enzyme using the transformant, and a method for processing a nitrile compound by using the transformant to produce a corresponding amide compound.

Figure 1:
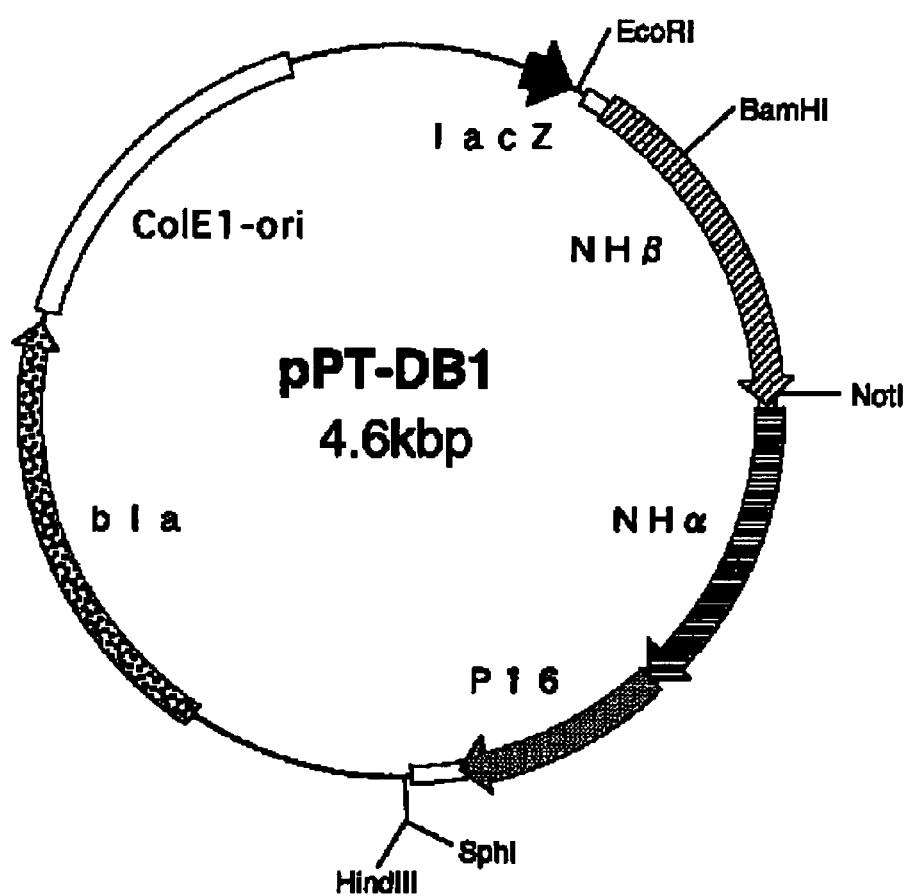
FIG. 1 shows a restriction endonuclease cleavage map of a plasmid pPT-DB1 extracted from MT10822 (Reference Example 1, Examples 1 and 83).
Figure 2:
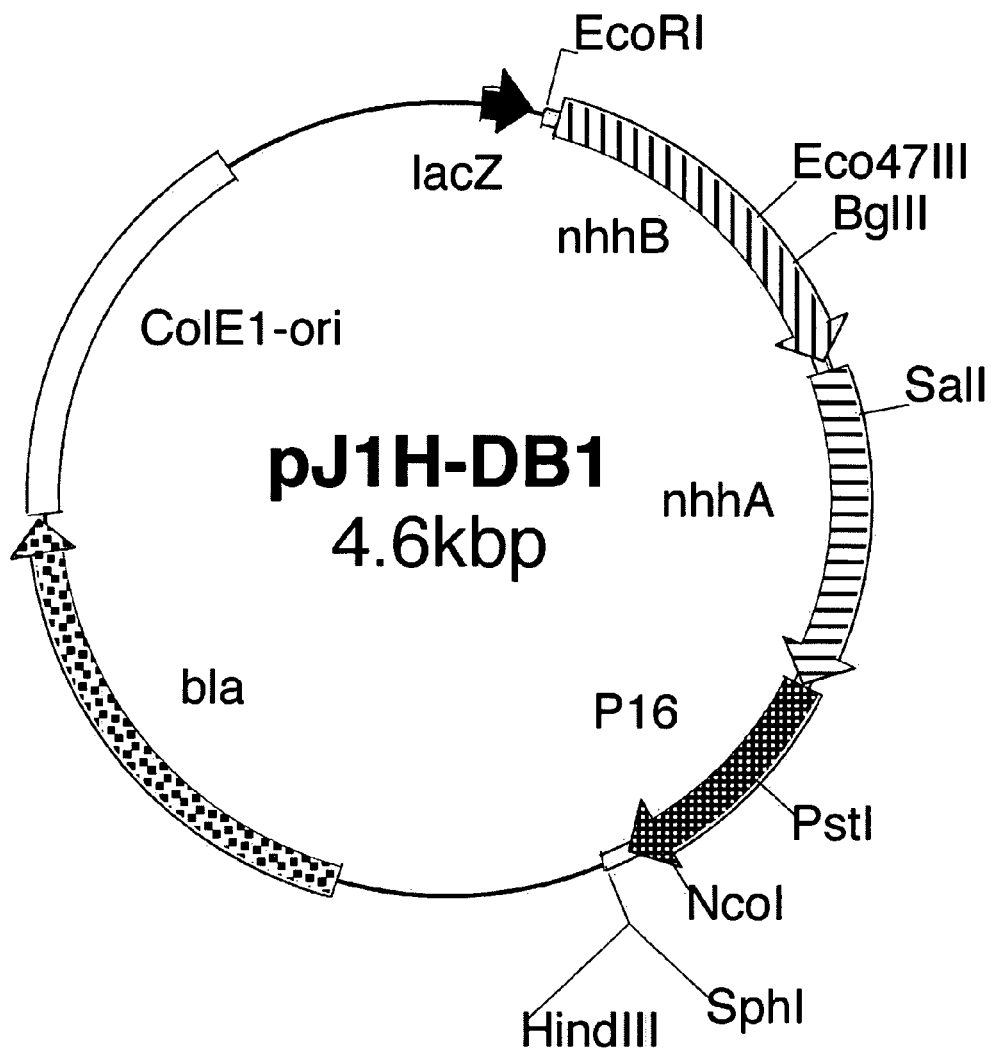
FIG. 2 shows a restriction endonuclease cleavage map of a plasmid PJ1H-DB1 constructed in order to activate and express the *Rhodococcus rhodochrous* strain J1-derived nitrile hydratase (Example 84).

The abbreviations used in FIG. 1 and FIG. 2 have the following meanings.

bla indicates the ORF encoding β-lactamase.

ColE1-ori indicates the replication-starting site in a ColE1 system.

lacZ indicates the promoter and operator region in pUC18-derived lactose operon.

NHα indicates the ORF encoding the α-subunit of *Pseudonocardia thermophila*-derived nitrile hydratase.

NHβ indicates the ORF encoding the β-subunit of *Pseudonocardia thermophila*-derived nitrile hydratase.

P16 indicates the ORF encoding a protein characterized in being involved in the activation of *Pseudonocardia thermophila*-derived nitrile hydratase.

nhhA indicates the ORF encoding the α-subunit of *Rhodococcus rhodochrous* strain J1-derived nitrile hydratase.

nhhB indicates the ORF encoding the β-subunit of *Rhodococcus rhodochrous* strain J1-derived nitrile hydratase.

BEST MODE FOR CARRYING OUT THE INVENTION

Now, the invention will be explained in more detail.

The nitrile hydratase of the invention is obtained by introducing mutation into an enzyme having the nitrile hydratase activity, and for example, it is obtained by introducing mutation into *Pseudonocardia thermophila*-derived nitrile hydratase. Specifically, such nitrile hydratase fundamentally consisted of the amino acid sequences as set forth in SEQ ID NOs: 1 and 2 in the Sequence Listing, in which amino acid at one or more predetermined sites in the amino acid sequence is substituted by another amino acid. Thus, the invention comprises a nitrile hydratase having as its constituent the α-subunit represented by the sequence of 205 amino acids as set forth in SEQ ID NO: 1 in the Sequence Listing, in which at least one amino acid in the amino acid sequence is substituted by another amino acid; a nitrile hydratase having as its constituent the β-subunit represented by the sequence of 233 amino acids as set forth in SEQ ID NO: 2 in the Sequence Listing, in which at least one amino acid in the amino acid sequence is substituted by another amino acid; and a nitrile hydratase having both of the above-mentioned substitution cases as its constituent.

According to the invention, the specific amino acid sequence-used for the nitrile hydratase obtained by introducing mutation into *Pseudonocardia thermophila*-derived nitrile hydratase, includes the following:

(a-0) the amino acid sequence of the α-subunit of SEQ ID NO: 1;

(a-1) an amino acid sequence having mutation in which at least one amino acid of the $36^{th}$, $71^{st}$, $148^{th}$ and $204^{th}$ amino acids in the amino acid sequence of the α-subunit as set forth in SEQ ID NO: 1 is substituted by another amino acid;

(a-2) an amino acid sequence having mutation in which at least one amino acid of the $6^{th}$, $19^{th}$, $38^{th}$, $77^{th}$, $90^{th}$, $102^{nd}$, $106^{th}$, $126^{th}$, $130^{th}$, $142^{nd}$, $146^{th}$, $187^{th}$, $194^{th}$ and $203^{rd}$ amino acids in the amino acid sequence of the α-subunit as set forth in SEQ ID NO: 1 is substituted by another amino acid;

(b-0) the amino acid sequence of the β-subunit as set forth in SEQ ID NO: 2 in the Sequence Listing;

(b-1) an amino acid sequence having mutation in which at least one amino acid of the $10^{th}$, $32^{nd}$, $37^{th}$, $41^{st}$, $46^{th}$, $48^{th}$, $51^{st}$, $72^{nd}$, $118^{th}$, $127^{th}$, $146^{th}$, $160^{th}$, $186^{th}$ and $217^{th}$ amino acids in the amino acid sequence of the β-subunit as set forth in SEQ ID NO: 2 is substituted by another amino acid; and (b-2) an amino acid sequence having mutation in which at least one amino acid of the $20^{th}$, $21^{st}$, $108^{th}$, $200^{th}$, and $212^{th}$ amino acids in the amino acid sequence of the β-subunit as set forth in SEQ ID NO: 2 is substituted by another amino acid.

Each of the above-mentioned mutations at least makes it possible to maintain the nitrile hydratase activity before modification.

According to the invention, the nitrile hydratase obtained by introducing mutation into *Pseudonocardia thermophila*-derived nitrile hydratase, consists of the following constituents having an amino acid sequence selected from the above (a-0) to (b-2):

(A-1) nitrile hydratase in which the α-subunit has the amino acid sequence containing the mutation of (a-1) above;

(A-2) nitrile hydratase in which the α-subunit has the amino acid sequence containing the mutations of (a-1) and (a-2) above;

(B-1) nitrile hydratase in which the β-subunit has the amino acid sequence containing the mutation of (b-1) above;

(B-2) nitrile hydratase in which the β-subunit has the amino acid sequence containing the mutations of (b-1) and (b-2) above;

(A-3) nitrile hydratase in which the α-subunit has the amino acid sequence containing the mutation of (a-1) above and the β-subunit has the amino acid sequence of (b-0) above;

(A-4) nitrile hydratase in which the α-subunit has the amino acid sequence containing the mutation of (a-1) above and the β-subunit has the amino acid sequence containing the mutation of (b-1) above;

(A-5) nitrile hydratase in which the α-subunit has the amino acid sequence containing the mutation of (a-1) above and the β-subunit has the amino acid sequence containing the mutation of (b-2) above;

(A-6) nitrite hydratase in which the α-subunit has the amino acid sequence containing the mutation of (a-1) above and the β-subunit has the amino acid sequence containing the mutations of (b-1) and (b-2) above;

(A-7) nitrite hydratase in which the α-subunit has the amino acid sequence containing the mutations of (a-1) and (a-2) above and the β-subunit has the amino acid sequence of (b-0) above;

(A-8) nitrite hydratase in which the α-subunit has the amino acid sequence containing the mutations of (a-1) and (a-2) above and the β-subunit has the amino acid sequence containing the mutation of (b-1) above;

(A-9) nitrite hydratase in which the α-subunit has the amino acid sequence containing the mutations of (a-1) and (a-2) above and the β-subunit has the amino acid sequence containing the mutation of (b-2) above;

(A-10) nitrite hydratase in which the α-subunit has the amino acid sequence containing the mutations of (a-1) and (a-2) above and the β-subunit has the amino acid sequence containing the mutations of (b-1) and (b-2) above;

(B-3) nitrite hydratase in which the α-subunit has the amino acid sequence of (a-0) above and the β-subunit has the amino acid sequence of (b-1);

(B-4) nitrite hydratase in which the α-subunit has the amino acid sequence of (a-0) above and the β-subunit has the amino acid sequence containing the mutations of (b-1) and (b-2) above; and (B-5) nitrite hydratase in which the α-subunit has the amino acid sequence containing the mutation of (a-2) above and the β-subunit has the amino acid sequence containing the mutations of (b-1) and (b-2) above.

In addition, with respect to the amino acids other than the above-mentioned specific mutation sites, substitution, insertion and deletion of amino acids may occur within the scope of not impairing the nitrile hydratase activity intended by mutation at the specific sites.

According to the invention, the nitrile hydratase gene obtained by introducing mutation into *Pseudonocardia thermophila*-derived nitrile hydratase contains the gene encoding the α-subunit of nitrile hydratase and the gene encoding the β-subunit of nitrile hydratase.

As a family of genes involved in the invention, mention may be made of those subjected to introduction of mutation into the gene of *Pseudonocardia thermophila*-derived nitrile hydratase, and they include the gene encoding the amino acid sequence of the α-subunit; the gene encoding the β-subunit; and the nitrile hydratase gene having both of the gene encoding the α-subunit and the gene encoding the β-subunit.

More specifically, the following can be mentioned.

(G-1) a gene having the base sequence that codes for the amino acid sequence having the mutation of the above-mentioned (a-1);

(G-2) a gene having the base sequence that codes for the amino acid sequence having the mutations of the above-mentioned (a-1) and (a-2);

(G-3) a gene having the base sequence that codes for the amino acid sequence having the mutation of the above-mentioned (b-1);

(G-4) a gene having the base sequence that codes for the amino acid sequence having the mutations of the above-mentioned (b-1) and (b-2); and (G-5) a gene having the base sequence that codes for any one of the nitrile hydratases of the above-mentioned (A-1) to (B-4).

As the base sequence encoding the amino acid sequence of the α-subunit of SEQ ID NO: 1 which serves as the bases for the above-mentioned mutations, the base sequence of SEQ ID NO: 3 is preferable. Also, as the base sequence encoding the amino acid sequence of the β-subunit of SEQ ID NO: 2 which serves as the bases for the above-mentioned mutations, the base sequence of SEQ ID NO: 4 is preferable.

For example, the mutation of (a-1) above which is based on SEQ ID NO: 3 can be obtained by substituting at least one base sequence among the $106^{th}$ to $108^{th}$, $211^{th}$ to $213^{th}$, $442^{nd}$ to $444^{th}$, and $610^{th}$ to $612^{th}$ of the base sequence of SEQ ID NO: 3, by another base sequence.

Further, the mutation of (a-2) above which is based on SEQ ID NO: 3 can be obtained by the substitution of a portion of the base sequence obtained by substituting at least one base sequence among the $16^{th}$ to $18^{th}$, $55^{th}$ to $57^{th}$, $112^{th}$ to $114^{th}$, $229^{th}$ to $231^{st}$, $268^{th}$ to $270^{th}$, $304^{th}$ to $306^{th}$, $316^{th}$ to $318^{th}$, $376^{th}$ to $378^{th}$, $388^{th}$ to $390^{th}$, $424^{th}$ to $426^{th}$, $436^{th}$ to $438^{th}$, $559^{th}$ to $561^{st}$, $580^{th}$ to $582^{nd}$, and $607^{th}$ to $60^{th}$ of the base sequence of SEQ ID NO: 3, by another base sequence.

Meanwhile, the mutation of (b-1) above which is based on SEQ ID NO: 4 can be obtained by the substitution of a portion of the base sequence obtained by substituting at least one base sequence among the $28^{th}$ to $30^{th}$, $94^{th}$ to $96^{th}$, $109^{th}$ to $111^{th}$, $121^{st}$ to $123^{rd}$, $136^{th}$ to $138^{th}$, $142^{nd}$ to $144^{th}$, $151^{st}$ to $153^{rd}$, $214^{th}$ to $216^{th}$, $352^{nd}$ to $354^{th}$, $379^{th}$ to $381^{st}$, $436^{th}$ to $438^{th}$, $478^{th}$ to $480^{th}$, $556^{th}$ to $558^{th}$, and $649^{th}$ to $651^{st}$ of the base sequence of SEQ ID NO: 4, by another base sequence.

Further, the mutation of (b-2) above which is based on SEQ ID NO: 4 can be obtained by the substitution of a portion of the base sequence obtained by substituting at least one base sequence among the $58^{th}$ to $60^{th}$, $61^{st}$ to $63^{rd}$, $322^{nd}$ to $324^{th}$, $598^{th}$ to $600^{th}$, and $634^{th}$ to $636^{th}$ of the base sequence of SEQ ID NO: 4, by another base sequence.

These substitutions are carried out within the scope such that the activity of the nitrile hydratase into which at least one of the α- and β-subunits encoded by the respective genes is combined and inserted, maintains or improves the state before substitution. Also, there is no particular limitation on the means for introducing mutation.

With regard to the sites other than the mutation sites of (a-1), (a-2), (b-1) and (b-2) above in the nitrile hydratase genes of the invention, they may have additional mutations involving substitution, insertion or deletion of bases, within the scope that the gene can function as the template for the protein having the nitrile hydratase activity.

Such additional mutations may be exemplified by the following. Even in the case where transcription and translation are carried out using a gene having a certain base sequence as the template, depending on conditions such as the type of the host cell incorporating the gene, the components or composition of the nutrition medium used in cultivation, the temperature or pH during cultivations or the like, modification by enzymes within the host cell after expression of the gene can lead to production of mutants in which one or two or more amino acids near the N-terminal in the Sequence Listing are deleted, or one or two or more amino acids are newly added at the N-terminal, with the intended enzymatic action being still maintained. For this reason, such mutant nitrile hydratases are also to be included in the scope of invention.

Meanwhile, the plasmid for the production of the nitrile hydratase of the invention can be prepared by using the nitrile hydratase genes. Specific examples thereof may include the following:

(P-1) a plasmid having the base sequence that codes for the amino acid sequence having the mutation of the above-mentioned (a-1);

(P-2) a plasmid having the base sequence that codes for the amino acid sequence having the mutations of the above-mentioned (a-1) and (a-2);

(P-3) a plasmid having the base sequence that codes for the amino acid sequence having the mutation of the above-mentioned (b-1)

(P-4) a plasmid having the base sequence that codes for the amino acid sequence having the mutations of the above-mentioned (b-1) and (b-2); and (P-5) a plasmid having the base sequences that code for several nitrile hydratases of the above-mentioned (A-1) to (B-4).

Furthermore, the transformant or strain of the invention is obtained by transforming an arbitrary host cell using the plasmid. The method for production of nitrile hydratase of the invention comprises a step of producing nitrile hydratase by cultivating the transformant or strain. Also, the method for production of amide compound of the invention comprises a step of bringing a culture obtained by the cultivation of such transformant or strain producing nitrile hydratase, the cultivated cells or a product obtained by processing the cultivated cells into contact with a nitrile compound in a medium to produce a corresponding amide compound.

Next, the method for modifying the enzyme having the nitrile hydratase activity of the invention will be explained in detail.

According to the invention, the nitrile hydratase activity means the activity of hydrating a nitrile compound into a corresponding amide compound. The enzyme having this activity is in general characterized in that it comprises two types of polypeptide chains called the α-subunit and the β-subunit as the constituent, and the nitrile hydratase gene refers to the two amino acid sequences having the feature of forming those two polypeptide chains or to the base sequences constituting the two ORFs having the feature of encoding the amino acid sequences.

To illustrate specifically on *Pseudonocardia thermophila* JCM3095-derived nitrile hydratase (see SEQ ID NOs: 98 and 99 in the Sequence Listing, Patent Document 3, Non-patent Document 4, and PDB ID NO: 1IRE) as an example, the polypeptide consisting of the amino acid sequence as set forth in SEQ ID NO: 98 in the Sequence Listing as well as Chain A in the stereostructure of nitrile hydratase as set forth in PDB ID NO: 1IRE is the α-subunit; and the polypeptide consisting of the amino acid sequence as set forth in SEQ ID NO: 99 in the Sequence Listing as well as Chain B in the stereostructure of nitrile hydratase as set forth in PDB ID NO: 1IRE is the β-subunit. Further, the ORF composed of the base sequence as set forth in SEQ ID NO: 100 in the Sequence Listing and the ORF composed of the base sequence as set forth in SEQ ID NO: 101 in the Sequence Listing are referred to as the nitrile hydratase gene.

In addition, in the case of *Rhodococcus rhodochrous* strain J1-derived nitrile hydratase (see SEQ ID NO: 104 in the Sequence Listing, Patent Document 2 and Non-patent Document 1), the polypeptide consisting of the amino acid sequence that is encoded by the ORF formed by the $704^{th}$ to $1315^{th}$ of the base sequence as set forth in SEQ ID NO: 104 in the Sequence Listing is the α-subunit; the polypeptide consisting of the amino acid sequence that is encoded by the ORF formed by the $1^{st}$ to $690^{th}$ of the base sequence as set forth in SEQ ID NO: 104 in the Sequence Listing is the β-subunit; and the two ORFs encoded by the base sequence as set forth in SEQ ID NO: 104 in the Sequence Listing are the nitrile hydratase gene.

The method for modification as used in the invention means a method directed to changing the stereostructure of an enzyme having the nitrile hydratase activity before modification for the purpose of changing one or more properties among the enzymatic activity, substrate specificity, $V_{max}$, $K_m$, thermal stability, stability against the substrate and stability against the product, without impairing the original nitrile hydratase activity. As the feature of the method, it can be mentioned that the method comprises a step of specifying, based on an interpretation of the stereostructure, the region forming a cavity through which a substrate passes from the outside of the enzyme toward the active center or a product passes from the active center toward the outside of the enzyme, and/or the region forming an associative interface between the α-subunit and the β-subunit which is involved in the formation of dimers or an interface which is involved in the association of dimers, and applying alterations such as substitution, insertion or deletion at one or more amino acids in the amino acid sequence which correspond to the amino acid residues that are present in the regions.

To illustrate specifically on *Pseudonocardia thermophila* JCM3095-derived nitrile hydratase (see SEQ ID NOs: 98 and 99 in the Sequence Listing, Patent Document 3, Non-patent Document 4, and PDB ID NO: 1IRE) as an example, for the amino acid residues corresponding to those present in the region forming a cavity through which a substrate passes from the outside of the enzyme toward the active center or a product passes from the active center toward the outside of the enzyme, mention may be made of the amino acid residues forming the region that corresponds to the $1^{st}$ helix and $2^{nd}$ helix as counted from the N-terminal of Chain B and the loop portions inserted in the helices in the nitrile hydratase stereostructure as set forth in PDB ID NO: 1IRE; the amino acid residues whose side-chain front-end heavy atoms are located within 5 Å of radius in the respective stereostructures having as the point center, each of the side-chain front-end heavy atoms of the four amino acid residues which correspond to the $89^{th}$ amino acid residue glutamine and the $165^{th}$ amino acid residue glutamic acid as counted from the N-terminal of Chain A, and to the $37^{th}$ amino acid residue phenylalanine and the $48^{th}$ amino acid residue leucine as counted from the N-terminal of Chain B in the nitrile hydratase stereostructure as set forth in PDB ID NO: 1IRE; the amino acid residues corresponding to the region extending from the $36^{th}$ threonine to $48^{th}$ asparagine of the amino acid sequence as set forth in SEQ ID NO: 98 in the Sequence Listing, to the region extending from the $31^{st}$ lysine to the $51^{st}$ phenylalanine and to the region extending from the $112^{th}$ lysine to $127^{th}$ leucine of the amino acid sequence as set forth in SEQ ID NO: 99 in the Sequence Listing; and the amino acid residues corresponding to the $37^{th}$, $40^{th}$, $41^{st}$, $46^{th}$, $48^{th}$, $51^{st}$, $61^{st}$, $72^{nd}$, $112^{th}$, $118^{th}$ and $127^{th}$ of the amino acid sequence as set forth in SEQ ID NO: 99 in the Sequence Listing; or the like.

Furthermore, for the amino acid residues corresponding to those present in the region forming an associative interface between the α-subunit and the β-subunit which is involved in the formation of dimers or an interface which is involved in the association of dimers, mention may be made of the amino acid residues corresponding to the $2^{nd}$ helix as counted from the N-terminal of Chain A and the $2^{nd}$ helix as counted from the N-terminal of Chain B in the nitrile hydratase stereostructure as set forth in PDB ID NO: 1IRE, to the region extending from the $36^{th}$ threonine to the $48^{th}$ asparagine of the amino acid sequence as set forth in SEQ ID NO: 98 in the Sequence Listing, and to the region extending from the $112^{th}$ lysine to the $127^{th}$ leucine of the amino acid sequence as set forth in SEQ ID NO: 99 in the Sequence Listing; the amino acid residues corresponding to the $36^{th}$, $71^{st}$, $148^{th}$, $188^{th}$ and $204^{th}$ of the amino acid sequence as set forth in SEQ ID NO: 98 in the Sequence Listing; the amino acid residues corresponding to the $10^{th}$, $32^{nd}$, $33^{rd}$, $112^{th}$, $118^{th}$, $127^{th}$, $146^{th}$, $150^{th}$, $160^{th}$, $168^{th}$, $171^{st}$, $176^{th}$, $186^{th}$, $217^{th}$ and $218^{th}$ of the amino acid sequence as set forth in SEQ ID NO: 99 in the Sequence Listing; or the like.

In addition, as the method for specifying, among the amino acid residues constituting the region that forms a cavity through which a substrate passes from the outside of the enzyme toward the active center or a product passes from the active center toward the outside of the enzyme, the amino acid residues whose alteration leads to a change in the cavity size and further controls the easiness or difficulty in passing of the substrate/product, mention may be made of a method for specifying the four amino acid residues which correspond to the $89^{th}$ amino acid glutamine (A89Q) and the $165^{th}$ amino acid glutamic acid (A165E) as counted from the N-terminal of Chain A, and to the $37^{th}$ amino acid phenylalanine (B37F) and the $48^{th}$ amino acid leucine (B48L) as counted from the N-terminal of Chain B in the nitrile hydratase stereostructure as set forth in PDB ID NO: 1IRE; a method for specifying the amino acid residues which effect a change in at least one of d1 to d5, when the shortest distance between the heavy atoms of the amino acid residue corresponding to A165E and of the amino acid residue corresponding to B48L is designated as d1; the shortest distance between the heavy atoms of the amino acid residue corresponding to A89Q and of the amino acid residue corresponding to B48L as d2; the shortest distance between the heavy atoms of the amino acid residue corresponding to B37F and of the amino acid residue corresponding to B48L is designated as d3; the shortest distance between the heavy atoms of the amino acid residue corresponding to A165E and of the amino acid residue corresponding to B37F as d4; and the shortest distance between the heavy atoms of the amino acid residue corresponding to A89Q and of the amino acid residue corresponding to B37F as d5; a method for specifying the amino acid residues which effect a change in at least one of the above-described d1 to d5, or for specifying the amino acid residues which effect a change in at least one of the above-described d1 to d3; or the like.

Therefore, the invention includes any method for modification, comprising a step of applying alterations such as substitution, insertion or deletion at amino acids in the amino acid sequence which correspond to at least one amino acid residues as specified in the above-described manner in a subject nitrile hydratase (*Pseudonocardia thermophila* JCM3095-derived one may be mentioned as a representative example).

Furthermore, the invention also includes the method for modification by aligning a nitrile hydratase (for example, a *Rhodococcus rhodochrous* strain J1-derived nitrile hydratase) derived from a biological species other than *Pseudonocardia thermophila* JCM3095 with the stereostructure or the amino acid sequence of *Pseudonocardia thermophila* JCM3095-derived nitrile hydratase, finding the amino acid residues corresponding to the above-mentioned amino acid residues and altering the amino acids in the corresponding amino acid sequences.

In carrying out the subject matters described above, the means used to implementing alignment based on the stereostructure or amino acid sequence is not particularly limited. However, as exemplary means for the alignment of amino acid sequence, software for genomic sequence interpretation such as DNASIS (manufactured by Hitachi Software Engineering Co., Ltd.) or a free software ClustalW or BLAST may be mentioned; and as exemplary means for the modeling of stereostructure based on the amino acid sequence alignment, software for predicting protein stereostructure such as Modeler and Homology (products by Accelrys Software, Inc.) may be mentioned.

Speaking of an example, in the case of a *Rhodococcus rhodochrous* strain J1-derived nitrile hydratase (see SEQ ID NO: 104 in the Sequence Listing, Patent Document 2 and Non-patent Document 1), the results of alignment show that the amino acid residue corresponding to the amino acid residue: Leu which corresponds to the $48^{th}$ of the amino acid sequence as set forth in SEQ ID NO: 99 in the Sequence Listing is the amino acid residue: Trp corresponding to the $48^{th}$ of the amino acid sequence which is encoded by the ORF formed by the $1^{st}$ to $690^{th}$ of the base sequence as set forth in SEQ ID NO: 104 in the Sequence Listing; and the amino acid residue corresponding to the amino acid residue: Phe which corresponds to the $51^{st}$ of the amino acid sequence as set forth in SEQ ID NO: 99 in the Sequence Listing is the amino acid residue: Ser corresponding to the $51^{st}$ of the amino acid sequence which is encoded by the ORF formed by the $1^{st}$ to $690^{th}$ of the base sequence as set forth in SEQ ID NO: 104 in the Sequence Listing. The results are consistent with the alignment results based on amino acid sequence and the alignment results based on stereostructure. The invention also includes the method for modification by altering any one or both of the amino acids in the amino acid sequence which corresponds to these two amino acid residues.

Moreover, in carrying out the above-described method for modification, the means for introducing mutation to alter amino acids in the amino acid sequence corresponding to amino acid residues is not particularly limited. But, an example may include a method for introducing mutation of substituting an amino acid in the amino acid sequence with another amino acid by means of recombinant gene technology.

Furthermore, with respect to any changes in the amino acid sequence or base sequence resulting from a mutation additionally introduced in addition to the intentionally introduced mutation, substitution, insertion or deletion of an amino acid or a base may occur within the scope of not impairing the desired nitrile hydratase activity achieved by the intended introduction of mutation.

Such additionally introduced mutation may be exemplified by the following. Even in the case where transcription and translation are carried out using a gene having a certain base sequence as the template, depending on conditions such as the type of the host cell incorporating the gene, the components or composition of the nutrition medium used in cultivation, the temperature or pH during cultivation, or the like, modification by enzymes inside the host cell after expression of the gene can lead to production of mutants in which one or two or more amino acids near the N-terminal in the Sequence Listing are deleted, or one or two or, more amino acids are newly added at the N-terminal, with the initial enzymatic action being still maintained. For this reason, such method for modification resulting in mutant nitrile hydratases is also to be included in the scope of invention.

As exemplary nitrile hydratases before modification which serve as the subject for the method for modification according to the invention, a *Rhodococcus rhodochrous* strain J1-derived nitrile hydratase and a *Pseudonocardia thermophila* JCM3095-derived nitrile hydratase may be mentioned. More specifically, mention may be made of a nitrile hydratase comprising as its constituents the polypeptide chain formed by an amino acid sequence which is homologous to the amino acid sequence encoded by the ORF which is formed by the $1^{st}$ to $690^{th}$ of the base sequence as set forth in SEQ ID NO: 104 in the Sequence Listing and the polypeptide chain formed by an amino acid sequence which is homologous to the amino acid sequence encoded by the ORF which is formed by the $704^{th}$ to $1315^{th}$ of the base sequence as set forth in SEQ ID NO: 104 in the Sequence Listing; a nitrile hydratase comprising as its constituents the polypeptide chain formed from the amino acid sequence as set forth in SEQ ID NO: 98 in the Sequence Listing and the polypeptide chain formed from the amino acid sequence as set forth in SEQ ID NO: 99 in the Sequence Listing.

The nitrile hydratase before modification which serve as the subject for the method for modification according to the invention may also include a nitrile hydratase comprising as its constituents the polypeptide formed from an amino acid sequence which shows homology of 40% or greater with the amino acid sequence as set forth in SEQ ID NO: 98 in the Sequence Listing and the polypeptide formed from an amino acid sequence which shows homology of 25% or greater with the amino acid sequence as set forth in SEQ ID NO: 99 in the Sequence Listing.

Examples of the polypeptide formed from an amino acid sequence which shows homology of 40% or greater with the amino acid sequence as set forth in SEQ ID NO: 98 in the Sequence Listing may include the polypeptide formed from the amino acid sequence as set forth in SEQ ID NO: 98 in the Sequence Listing; the polypeptide formed from an amino acid sequence in which arbitrary alteration such as substitution, insertion or deletion is applied to at least one site of the amino acid sequence as set forth in SEQ ID NO: 98; the polypeptide formed from an amino acid sequence in which at least one amino acid selected from the $6^{th}$, $19^{th}$, $38^{th}$, $77^{th}$, $90^{th}$, $102^{nd}$, $106^{th}$, $126^{th}$, $130^{th}$, $142^{nd}$, $146^{th}$, $187^{th}$, $194^{th}$ and $203^{rd}$ amino acids in the amino acid sequence as set forth in SEQ ID NO: 98 in the Sequence Listing is substituted by another amino acid; the polypeptide formed from an amino acid sequence that is homologous to the amino acid sequence encoded by the ORF which is formed by the $704^{th}$ to $1315^{th}$ of the base sequence as set forth in SEQ ID NO: 104 in the Sequence Listing; or the like.

Further, the polypeptide formed from an amino acid sequence which shows homology of 40% or greater with the amino acid sequence as set forth in SEQ ID NO: 98 in the Sequence Listing is characterized, in some cases, in that it is a polypeptide containing a region represented by $X_1CXLC_1SC_2X_2X_3X_4X_5$ (SEQ ID NO: 142) (wherein C corresponds to cysteine, X to serine or threonine, L to leucine, $C_1$ to cysteine sulfinic acid (cysteine sulfinic acid·3-sulfinoalanine), S to serine, and $C_2$ to cysteine sulfenic acid (cysteine sulfenic acid.S-hydroxy-cysteine); and $X_1$, $X_2$, $X_3$, $X_4$ and $X_5$ represent arbitrary amino acid, respectively) in the sequence. Additionally, the polypeptide is also characterized, in some cases, in that $X_1$ is valine, $X_4$ is tryptophan, and $X_5$ is proline. Again, the polypeptide is also characterized, in some cases, in that $X_2$ is tyrosine and $X_3$ is proline.

In the above-mentioned cases, the polypeptide is in some cases characterized in being bonded to a metal atom via the region represented by $X_1CXLC_1SC_2X_2X_3X_4X_5$ (SEQ ID NO: 142). In addition, this metal is in some cases characterized in being cobalt.

Examples of the polypeptide formed from an amino acid sequence which shows homology of 25% or greater with the amino acid sequence as set forth in SEQ ID NO: 99 in the Sequence Listing may include the polypeptide formed from the amino acid sequence as set forth in SEQ ID NO: 99 in the Sequence Listing; the polypeptide formed from an amino acid sequence in which arbitrary alteration such as substitution, insertion or deletion is applied to at least one site of the amino acid sequence as set forth in SEQ ID NO: 99 in the Sequence Listing; the polypeptide formed from an amino acid sequence in which at least one amino acid selected from the $20^{th}$, $21^{st}$, $108^{th}$, $200^{th}$ and $212^{th}$ amino acids in the amino acid sequence as set forth in SEQ ID NO: 99 in the Sequence Listing is substituted by another amino acid; the polypeptide formed from an amino acid sequence that is homologous to the amino acid sequence encoded by the ORF which is formed by the $1^{st}$ to $690^{th}$ of the base sequence as set forth in SEQ ID NO: 104 in the Sequence Listing; or the like.

Speaking of an example, in the case of *Rhodococcus rhodochrous* strain J1-derived nitrile hydratase, since it is a nitrile hydratase comprising as its constituents the polypeptide formed from the amino acid sequence that is encoded by the ORF which is formed by the $704^{th}$ to $1315^{th}$ of the base sequence as set forth in SEQ ID NO: 104 in the Sequence Listing, and the polypeptide formed from the amino acid sequence that is encoded by the ORF which is formed by the $1^{st}$ to $690^{th}$ of the base sequence as set forth in SEQ ID NO: 104 in the Sequence Listing, it is included in the scope of nitrile hydratase before modification, which is the subject of the method for modification according to the invention.

Also, since *Pseudonocardia thermophila* JCM3095-derived nitrile hydratase is a nitrile hydratase comprising as its constituents the polypeptide formed from the amino acid sequence as set forth in SEQ ID NO: 98 in the Sequence Listing and the polypeptide formed from the amino acid sequence as set forth in SEQ ID NO: 99 in the Sequence Listing, it is also included in the scope of nitrile hydratase before modification, which is the subject of the method for modification according to the invention.

Furthermore, as an example of the nitrile hydratase derived from *Pseudonocardia thermophila* JCM3095-derived nitrile hydratase, mention may be made of a nitrile hydratase satisfying any one or both in the cases of a nitrile hydratase in which, among the constituents of *Pseudonocardia thermophila* JCM3095-derived nitrile hydratase, the polypeptide formed from the amino acid sequence as set forth in SEQ ID NO: 98 in the Sequence Listing is replaced by the polypeptide formed from an amino acid sequence in which arbitrary alteration such as substitution, insertion or deletion is applied to at least one site of the amino acid sequence as set forth in SEQ ID NO: 98 in the Sequence Listing, or by the polypeptide formed from an amino acid sequence in which at least one amino acid of the $6^{th}$, $19^{th}$, $38^{th}$, $77^{th}$, $90^{th}$, $102^{nd}$, $106^{th}$, $126^{th}$, $130^{th}$, $142^{nd}$, $146^{th}$, $187^{th}$, $194^{th}$ and $203^{rd}$ amino acids in the amino acid sequence as set forth in SEQ ID NO: 98 in the Sequence Listing is substituted by another amino acid; and a nitrile hydratase in which the polypeptide formed from the amino acid sequence as set forth in SEQ ID NO: 99 in the Sequence Listing is replaced by the polypeptide formed from an amino acid sequence in which arbitrary alteration such as substitution, insertion or deletion is applied to at least one site of the amino acid sequence as set forth in SEQ ID NO: 99 in the Sequence Listing, or by the polypeptide formed from an amino acid sequence in which at least one amino acid of the $20^{th}$, $21^{st}$, $108^{th}$, $200^{th}$ and $212^{th}$ amino acids in the amino acid sequence as set forth in SEQ ID NO: 99 in the Sequence Listing is substituted by another amino acid.

A nitrile hydratase derived from *Pseudonocardia thermophila* JCM3095-derived nitrile hydratase is also included in the scope of nitrile hydratase before modification, which is the subject of the method for modification according to the invention.

According to the invention, a modified enzyme means a nitrile hydratase obtained by carrying out the method for modification using an enzyme having the nitrile hydratase activity as the subject of the method. An example thereof may include a modified enzyme characterized in being obtained by changing the character of a nitrile hydratase before modification by using the above-described methods for modification.

For the change of characters, as compared with a nitrile hydratase before modification, mention may be made of change in one or more properties such as the substrate specificity, $V_{max}$, $K_m$, thermal stability, stability against the substrate (for example, an arbitrary nitrile compound which can be converted to a corresponding amide compound upon the action of the enzyme as a catalyst), stability against the product (for example, the corresponding amide compound obtained by converting an arbitrary nitrile compound upon the action of the enzyme as a catalyst) or the like. Specific examples may include the following:

(1) It becomes easy to take a nitrile compound with relatively larger bulkiness as the substrate.

(2) It becomes easy to take a nitrile compound with relatively smaller bulkiness as the substrate (3) $V_{max}$ in the case of taking an arbitrary nitrile compound as the substrate, increases (4) $K_m$ in the case of taking an arbitrary nitrile compound as the substrate, decreases.

(5) The rate of irreversible deactivation in the case of exposing the enzyme to an arbitrary amount of heat, decreases.

(6) The rate of irreversible deactivation in the case of exposing the enzyme to the substrate at an arbitrary concentration, decreases.

(7) The rate of reaction inhibition due to the presence of the product at an arbitrary concentration during the reaction, decreases.

(8) The rate of irreversible deactivation in the case of exposing the enzyme to the product at an arbitrary concentration, decreases, or the like.

As an index for the change of character resulting from carrying out the method for modification on a nitrile hydratase before modification according to the invention, the change in the substrate specificity may be mentioned as one representative example. When a modified enzyme as obtained according to the method for modifying the invention is one that has undergone a change in the substrate specificity, the modified enzyme is included in the scope of modified enzyme according to the invention.

As the method for observing the change in substrate specificity of thus obtained modified enzyme, mention may be made of a method of carrying out the reaction using a plurality of nitrile compounds of different bulkiness as the substrate and determining the difference in the quantities of the produced corresponding amide compounds. As an example thereof, the reaction is carried out, on the one hand, using acrylonitrile as the substrate to produce acrylamide, and on the other hand, using methacrylonitrile as the substrate to produce methacrylamide, and the molar ratio of the two products may be compared. In this case, a modified enzyme which results in a change such that the value of [moles of produced methacrylamide]÷[moles of produced acrylamide] has increased as compared with the value obtained by an enzyme before modification, can be said to have undergone a change in character to facilitate the reaction using a nitrile compound with larger bulkiness as the substrate. Similarly, a modified enzyme which results in a change such that the value has decreased, can be said to have undergone a change in character to facilitate the reaction using a nitrile compound with smaller bulkiness as the substrate.

In an exemplary study with *Pseudonocardia thermophila* JCM3095-derived nitrile hydratase and a nitrile hydratase derived from *Pseudonocardia thermophila* JCM3095-derived nitrile hydratase, when the process for modification is carried out comprising the step of specifying, according to the interpretation of stereostructure, the region forming a cavity through which a substrate passes from the outside of the enzyme toward the active center or a product passes from the active center toward the outside of the enzyme, and/or the region forming an associative interface between the α-subunit and the β-subunit which is involved in the formation of dimers or an interface which is involved in the association of dimers, and applying alterations such as substitution, insertion or deletion at one or more amino acids in the amino acid sequence which correspond to the amino acid residues present in these regions, a modified enzyme which has undergone a change in the molar ratio between acrylamide produced from the reaction using acrylonitrile as the substrate and methacrylamide produced from the reaction using methacrylonitrile as the substrate, as compared with an enzyme before modification, could be obtained. Since this can be viewed as a change in substrate specificity, that is, a change of characters, the modified enzyme as obtained above is included in the scope of modified enzyme according to the invention.

In a study with *Rhodococcus rhodochrous* strain J1-derived nitrile hydratase, when the process for modification was carried out by altering the amino acid residue: Trp which corresponds to the 48$^{th}$ of the amino acid sequence encoded by the ORF that is formed by the 1$^{st}$ to 690$^{th}$ of the base sequence as set forth in SEQ ID NO: 104 in the Sequence Listing to another amino acid residue, the enzyme showed a change in character to facilitate the reaction using a nitrile compound with larger bulkiness as the substrate, as compared with the subject before modification. Thus, the protein showing the change of character as achieved as such is included in the scope of modified enzyme according to the invention.

Furthermore, it can be easily deduced that combining the mutation sites of a modified enzyme thus obtained will lead to an additional change of character. Accordingly, a modified enzyme obtained by such combining of mutation sites is also included in the scope of modified enzyme according to the invention.

According to the invention, the gene encoding a modified enzyme means the two amino acid sequences having the feature of forming the two types of polypeptide chains which constitute the modified enzyme, or the base sequences forming the two ORFs having the feature of encoding the amino acid sequences.

According to the invention, the plasmid having the feature of containing the gene means the plasmid having the feature of containing in its sequence, the base sequences forming the two ORFs which have the feature of encoding the two amino acid sequences that are characterized in forming the two polypeptide chains constituting the modified enzyme.

The plasmid can have, in addition to the gene according to the invention, a constitution which enables the production of a modified enzyme by means of a transformant or a strain obtained by transforming an arbitrary host cell, such as the regulatory region necessary for the expression of each gene, the region necessary for autonomous replication or the like. The arbitrary host cell as used herein may be exemplified by *Escherichia coli* as used in an embodiment of the below-described Examples, though not intended to be limited to this. Use can be also made of other microorganisms such as *Bacillus* species such as *Bacillus subtilis*, yeast or *Streptomyces* species.

The regulatory region necessary for expression may include a promoter sequence (including the transcription-regulating operator sequence), a ribosome binding sequence (SD sequence), a transcription-terminating sequence and the like.

Specific examples of the promoter sequence may include the trp promoter of *E. coli*-derived tryptophan operon, the lac promoter of lactose operon, the lambda-phage-derived PL promoter and PR promoter, or the *B. subtilis*-derived gluconic acid synthetase promoter (gnt), the alkali protease promoter (apr), the neutral protease promoter (npr), the α-amylase promoter (amy) and the like. Further, artificially designed or improved sequences such as the tac promoter or trc promoter can be also used.

The ribosome binding sequence may be exemplified by the *E. coli*-derived sequence, *B. subtilis*-derived sequence or the original sequences of *Rhodococcus* or *Pseudonocardia*, but it is not particularly limited as long as it works in a desired host cell such as *E. coli* or *B. subtilis*. For example, a consensus sequence comprising a series of 4 or more consecutive bases that are complementary to the 3'-terminal region of 16S ribosome RNA can be prepared by DNA synthesis and used. The transcription-terminating sequence is not essentially required, but one that is not ρ factor-dependent, for example, lipoprotein terminator, trp operon terminator or the like may be used. The sequence order of these regulatory regions on a plasmid is preferably such that the promoter sequence and the ribosome binding sequence are located further upstream to the 5'-terminal than the gene according to the invention, and the transcription-terminating sequence is preferably located further downstream to the 3'-terminal than the gene according to the invention. Also, the base sequences respectively encoding the ORFs which constitute the gene according to the invention may be expressed as individual independent cistrons by means of such regulatory regions, or may be expressed as a polycistron by means of a common regulatory region.

Examples of the plasmid vector satisfying the above requirements may include pBR322, pUC18, pBluescript, pKK223-3 and pSC101, which have a region capable of autonomous replication in *E. coli*, or pUB110, pTZ4, pC194, ρ 11, φ 1 and φ 105 which have a region capable of autonomous replication in *B. subtilis*, and the like. Further, examples of the plasmid vector capable of autonomous replication in two or more species of host cells may include pHV14, TRp7, YEp7 and pBS7.

When a nitrile hydratase having the desired activity to express the gene according to the invention is produced, a protein involved in the activation of nitrile hydratase may be required in some cases.

A protein involved in the activation of nitrile hydratase is a protein having the property such that the presence or absence of the expression of the protein directly controls the activation of nitrile hydratase, and it can be exemplified by the protein involved in the activation of *Pseudonocardia thermophila*-derived nitrile hydratase (nitrile hydratase-activating protein) as described in Patent Document 4. More specifically, the nitrile hydratase-activating protein may be exemplified by one constituted by the sequence of 144 amino acids as presented in the amino acid sequence of SEQ ID NO: 102. Also, the mutant proteins obtained by substitution, insertion or deletion of amino acids in part of the amino acid sequence of SEQ ID NO: 102 are to be included in the nitrile hydratase-activating protein, as long as they are involved in the activation of nitrile hydratase. For such mutant proteins, mention may be made of those having mutation such as substitution, insertion or deletion of one or more amino acids with respect to the amino acid sequence of SEQ ID NO: 102 and maintaining the property involved in the activation of nitrile hydratase.

The gene encoding the nitrile hydratase-activating protein is not particularly limited as long as it is a gene that codes for the nitrile hydratase-activating protein. Such gene may be exemplified by the gene having the base sequence which codes for the amino acid sequence of SEQ ID NO: 102 and the genes that code for the mutant proteins. Further, as a preferred example of the gene encoding the nitrile hydratase-activating protein, the gene having the base sequence of SEQ ID NO: 103 may be mentioned. Also, if a gene encoding the nitrile hydratase-activating protein functions as the gene encoding the nitrile hydratase-activating protein, even though it is a sequence having substitution, insertion or deletion of one or two or more bases with respect to the base sequence as set forth in SEQ ID NO: 103, then the gene is to be included in the scope of genes encoding the nitrile hydratase-activating protein.

As an example of the case of using the gene encoding the nitrile hydratase-activating protein, mention may be made of one in which the ORF of the gene is included into the plasmid of the invention together with the two ORFs forming the gene according to the invention. In this case, the order of these ORFs on the plasmid is not particularly limited. Also, three ORFs may be regulated by the same regulatory region; two of the ORFs may be regulated by the same regulatory region, the other one of the ORFs being regulated by a regulatory region different from the former; or the three ORFs may be each regulated by different regulatory regions.

For a method of constructing the plasmid of the invention by inserting the gene according to the invention into such vector plasmid, together with those regions necessary for expression of the activity of the modified enzyme according to the invention, or a method of transforming a desired host cell using the plasmid and a method of producing nitrile hydratase in the transformant, use can be made of those general methods and host cells known in the art of molecular biology, biological engineering and genetic engineering as described in, for example, "Molecular Cloning, $3^{rd}$ ed." (J. Sambrook et al., Cold Spring Harbor Laboratory Press, 2001) or the like.

According to the invention, the transformant characterized in being obtained by transformation includes those obtained by transforming a host cell using the gene or plasmid according to the invention. As an example of cultivating the transformant, a method of inoculating the transformant in a culture medium and then incubating it at a suitable cultivating temperature (in general, 20° C. to 50° C.) may be mentioned.

Further, when the host cell is a microorganism, LB medium, M9 medium or the like is generally used as the culture medium for cultivating the transformant, and metal ions may be added to such medium. The metal ion to be added may be Fe ion and Co ion. The amount of addition may be, for example, 0.1 μg/mL or greater.

For the method for producing a modified enzyme characterized in comprising a step of recovering a modified enzyme from a culture obtained by cultivating the transformant, the cultivated cells, or a product of processing the culture or cells according to the invention, mention may be made of one comprising a step of recovering the nitrile hydratase activity from the transformant, a culture of the transformant, or a product of processing the transformant or the culture.

For the method for producing an amide compound characterized in comprising a step of converting a nitrile compound to a corresponding amide compound according to the invention, mention may be made of one comprising a step of using as the catalyst the nitrile hydratase activity recovered from the transformant, a culture of the transformant, or a product of processing the transformant or the culture, or according to the above-mentioned method for production, to convert a nitrile compound to a corresponding amide compound.

As an example of the method of using the modified enzyme according to the invention or a transformant having the enzyme activity to process a nitrile compound to produce a corresponding amide compound, mention may be made of a method comprising a step of bringing the desired nitrile compound into contact with a purification product or a crude enzyme product of the enzyme, with a culture for the transformant according to the invention, with a transformant obtained from the culture, or with a product of processing the transformant, in a solvent. The product of processing as used herein includes an extract or a disruption product of the transformant, a post-separation product such as a crude enzyme product obtained by isolating the nitrile hydratase activated fraction from such extract or disruption product, an enzyme purification product obtained by further purification or the like; and an immobilization product in which the transformant, or an extract, a disruption product or a post-separation product of the transformant is immobilized by suitable means. The contact temperature is not particularly limited, but it is preferably in the temperature range of not deactivating the nitrile hydratase, and more preferably from the freezing point or higher to 60° C. or lower.

As the nitrile compound, there is no particular limitation as long as it is a compound which can act as the substrate for the modified enzyme of the invention, and examples may include nitrile compounds having 2 to 4 carbon atoms, such as acetonitrile, propionitrile, acrylonitrile, methacrylonitrile, n-butyronitrile, isobutyronitrile, crotononitrile, α-hydroxyisobutyronitrile and the like. The concentration of such nitrile compound in the solvent is not particularly limited. The reaction temperature is, though not particularly limited, preferably in the range of not deactivating the nitrile hydratase, and more preferably from the freezing point or higher to 50° C. or lower.

Examples as described below will illustrate the invention in more detail, but they are not intended to limit the invention in any way. Also, the HPLC analysis in each Example and Comparative Example was carried out using Finepak SIL C18-5 (250×4.6 φ mm; product by JASCO) as the column and a 10 mM aqueous solution of phosphoric acid containing 4 vol % of acetonitrile as the eluent. In addition, acrylamide, acrylonitrile, acrylic acid, methacrylamide, methacrylonitrile and methacrylic acid were detected by absorbance at 210 nm.

EXAMPLES

Reference Example 1

Construction (1) of the Substituted Amino Acid Having Nitrile Hydratase Activity For the substitution with Met for the $6^{th}$ Leu in the α-subunit, introduction of site-specific mutation was performed using a "LA PCR in vitro mutagenesis Kit" (manufactured by Takara Shuzo Co., Ltd.). Hereinafter, the "LA PCR in vitro mutagenesis Kit" is simply referred to as the kit. In following Reference Examples, the kit was handled on the basis of the principle thereof and in accordance with the manufacturer's instructions for the kit.

10 ml of a liquid LB medium was put into a 30 ml test tube, and sterilized by autoclaving at 121° C. for 20 minutes. Ampicillin was added to this medium to have a final concentration of 100 μg/ml. On the medium, one platinum loop of the cells of MT-10822 were inoculated and incubated therein at 37° C. for about 20 hours with stirring at 300 rpm. 1 ml of the resulting culture was put into a suitable centrifugal tube, and this was subjected to centrifugation (15,000 rpm, 5 minutes) to separate the cells from the culture. The plasmid pPT-DB1 was prepared from the cells by alkaline SDS extraction.

Using 10 ng of pPT-DB1 as the template, PCRs of two different types were carried out. For the PCR reaction No. 1, a reaction system of 50 μl in total comprising 50 pmols of the primer having the sequence as forth in SEQ ID No: 7 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out. This assay revealed the production of the amplified DNA products in the both PCR reactions. From each of these PCR reaction mixtures, the excess primers and dNTP were removed using Microcon 100 (manufactured by Takara Shuzo Co., Ltd.), and then TE was added to each of the mixtures to prepare 50 µl each of TE solutions. An annealing solution of 47.5 µl in total containing 0.5 µl of both of the above TE solutions (for the composition of the system, the manufacturer's instructions for the kit were followed) was prepared, and this solution was subjected to annealing by performing thermal denaturation of the solution at 98° C. for 10 minutes, subsequently cooling the solution to 37° C. at a constant cooling rate over a period of 60 minutes, and then maintaining it at 37° C. for 15 minutes. To thus annealed solution, 0.5 µl of TaKaRa LA Taq was added, and the solution was heated at 72° C. for 3 minutes, thus completing the formation of heterologous double-stranded DNA. This was then subjected to PCR reaction No. 3. For the PCR reaction No. 3, a reaction system of 50 µl in total comprising 50 pmols of an M13 primer M4 (having the sequence as forth in SEQ ID No: 8 in the Sequence Listing) and 50 pmols of an M13 primer RV (having the sequence as forth in SEQ ID No: 10 in the Sequence Listing) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. After completion of the PCR reaction No. 3, 5 µl of the reaction mixture was subjected to agarose gel electrophoresis (using Type VII low-melting-point agarose, a product by Sigma Corporation; agarose concentration of 0.8% by weight), and an assay of the DNA amplification product was carried out, thereby it being possible to confirm the presence of an amplified DNA product of about 2 kbp. Subsequently, an agarose fragment comprising only a DNA fragment of about 2 kbp was cut out of the agarose gel. The thus-cut agarose fragment (about 0.1 g) was finely pulverized, suspended in 1 ml of a TE solution, and kept at 55° C. for 1 hour, whereby the agarose fragment was completely melted. The resulting agarose melt was then subjected to phenol/chloroform extraction and ethanol precipitation to purify the DNA fragment. Thus purified DNA fragment was finally dissolved in 10 µl of TE. The amplified DNA fragment of about 2 kbp thus purified was cleaved by means of restriction endonucleases EcoRI and HindIII, and then subjected to phenol/chloroform extraction and ethanol precipitation to purify the DNA fragment. Thus purified DNA fragment was finally dissolved in 10 µl of TE. Likewise, pPT-DB1 was cleaved by means of EcoRI and HindIII, and then subjected to agarose gel electrophoresis (using Type VII low-melting-point agarose, a product by Sigma Corporation; agarose concentration of 0.7%). An agarose fragment comprising only the DNA fragment of about 2.7 kbp was cut out of the agarose gel. The thus-cut agarose fragment (about 0.1 g) was finely pulverized, suspended in 1 ml of the TE solution, and kept at 55° C. for 1 hour, whereby the agarose fragment was completely melted. The resulting agarose melt was subjected to phenol/chloroform extraction and ethanol precipitation to purify the DNA fragment. Thus purified DNA fragment was finally dissolved in 10 µl of TE. Thus obtained DNA fragments of about 2 kbp and of about 2.7 kbp were subjected to DNA ligation, using a DNA ligation kit (manufactured by Takara Shuzo Co., Ltd.). Then, a competent cell of *E. coli* HB101 (manufactured by Toyobo Co., Ltd.) was transformed with the reaction product to obtain a transformant No. 1.

The conversion and the selectivity were determined in the following manner in the production of the amide compound using the obtained transformant.

In a 500 ml Erlenmeyer flask with baffles, 100 ml of a liquid LB medium comprising 40 µg/ml of ferric sulfate/heptahydrate and 10 µg/ml of cobalt chloride/dihydrate was prepared and sterilized by autoclaving at 121° C. for 20 minutes. Ampicillin was added to this medium to have a final concentration of 100 µg/ml. On the medium, one platinum loop of the transformant No. 1 was inoculated and incubated therein at 37° C. for about 20 hours with stirring at 130 rpm. The cells were separated from the resulting culture by centrifugation (5,000 G×15 minutes), and then resuspending the cells in 50 ml of physiological saline, followed by another centrifugation (5,000 G×15 minutes). 0.1 g of the cells was suspended in 20 ml of an aqueous solution (pH 7.0) of 50 mM potassium phosphate. To this, 1 ml of acrylonitrile or methacrylonitrile was added, and this mixture was gently stirred at 10° C. for 1 hour to react. After completion of the reaction, an analysis of the reaction solution was carried out with HPLC, and it was found that the reaction solution contained only an amide compound (acrylamide or methacrylamide) of a molar amount corresponding to the amount of the added nitrile compound (acrylonitrile or methacrylonitrile), and that the nitrile compound (acrylonitrile or methacrylonitrile) and the corresponding organic acid (acrylic acid or methacrylic acid) were absent. That is, the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 1, in which it is known that the $6^{th}$ Leu in the α-subunit of the nitrile hydratase from the clone shown therein was substituted with Met.

TABLE 1

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 1 | $6^{th}$ position in α-subunit | Leu | Met | CTG | ATG |

Reference Example 2

Construction (2) of the Substituted Amino Acid Having Nitrile Hydratase Activity For the substitution with Thr for the $6^{th}$ Leu in the α-subunit, using the plasmid DNA pPT-DB1 as the template, the plasmid DNA pPT-DB1 was subjected to introduction of site-specific mutation in the same manner as in Reference Example 1.

Using 10 ng of the plasmid DNA pPT-DB1 as prepared in Reference Example 1 as the template, PCRs of two different types were carried out. For the PCR reaction No. 1, a reaction system of 50 µl in total comprising 50 pmols of the primer having the sequence as forth in SEQ ID No: 11 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 2 was then obtained in completely the same manner as in Reference Example 1 comprising the PCR reaction No. 2.

The addition rate and the selectivity was determined in the same manner as in Reference Example 1 were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 2, in which it is known that the 6$^{th}$ Leu in the α-subunit of the nitrile hydratase from the clone shown therein was substituted with Thr.

TABLE 2

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 2 | 6$^{th}$ position in α-subunit | Leu | Thr | CTG | ACG |

Reference Example 3

Construction (3) of the Substituted Amino Acid Having Nitrile Hydratase Activity For the substitution with Ala for the 6$^{th}$ Leu in the α-subunit, using the plasmid DNA pPT-DB1 as the template, the plasmid DNA pPT-DB1 was subjected to introduction of site-specific mutation in the same manner as in Reference Example 1.

Using 10 ng of the plasmid DNA pPT-DB1 as prepared in Reference Example 1 as the template, PCRs of two different types were carried out. For the PCR reaction No. 1, a reaction system of 50 µl in total comprising 50 pmols of the primer having the sequence as forth in SEQ ID No: 12 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 3 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 3, in which it is known that the 6$^{th}$ Leu in the α-subunit of the nitrile hydratase from the clone shown therein was substituted with Ala.

TABLE 3

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 3 | 6$^{th}$ position in α-subunit | Leu | Ala | CTG | GCG |

Reference Example 4

Construction (4) of the Substituted Amino Acid Having Nitrile Hydratase Activity For the substitution with Val for the 6$^{th}$ Leu in the α-subunit, using the plasmid DNA pPT-DB1 as the template, the plasmid DNA pPT-DB1 was subjected to introduction of site-specific mutation in the same manner as in Reference Example 1.

Using 10 ng of the plasmid DNA pPT-DB1 as prepared in Reference Example 1 as the template, PCRs of two different types were carried out. For the PCR reaction No. 1, a reaction system of 50 µl in total comprising 50 pmols of the primer having the sequence as forth in SEQ ID No: 13 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72°

C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 4 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 4, in which it is known that the $6^{th}$ Leu in the α-subunit of the nitrile hydratase from the clone shown therein was substituted with Val.

TABLE 4

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 4 | $6^{th}$ position in α-subunit | Leu | Val | CTG | GTG |

Reference Example 5

Construction (5) of the Substituted Amino Acid Having Nitrile Hydratase Activity For the substitution with Val for the $19^{th}$ Ala in the α-subunit, using the plasmid DNA pPT-DB1 as the template, the plasmid DNA pPT-DB1 was subjected to introduction of site-specific mutation in the same manner as in Reference Example 1.

Using 10 ng of the plasmid DNA pPT-DB1 as prepared in Reference Example 1 as the template, PCRs of two different types were carried out. For the PCR reaction No. 1, a reaction system of 50 µl in total comprising 50 pmols of the primer having the sequence as forth in SEQ ID No: 14 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 5 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 5, in which it is known that the $19^{th}$ Ala in the α-subunit of the nitrile hydratase from the clone shown therein was substituted with Val.

TABLE 5

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 5 | $19^{th}$ position in α-subunit | Ala | Val | GCG | GTG |

Reference Example 6

Construction (6) of the Substituted Amino Acid Having Nitrile Hydratase Activity For the substitution with Leu for the $38^{th}$ Met in the α-subunit, using the plasmid DNA pPT-DB1 as the template, the plasmid DNA pPT-DB1 was subjected to introduction of site-specific mutation in the same manner as in Reference Example 1.

Using 10 ng of the plasmid DNA pPT-DB1 as prepared in Reference Example 1 as the template, PCRs of two different types were carried out. For the PCR reaction No. 1, a reaction system of 50 µl in total comprising 50 pmols of the primer having the sequence as forth in SEQ ID No: 15 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 6 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 6, in which it is known that the 38$^{th}$ Met in the α-subunit of the nitrile hydratase from the clone shown therein was substituted with Leu.

TABLE 6

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 6 | 38$^{th}$ position in α-subunit | Met | Leu | ATG | TTG |

Reference Example 7

Construction (7) of the Substituted Amino Acid Having Nitrile Hydratase Activity For the substitution with Ser for the 77$^{th}$ Thr in the α-subunit, using the plasmid DNA pPT-DB1 as the template, the plasmid DNA pPT-DB1 was subjected to introduction of site-specific mutation in the same manner as in Reference Example 1.

Using 10 ng of the plasmid DNA pPT-DB1 as prepared in Reference Example 1 as the template, PCRs of two different types were carried out. For the PCR reaction No. 1, a reaction system of 50 µl in total comprising 50 pmols of the primer having the sequence as forth in SEQ ID No: 16 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 7 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 7, in which it is known that the 77$^{th}$ Thr in the α-subunit of the nitrile hydratase from the clone shown therein was substituted with Ser.

TABLE 7

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 7 | 77$^{th}$ position in α-subunit | Thr | Ser | ACC | TCC |

Reference Example 8

Construction (8) of the Substituted Amino Acid Having Nitrile Hydratase Activity For the substitution with Ala for the 90$^{th}$ Gly in the α-subunit, using the plasmid DNA pPT-DB1 as the template, the plasmid DNA pPT-DB1 was subjected to introduction of site-specific mutation in the same manner as in Reference Example 1.

Using 10 ng of the plasmid DNA pPT-DB1 as prepared in Reference Example 1 as the template, PCRs of two different types were carried out. For the PCR reaction No. 1, a reaction system of 50 µl in total comprising 50 pmols of the primer having the sequence as forth in SEQ ID No: 17 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 8 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 8, in which it is known that the 90$^{th}$ Gly in the α-subunit of the nitrile hydratase from the clone shown therein was substituted with Ala.

TABLE 8

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 8 | 90$^{th}$ position in α-subunit | Gly | Ala | GGC | GCC |

Reference Example 9

Construction (9) of the Substituted Amino Acid Having Nitrile Hydratase Activity For the substitution with Ala for the 102$^{nd}$ Val in the α-subunit, using the plasmid DNA pPT-DB1 as the template, the plasmid DNA pPT-DB1 was subjected to introduction of site-specific mutation in the same manner as in Reference Example 1.

Using 10 ng of the plasmid DNA pPT-DB1 as prepared in Reference Example 1 as the template, PCRs of two different types were carried out. For the PCR reaction No. 1, a reaction system of 50 μl in total comprising 50 pmols of the primer having the sequence as forth in SEQ ID No: 18 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 9 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 9, in which it is known that the 102$^{nd}$ Val in the α-subunit of the nitrile hydratase from the clone shown therein was substituted with Ala.

TABLE 9

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 9 | 102$^{nd}$ position in α-subunit | Val | Ala | GTC | GCC |

Reference Example 10

Construction (10) of the Substituted Amino Acid Having Nitrile Hydratase Activity For the substitution with Ile for the 106$^{th}$ Val in the α-subunit, using the plasmid DNA pPT-DB1 as the template, the plasmid DNA pPT-DB1 was subjected to introduction of site-specific mutation in the same manner as in Reference Example 1.

Using 10 ng of the plasmid DNA pPT-DB1 as prepared in Reference Example 1 as the template, PCRs of two different types were carried out. For the PCR reaction No. 1, a reaction system of 50 μl in total comprising 50 pmols of the primer having the sequence as forth in SEQ ID No: 19 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 10 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 10, in which it is known that the 106$^{th}$ Val in the α-subunit of the nitrile hydratase from the clone shown therein was substituted with Ile.

TABLE 10

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 10 | 106$^{th}$ position in α-subunit | Val | Ile | GTC | ATC |

Reference Example 11

Construction (11) of the Substituted Amino Acid Having Nitrile Hydratase Activity For the substitution with Tyr for the 126$^{th}$ Phe in the α-subunit, using the plasmid DNA pPT-DB1 as the template, the plasmid DNA pPT-DB1 was subjected to introduction of site-specific mutation in the same manner as in Reference Example 1.

Using 10 ng of the plasmid DNA pPT-DB1 as prepared in Reference Example 1 as the template, PCRs of two different types were carried out. For the PCR reaction No. 1, a reaction system of 50 µl in total comprising 50 pmols of the primer having the sequence as forth in SEQ ID No: 20 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 11 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 11, in which it is known that the 126$^{th}$ Phe in the α-subunit of the nitrile hydratase from the clone shown therein was substituted with Tyr.

TABLE 11

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 11 | 126$^{th}$ position in α-subunit | Phe | Tyr | TTC | TAC |

Reference Example 12

Construction (12) of the Substituted Amino Acid Having Nitrile Hydratase Activity For the substitution with Glu for the 130$^{th}$ Gln in the α-subunit, using the plasmid DNA pPT-DB1 as the template, the plasmid DNA pPT-DB1 was subjected to introduction of site-specific mutation in the same manner as in Reference Example 1.

Using 10 ng of the plasmid DNA pPT-DB1 as prepared in Reference Example 1 as the template, PCRs of two different types were carried out. For the PCR reaction No. 1, a reaction system of 50 µl in total comprising 50 pmols of the primer having the sequence as forth in SEQ ID No: 21 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 12 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 12, in which it is known that the 130$^{th}$ Gln in the α-subunit of the nitrile hydratase from the clone shown therein was substituted with Glu.

TABLE 12

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 12 | 130th position in α-subunit | Gln | Glu | CAG | GAG |

TABLE 13

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 13 | 142nd position in α-subunit | Leu | Val | CTG | GTG |

Reference Example 13

Construction (13) of the Substituted Amino Acid Having Nitrile Hydratase Activity For the substitution with Val for the 142$^{nd}$ Leu in the α-subunit, using the plasmid DNA pPT-DB1 as the template, the plasmid DNA pPT-DB1 was subjected to introduction of site-specific mutation in the same manner as in Reference Example 1.

Using 10 ng of the plasmid DNA pPT-DB1 as prepared in Reference Example 1 as the template, PCRs of two different types were carried out. For the PCR reaction No. 1, a reaction system of 50 µl in total comprising 50 pmols of the primer having the sequence as forth in SEQ ID No: 22 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 13 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 13, in which it is known that the 142$^{nd}$ Leu in the α-subunit of the nitrile hydratase from the clone shown therein was substituted with Val.

Reference Example 14

Construction (14) of the Substituted Amino Acid Having Nitrile Hydratase Activity For the substitution with Asp for the 146$^{th}$ Glu in the α-subunit, using the plasmid DNA pPT-DB1 as the template, the plasmid DNA pPT-DB1 was subjected to introduction of site-specific mutation in the same manner as in Reference Example 1.

Using 10 ng of the plasmid DNA pPT-DB1 as prepared in Reference Example 1 as the template, PCRs of two different types were carried out. For the PCR reaction No. 1, a reaction system of 50 µl in total comprising 50 pmols of the primer having the sequence as forth in SEQ ID No: 23 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 14 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 14, in which it is known that the 146$^{th}$ Glu in the α-subunit of the nitrile hydratase from the clone shown therein was substituted with Asp.

TABLE 14

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 14 | 146th position in α-subunit | Glu | Asp | GAG | GAC |

TABLE 15

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 15 | 187th position in α-subunit | Ala | Thr | GCC | ACC |

Reference Example 15

Construction (15) of the Substituted Amino Acid Having Nitrile Hydratase Activity For the substitution with Thr for the 187th Ala in the α-subunit, using the plasmid DNA pPT-DB1 as the template, the plasmid DNA pPT-DB1 was subjected to introduction of site-specific mutation in the same manner as in Reference Example 1.

Using 10 ng of the plasmid DNA pPT-DB1 as prepared in Reference Example 1 as the template, PCRs of two different types were carried out. For the PCR reaction No. 1, a reaction system of 50 μl in total comprising 50 pmols of the primer having the sequence as forth in SEQ ID No: 24 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 15 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 15, in which it is known that the 187th Ala in the α-subunit of the nitrile hydratase from the clone shown therein was substituted with Thr.

Reference Example 16

Construction (16) of the Substituted Amino Acid Having Nitrile Hydratase Activity For the substitution with Leu for the 194th Ser in the α-subunit, using the plasmid DNA pPT-DB1 as the template, the plasmid DNA pPT-DB1 was subjected to introduction of site-specific mutation in the same manner as in Reference Example 1.

Using 10 ng of the plasmid DNA pPT-DB1 as prepared in Reference Example 1 as the template, PCRs of two different types were carried out. For the PCR reaction No. 1, a reaction system of 50 μl in total comprising 50 pmols of the primer having the sequence as forth in SEQ ID No: 25 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 16 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 16, in which it is known that the 194th Ser in the α-subunit of the nitrile hydratase from the clone shown therein was substituted with Leu.

TABLE 16

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 16 | 194$^{th}$ position in α-subunit | Ser | Leu | TCG | TTG |

TABLE 17

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 17 | 203$^{rd}$ position in α-subunit | Ala | Glu | GCG | GAG |

Reference Example 17

Construction (17) of the Substituted Amino Acid Having Nitrile Hydratase Activity For the substitution with Glu for the 203$^{rd}$ Ala in the α-subunit, using the plasmid DNA pPT-DB1 as the template, the plasmid DNA pPT-DB1 was subjected to introduction of site-specific mutation in the same manner as in Reference Example 1.

Using 10 ng of the plasmid DNA pPT-DB1 as prepared in Reference Example 1 as the template, PCRs of two different types were carried out. For the PCR reaction No. 1, a reaction system of 50 μl in total comprising 50 pmols of the primer having the sequence as forth in SEQ ID No: 26 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 17 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 17, in which it is known that the 203$^{rd}$ Ala in the α-subunit of the nitrile hydratase from the clone shown therein was substituted with Glu.

Reference Example 18

Construction (18) of the Substituted Amino Acid Having Nitrile Hydratase Activity For the substitution with Val for the 20$^{th}$ Ala in the β-subunit, using the plasmid DNA pPT-DB1 as the template, the plasmid DNA pPT-DB1 was subjected to introduction of site-specific mutation in the same manner as in Reference Example 1.

Using 10 ng of the plasmid DNA pPT-DB1 as prepared in Reference Example 1 as the template, PCRs of two different types were carried out. For the PCR reaction No. 1, a reaction system of 50 μl in total comprising 50 pmols of the primer having the sequence as forth in SEQ ID No: 27 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 18 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 18, in which it is known that the 20$^{th}$ Ala in the β-subunit of the nitrile hydratase from the clone shown therein was substituted with Val.

TABLE 18

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 18 | 20th position in β-subunit | Ala | Val | GCG | GTG |

TABLE 19

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 19 | 21st position in β-subunit | Asp | Asn | GAC | AAC |

Reference Example 19

Construction (19) of the Substituted Amino Acid Having Nitrile Hydratase Activity For the substitution with Asn for the 21st Asp in the β-subunit, using the plasmid DNA pPT-DB1 as the template, the plasmid DNA pPT-DB1 was subjected to introduction of site-specific mutation in the same manner as in Reference Example 1.

Using 10 ng of the plasmid DNA pPT-DB1 as prepared in Reference Example 1 as the template, PCRs of two different types were carried out. For the PCR reaction No. 1, a reaction system of 50 µl in total comprising 50 pmols of the primer having the sequence as forth in SEQ ID No: 28 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 19 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 19, in which it is known that the 21st Asp in the β-subunit of the nitrile hydratase from the clone shown therein was substituted with Asn.

Reference Example 20

Construction (20) of the Substituted Amino Acid Having Nitrile Hydratase Activity For the substitution with Asp for the 108th Glu in the β-subunit, using the plasmid DNA pPT-DB1 as the template, the plasmid DNA pPT-DB1 was subjected to introduction of site-specific mutation in the same manner as in Reference Example 1.

Using 10 ng of the plasmid DNA pPT-DB1 as prepared in Reference Example 1 as the template, PCRs of two different types were carried out. For the PCR reaction No. 1, a reaction system of 50 µl in total comprising 50 pmols of the primer having the sequence as forth in SEQ ID No: 29 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 20 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 20, in which it is known that the 108th Glu in the β-subunit of the nitrile hydratase from the clone shown therein was substituted with Asp.

TABLE 20

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 20 | 108th position in β-subunit | Glu | Asp | GAG | GAT |

TABLE 21

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 21 | 108th position in β-subunit | Glu | Pro | GAG | CCG |

Reference Example 21

Construction (21) of the Substituted Amino Acid Having Nitrile Hydratase Activity For the substitution with Pro for the 108th Glu in the β-subunit, using the plasmid DNA pPT-DB1 as the template, the plasmid DNA pPT-DB1 was subjected to introduction of site-specific mutation in the same manner as in Reference Example 1.

Using 10 ng of the plasmid DNA pPT-DB1 as prepared in Reference Example 1 as the template, PCRs of two different types were carried out. For the PCR reaction No. 1, a reaction system of 50 μl in total comprising 50 pmols of the primer having the sequence as forth in SEQ ID No: 30 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 21 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 21, in which it is known that the 108th Glu in the β-subunit of the nitrile hydratase from the clone shown therein was substituted with Pro.

Reference Example 22

Construction (22) of the Substituted Amino Acid Having Nitrile Hydratase Activity For the substitution with Ser for the 108th Glu in the β-subunit, using the plasmid DNA pPT-DB1 as the template, the plasmid DNA pPT-DB1 was subjected to introduction of site-specific mutation in the same manner as in Reference Example 1.

Using 10 ng of the plasmid DNA pPT-DB1 as prepared in Reference Example 1 as the template, PCRs of two different types were carried out. For the PCR reaction No. 1, a reaction system of 50 μl in total comprising 50 pmols of the primer having the sequence as forth in SEQ ID No: 31 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 22 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 22, in which it is known that the 108th Glu in the β-subunit of the nitrile hydratase from the clone shown therein was substituted with Ser.

TABLE 22

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 22 | 108$^{th}$ position in β-subunit | Glu | Ser | GAG | TCG |

TABLE 23

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 23 | 108$^{th}$ position in β-subunit | Glu | Arg | GAG | CGG |

Reference Example 23

Construction (23) of the Substituted Amino Acid Having Nitrile Hydratase Activity For the substitution with Arg for the 108$^{th}$ Glu in the β-subunit, using the plasmid DNA pPT-DB1 as the template, the plasmid DNA pPT-DB1 was subjected to introduction of site-specific mutation in the same manner as in Reference Example 1.

Using 10 ng of the plasmid DNA pPT-DB1 as prepared in Reference Example 1 as the template, PCRs of two different types were carried out. For the PCR reaction No. 1, a reaction system of 50 μl in total comprising 50 pmols of the primer having the sequence as forth in SEQ ID No: 32 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 23 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 23, in which it is known that the 108$^{th}$ Glu in the β-subunit of the nitrile hydratase from the clone shown therein was substituted with Arg.

Reference Example 24

Construction (24) of the Substituted Amino Acid Having Nitrile Hydratase Activity For the substitution with Cys for the 108$^{th}$ Glu in the β-subunit, using the plasmid DNA pPT-DB1 as the template, the plasmid DNA pPT-DB1 was subjected to introduction of site-specific mutation in the same manner as in Reference Example 1.

Using 10 ng of the plasmid DNA pPT-DB1 as prepared in Reference Example 1 as the template, PCRs of two different types were carried out. For the PCR reaction No. 1, a reaction system of 50 μl in total comprising 50 pmols of the primer having the sequence as forth in SEQ ID No: 33 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 24 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 24, in which it is known that the 108$^{th}$ Glu in the β-subunit of the nitrile hydratase from the clone shown therein was substituted with Cys.

TABLE 24

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 24 | 108th position in β-subunit | Glu | Cys | GAG | TGC |

TABLE 25

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 25 | 108th position in β-subunit | Glu | Leu | GAG | CTG |

Reference Example 25

Construction (25) of the Substituted Amino Acid Having Nitrile Hydratase Activity For the substitution with Leu for the 108th Glu in the β-subunit, using the plasmid DNA pPT-DB1 as the template, the plasmid DNA pPT-DB1 was subjected to introduction of site-specific mutation in the same manner as in Reference Example 1.

Using 10 ng of the plasmid DNA pPT-DB1 as prepared in Reference Example 1 as the template, PCRs of two different types were carried out. For the PCR reaction No. 1, a reaction system of 50 μl in total comprising 50 pmols of the primer having the sequence as forth in SEQ ID No: 34 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 25 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 25, in which it is known that the 108th Glu in the β-subunit of the nitrile hydratase from the clone shown therein was substituted with Leu.

Reference Example 26

Construction (26) of the Substituted Amino Acid Having Nitrile Hydratase Activity For the substitution with Thr for the 108th Glu in the β-subunit, using the plasmid DNA pPT-DB1 as the template, the plasmid DNA pPT-DB1 was subjected to introduction of site-specific mutation in the same manner as in Reference Example 1.

Using 10 ng of the plasmid DNA pPT-DB1 as prepared in Reference Example 1 as the template, PCRs of two different types were carried out. For the PCR reaction No. 1, a reaction system of 50 μl in total comprising 50 pmols of the primer having the sequence as forth in SEQ ID No: 35 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 26 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 26, in which it is known that the 108th Glu in the β-subunit of the nitrile hydratase from the clone shown therein was substituted with Thr.

TABLE 26

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 26 | 108th position in β-subunit | Glu | Thr | GAG | ACG |

TABLE 27

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 27 | 200th position in β-subunit | Ala | Asp | GCC | GAC |

Reference Example 27

Construction (27) of the Substituted Amino Acid Having Nitrile Hydratase Activity For the substitution with Asp for the 200th Ala in the β-subunit, using the plasmid DNA pPT-DB1 as the template, the plasmid DNA pPT-DB1 was subjected to introduction of site-specific mutation in the same manner as in Reference Example 1.

Using 10 ng of the plasmid DNA pPT-DB1 as prepared in Reference Example 1 as the template, PCRs of two different types were carried out. For the PCR reaction No. 1, a reaction system of 50 µl in total comprising 50 pmols of the primer having the sequence as forth in SEQ ID No: 36 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 27 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 27, in which it is known that the 200th Ala in the β-subunit of the nitrile hydratase from the clone shown therein was substituted with Asp.

Reference Example 28

Construction (28) of the Substituted Amino Acid Having Nitrile Hydratase Activity For the substitution with Ile for the 200th Ala in the β-subunit, using the plasmid DNA pPT-DB1 as the template, the plasmid DNA pPT-DB1 was subjected to introduction of site-specific mutation in the same manner as in Reference Example 1.

Using 10 ng of the plasmid DNA pPT-DB1 as prepared in Reference Example 1 as the template, PCRs of two different types were carried out. For the PCR reaction No. 1, a reaction system of 50 µl in total comprising 50 pmols of the primer having the sequence as forth in SEQ ID No: 37 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 28 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 28, in which it is known that the 200th Ala in the β-subunit of the nitrile hydratase from the clone shown therein was substituted with Ile.

TABLE 28

| Clone Number | Mutated Site (in β-subunit) | Change in Amino Acid Sequence Before Substitution | Change in Amino Acid Sequence After Substitution | Change in Base Sequence Before Substitution | Change in Base Sequence After Substitution |
|---|---|---|---|---|---|
| No. 28 | 200$^{th}$ position in β-subunit | Ala | Ile | GCC | ATC |

TABLE 29

| Clone Number | Mutated Site (in β-subunit) | Change in Amino Acid Sequence Before Substitution | Change in Amino Acid Sequence After Substitution | Change in Base Sequence Before Substitution | Change in Base Sequence After Substitution |
|---|---|---|---|---|---|
| No. 29 | 200$^{th}$ position in β-subunit | Ala | Val | GCC | GTC |

Reference Example 29

Construction (29) of the Substituted Amino Acid Having Nitrile Hydratase Activity For the substitution with Val for the 200$^{th}$ Ala in the β-subunit, using the plasmid DNA pPT-DB1 as the template, the plasmid DNA pPT-DB1 was subjected to introduction of site-specific mutation in the same manner as in Reference Example 1.

Using 10 ng of the plasmid DNA pPT-DB1 as prepared in Reference Example 1 as the template, PCRs of two different types were carried out. For the PCR reaction No. 1, a reaction system of 50 μl in total comprising 50 pmols of the primer having the sequence as forth in SEQ ID No: 38 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 29 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 29, in which it is known that the 200$^{th}$ Ala in the β-subunit of the nitrile hydratase from the clone shown therein was substituted with Val.

Reference Example 30

Construction (30) of the Substituted Amino Acid Having Nitrile Hydratase Activity For the substitution with Glu for the 200$^{th}$ Ala in the β-subunit, using the plasmid DNA pPT-DB1 as the template, the plasmid DNA pPT-DB1 was subjected to introduction of site-specific mutation in the same manner as in Reference Example 1.

Using 10 ng of the plasmid DNA pPT-DB1 as prepared in Reference Example 1 as the template, PCRs of two different types were carried out. For the PCR reaction No. 1, a reaction system of 50 μl in total comprising 50 pmols of the primer having the sequence as forth in SEQ ID No: 39 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 30 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 30, in which it is known that the 200$^{th}$ Ala in the β-subunit of the nitrile hydratase from the clone shown therein was substituted with Glu.

TABLE 30

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 30 | 200$^{th}$ position in β-subunit | Ala | Glu | GCC | GAG |

TABLE 31

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 31 | 212$^{th}$ position in β-subunit | Ser | Tyr | TCC | TAC |

Reference Example 31

Construction (31) of the Substituted Amino Acid Having Nitrile Hydratase Activity For the substitution with Tyr for the 212$^{th}$ Ser in the β-subunit, using the plasmid DNA pPT-DB1 as the template, the plasmid DNA pPT-DB1 was subjected to introduction of site-specific mutation in the same manner as in Reference Example 1.

Using 10 ng of the plasmid DNA pPT-DB1 as prepared in Reference Example 1 as the template, PCRs of two different types were carried out. For the PCR reaction No. 1, a reaction system of 50 µl in total comprising 50 pmols of the primer having the sequence as forth in SEQ ID No: 40 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 31 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 31, in which it is known that the 212$^{th}$ Ser in the β-subunit of the nitrile hydratase from the clone shown therein was substituted with Tyr.

Reference Example 32

Construction (32) of the Substituted Amino Acid Having Nitrile Hydratase Activity This is to demonstrate that the mutant with the substituted amino acid sequence comprising both of the mutated position from the clone No. 5 (where the 19$^{th}$ Ala in the α-subunit was substituted with Val) and that from the clone No. 11 (where the 126$^{th}$ Phe in the α-subunit was substituted with Tyr) still had the nitrile hydratase activity.

10 ml of a liquid LB medium was put into a 30 ml test tube, and sterilized by autoclaving at 121° C. for 20 minutes. Ampicillin was added to this medium to have a final concentration of 100 µg/ml. On the medium, one platinum loop of the cells of the clone No. 11 as prepared in Reference Example 11 was inoculated and incubated therein at 37° C. for about 20 hours with stirring at 300 rpm. 1 ml of the resulting culture was put into a suitable centrifugal tube, and this was subjected to centrifugation (15,000 rpm, 5 minutes) to separate the cells from the culture. The plasmid DNA of the clone No. 11 was prepared from the cells by alkaline SDS extraction.

Using 1 µg of the plasmid DNA of the clone No. 11 as the template, PCR of two different types was carried out. For the PCR reaction No. 1, a reaction system of 50 µl in total comprising 50 pmols of the primer having the sequence as forth in SEQ ID No: 14 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR-reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 32 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 32, in which it is known that the $19^{th}$ Ala in the α-subunit in the wild nitrile hydratase was substituted with Val and the $126^{th}$ Phe in the same was substituted with Tyr.

TABLE 32

| Clone Number | Mutated Site (in α-subunit) | Change in Amino Acid Sequence | | Change in Base Sequence | |
|---|---|---|---|---|---|
| | | Wild Type | Mutant | Wild Type | Mutant |
| No. 32 | $19^{th}$ position in α-subunit | Ala | Val | GCG | GTG |
| | $126^{th}$ position in α-subunit | Phe | Tyr | TTC | TAC |

Reference Example 33

Construction (33) of the Substituted Amino Acid Having Nitrile Hydratase Activity This is to demonstrate that the mutant with the substituted amino acid sequence comprising both of the mutated position from the clone No. 1 (where the $6^{th}$ Leu in the α-subunit was substituted with Met) and that from the clone No. 32 (where the $19^{th}$ Ala in the α-subunit was substituted with Val and the $126^{th}$ Phe in the α-subunit was substituted with Tyr) still had the nitrile hydratase activity.

10 ml of a liquid LB medium was put into a 30 ml test tube, and sterilized by autoclaving at 121° C. for 20 minutes. Ampicillin was added to this medium to have a final concentration of 100 μg/ml. On the medium, one platinum loop of the cells of the clone No. 32 as prepared in Reference Example 32 was inoculated and incubated therein at 37° C. for about 20 hours with stirring at 300 rpm. 1 ml of the resulting culture was put into a suitable centrifugal tube, and this was subjected to centrifugation (15,000 rpm, 5 minutes) to separate the cells from the culture. The plasmid DNA of the clone No. 32 was prepared from the cells by alkaline SDS extraction.

Using 1 μg of the plasmid DNA of the clone No. 32 as the template, PCRs of two different types were carried out. For the PCR reaction No. 1, a reaction system of 50 μl in total comprising 50 pmols of the primer having the sequence as forth in SEQ ID No: 7 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 33 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 33, in which it is known that the $6^{th}$ Leu in the α-subunit in the wild nitrile hydratase was substituted with Met, the $19^{th}$ Ala in the same was substituted with Val and the $126^{th}$ Phe in the same was substituted with Tyr.

TABLE 33

| Clone Number | Mutated Site (in α-subunit) | Change in Amino Acid Sequence | | Change in Base Sequence | |
|---|---|---|---|---|---|
| | | Wild Type | Mutant | Wild Type | Mutant |
| No. 33 | $6^{th}$ position in α-subunit | Leu | Met | CTG | ATG |
| | $19^{th}$ position in α-subunit | Ala | Val | GCG | GTG |
| | $126^{th}$ position in α-subunit | Phe | Tyr | TTC | TAC |

Reference Example 34

Construction (34) of the Substituted Amino Acid Having Nitrile Hydratase Activity This is to demonstrate that the mutant with the substituted amino acid sequence comprising both of the mutated position from the clone No. 2 (where the $6^{th}$ Leu in the α-subunit was substituted with Thr) and that from the clone No. 32 (where the $19^{th}$ Ala in the α-subunit was substituted with Val and the $126^{th}$ Phe in the α-subunit was substituted with Tyr) still had the nitrile hydratase activity.

Using 1 μg of the plasmid DNA of the clone No. 32 as prepared in Reference Example 33 as the template, PCRs of two different types were carried out. For the PCR reaction No. 1, a reaction system of 50 μl in total comprising 50 pmols of the primer having the sequence as forth in SEQ ID No: 11 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 34 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 34, in which it is known that the $6^{th}$ Leu in the α-subunit in the wild nitrile hydratase was substituted with Thr, the $19^{th}$ Ala in the same was substituted with Val and the $126^{th}$ Phe in the same was substituted with Tyr.

TABLE 34

| Clone Number | Mutated Site (in α-subunit) | Change in Amino Acid Sequence | | Change in Base Sequence | |
|---|---|---|---|---|---|
| | | Wild Type | Mutant | Wild Type | Mutant |
| No. 34 | $6^{th}$ position in α-subunit | Leu | Thr | CTG | ACG |
| | $19^{th}$ position in α-subunit | Ala | Val | GCG | GTG |
| | $126^{th}$ position in α-subunit | Phe | Tyr | TTC | TAC |

Reference Example 35

Construction (35) of the Substituted Amino Acid Having Nitrile Hydratase Activity This is to demonstrate that the mutant with the substituted amino acid sequence comprising both of the mutated position from the clone No. 3 (where the $6^{th}$ Leu in the α-subunit was substituted with Ala) and that from the clone No. 32 (where the $19^{th}$ Ala in the α-subunit was substituted with Val and the $126^{th}$ Phe in the α-subunit was substituted with Tyr) still had the nitrile hydratase activity.

Using 1 µg of the plasmid DNA of the clone No. 32 as prepared in Reference Example 33 as the template, PCRs of two different types were carried out. For the PCR reaction No. 1, a reaction system of 50 µl in total comprising 50 pmols of the primer having the sequence as forth in SEQ ID No: 12 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 35 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 35, in which it is known that the $6^{th}$ Leu in the α-subunit in the wild nitrile hydratase was substituted with Ala, the $19^{th}$ Ala in the same was substituted with Val and the $126^{th}$ Phe in the same was substituted with Tyr.

TABLE 35

| Clone Number | Mutated Site (in α-subunit) | Change in Amino Acid Sequence | | Change in Base Sequence | |
|---|---|---|---|---|---|
| | | Wild Type | Mutant | Wild Type | Mutant |
| No. 35 | $6^{th}$ position in α-subunit | Leu | Ala | CTG | GCG |
| | $19^{th}$ position in α-subunit | Ala | Val | GCG | GTG |
| | $126^{th}$ position in α-subunit | Phe | Tyr | TTC | TAC |

Reference Example 36

Construction (36) of the Substituted Amino Acid Having Nitrile Hydratase Activity This is to demonstrate that the mutant with the substituted amino acid sequence comprising both of the mutated position from the clone No. 20 (where the $108^{th}$ Glu in the β-subunit was substituted with Asp) and that from the clone No. 31 (where the $212^{th}$ Ser in the β-subunit was substituted with Tyr) still had the nitrile hydratase activity.

10 ml of a liquid LB medium was put into a 30 ml test tube, and sterilized by autoclaving at 121° C. for 20 minutes. Ampicillin was added to this medium to have a final concentration of 100 µg/ml. On the medium, one platinum loop of the cells of the clone No. 31 as prepared in Reference Example 31 was inoculated and incubated therein at 37° C. for about 20 hours with stirring at 300 rpm. 1 ml of the resulting culture was put into a suitable centrifugal tube, and this was subjected to centrifugation (15,000 rpm, 5 minutes) to separate the cells from the culture. The plasmid DNA of the clone No. 31 was prepared from the cells by alkaline SDS extraction.

Using 1 µg of the plasmid DNA of the clone No. 31 as the template, PCRs of two different types were carried out. For the PCR reaction No. 1, a reaction system of 50 µl in total comprising 50 pmols of the primer having the sequence as forth in SEQ ID No: 29 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 36 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 36, in which it is known that the $108^{th}$ Glu in the β-subunit in the wild nitrile hydratase was substituted with Asp and the $212^{th}$ Ser in the same was substituted with Tyr.

TABLE 36

| Clone Number | Mutated Site (in β-subunit) | Change in Amino Acid Sequence | | Change in Base Sequence | |
|---|---|---|---|---|---|
| | | Wild Type | Mutant | Wild Type | Mutant |
| No. 36 | $108^{th}$ position in β-subunit | Glu | Asp | GAG | GAT |
| | $212^{th}$ position in β-subunit | Ser | Tyr | TCC | TAC |

Reference Example 37

Construction (37) of the Substituted Amino Acid Having Nitrile Hydratase Activity This is to demonstrate that the mutant with the substituted amino acid sequence comprising both of the mutated position from the clone No. 23 (where the $108^{th}$ Glu in the β-subunit was substituted with Arg) and that from the clone No. 31 (where the $212^{th}$ Ser in the β-subunit was substituted with Tyr) still had the nitrile hydratase activity.

Using 1 μg of the plasmid DNA of the clone No. 31 as prepared in Reference Example 36 as the template, PCRs of two different types were carried out. For the PCR reaction No. 1, a reaction system of 50 μl in total comprising 50 pmols of the primer having the sequence as forth in SEQ ID No: 32 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 37 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 37, in which it is known that the $108^{th}$ Glu in the β-subunit in the wild nitrile hydratase was substituted with Arg and the $212^{th}$ Ser in the same was substituted with Tyr.

TABLE 37

| Clone Number | Mutated Site (in β-subunit) | Change in Amino Acid Sequence | | Change in Base Sequence | |
|---|---|---|---|---|---|
| | | Wild Type | Mutant | Wild Type | Mutant |
| No. 37 | $108^{th}$ position in β-subunit | Glu | Arg | GAG | CGG |
| | $212^{th}$ position in β-subunit | Ser | Tyr | TCC | TAC |

Reference Example 38

Construction (38) of the Substituted Amino Acid Having Nitrile Hydratase Activity This is to demonstrate that the mutant with the substituted amino acid sequence comprising both of the mutated position from the clone No. 27 (where the $200^{th}$ Ala in the β-subunit was substituted with Asp) and that from the clone No. 31 (where the $212^{th}$ Ser in the β-subunit was substituted with Tyr) still had the nitrile hydratase activity.

Using 1 μg of the plasmid DNA of the clone No. 31 as prepared in Reference Example 36 as the template, PCRs of two different types were carried out. For the PCR reaction No. 1, a reaction system of 50 μl in total comprising 50 pmols of the primer having the sequence as forth in SEQ ID No: 36 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 38 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 38, in which it is known that the $200^{th}$ Ala in the β-subunit in the wild nitrile hydratase was substituted with Asp and the $212^{th}$ Ser in the same was substituted with Tyr.

TABLE 38

| Clone Number | Mutated Site (in β-subunit) | Change in Amino Acid Sequence | | Change in Base Sequence | |
|---|---|---|---|---|---|
| | | Wild Type | Mutant | Wild Type | Mutant |
| No. 38 | $200^{th}$ position in β-subunit | Ala | Asp | GCC | GAC |
| | $212^{th}$ position in β-subunit | Ser | Tyr | TCC | TAC |

Reference Example 39

Construction (39) of the Substituted Amino Acid Having Nitrile Hydratase Activity This is to demonstrate that the mutant with the substituted amino acid sequence comprising both of the mutated position from the clone No. 30 (where the $200^{th}$ Ala in the β-subunit was substituted with Glu) and that from the clone No. 31 (where the $212^{th}$ Ser in the β-subunit was substituted with Tyr) still had the nitrile hydratase activity.

Using 1 μg of the plasmid DNA of the clone No. 31 as prepared in Reference Example 36 as the template, PCRs of two different types were carried out. For the PCR reaction No. 1, a reaction system of 50 μl in total comprising 50 pmols of the primer having the sequence as forth in SEQ ID No: 39 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 39 was then obtained in completely the same manner as in Reference Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 39, in which it is known that the $200^{th}$ Ala in the β-subunit in the wild nitrile hydratase was substituted with Glu and the $212^{th}$ Ser in the same was substituted with Tyr.

TABLE 39

| Clone Number | Mutated Site (in β-subunit) | Change in Amino Acid Sequence | | Change in Base Sequence | |
|---|---|---|---|---|---|
| | | Wild Type | Mutant | Wild Type | Mutant |
| No. 39 | $200^{th}$ position in β-subunit | Ala | Glu | GCC | GAG |
| | $212^{th}$ position in β-subunit | Ser | Tyr | TCC | TAC |

Example 1

Construction (40) of the Substituted Amino Acid Having Nitrile Hydratase Activity For the substitution with Met for the $36^{th}$ Thr in the α-subunit, introduction of site-specific mutation was performed using a "LA PCR in vitro mutagenesis Kit" (manufactured by Takara Shuzo Co., Ltd.). Hereinafter, the "LA PCR in vitro mutagenesis Kit" is simply referred to as the kit. In following Examples, the kit was handled on the basis of the principle thereof and in accordance with the manufacturer's instructions for the kit.

10 ml of a liquid LB medium was put into a 30 ml test tube, and sterilized by autoclaving at 121° C. for 20 minutes. Ampicillin was added to this medium to have a final concentration of 100 μg/ml. On the medium, one platinum loop of the cells of MT-10822 were inoculated and incubated therein at 37° C. for about 20 hours with stirring at 300 rpm. 1 ml of the resulting culture was put into a suitable centrifugal tube, and this was subjected to centrifugation (15,000 rpm, 5 minutes) to separate the cells from the culture. The plasmid pPT-DB1 was prepared from the cells by alkaline SDS extraction.

Using 10 ng of pPT-DB1 as the template, PCRs of two different types were carried out. For the PCR reaction No. 1, a reaction system of 50 μl in total comprising 50 pmols of the primer having the sequence as forth in SEQ ID No: 41 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. From each of these PCR reaction mixtures, the excess primers and dNTP were removed using Microcon 100 (manufactured by Takara Shuzo Co., Ltd.), and then TE was added to each of the mixtures to prepare 50 μl each of TE solutions. An annealing solution of 47.5 μl in total containing 0.5 μl of both of the above TE solutions (for the composition of the system, the manufacturer's instructions for the kit were followed) was prepared, and this solution was subjected to annealing by performing thermal denaturation of the solution at 98° C. for 10 minutes, subsequently cooling the solution to 37° C. at a constant cooling rate over a period of 60 minutes, and then maintaining it at 37° C. for 15 minutes. To thus annealed solution, 0.5 μl of TaKaRa LA Taq was added, and the solution was heated at 72° C. for 3 minutes, thus completing the formation of heterologous double-stranded DNA. This was then subjected to PCR reaction No. 3. For the PCR reaction No. 3, a reaction system of 50 μl in total comprising 50 pmols of an M13 primer M4 (having the sequence as forth in SEQ ID No: 8 in the Sequence Listing) and 50 pmols of an M13 primer RV (having the sequence as forth in SEQ ID No: 10 in the Sequence Listing) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. After completion of the PCR reaction 3, 5 μl of the reaction mixture was subjected to agarose gel electrophoresis (using Type VII low-melting-point agarose, a product by Sigma Corporation; agarose concentration of 0.8% by weight), and an assay of the DNA amplification product was carried out, thereby it being possible to confirm the presence of an amplified DNA product of about 2 kbp. Subsequently, an agarose fragment comprising only a DNA fragment of about 2 kbp was cut out of the agarose gel. The thus-cut agarose fragment (about 0.1 g) was finely pulverized, suspended in 1 ml of a TE solution, and kept at 55° C. for 1 hour, whereby the agarose fragment was completely melted. The resulting agarose melt was then subjected to phenol/chloroform extraction and ethanol precipitation to purify the DNA fragment. Thus purified DNA fragment was finally dissolved in 10 μl of TE. The amplified DNA fragment of about 2 kbp thus purified was cleaved by means of restriction endonucleases EcoRI and HindIII, and then subjected to phenol/chloroform extraction and ethanol precipitation to purify the DNA fragment. Thus purified DNA fragment was finally dissolved in 10 μl of TE. Likewise, pPT-DB1 was cleaved by means of EcoRI and HindIII, and then subjected to agarose gel electrophoresis (using Type VII low-melting-point agarose, a product by Sigma Corporation; agarose concentration of 0.7%). An agarose fragment comprising only the DNA fragment of about 2.7 kbp was cut out of the agarose gel. The thus-cut agarose fragment (about 0.1 g) was finely pulverized, suspended in 1 ml of the TE solution, and kept at 55° C. for 1 hour, whereby the agarose fragment was completely melted. The resulting agarose melt was subjected to phenol/chloroform extraction and ethanol precipitation to purify the DNA fragment. Thus purified DNA fragment was finally dissolved in 10 μl of TE. Thus obtained DNA fragments of about 2 kbp and of about 2.7 kbp were subjected to DNA ligation, using a DNA ligation kit (manufactured by Takara Shuzo Co., Ltd.). A competent cell of E. coli HB101 (manufactured by Toyobo Co., Ltd.) was transformed with the reaction product to obtain a transformant No. 40.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 40, in which it is known that the $36^{th}$ Thr in the α-subunit of the nitrile hydratase from the clone was substituted with Met.

TABLE 40

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 40 | $36^{th}$ position in α-subunit | Thr | Met | ACG | ATG |

Example 2

Construction (41) of the Substituted Amino Acid Having Nitrile Hydratase Activity For the substitution with His for the $71^{st}$ Arg in the α-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 42 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 41 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 41, in which it is known that the $71^{st}$ Arg in the α-subunit of the nitrile hydratase from the clone was substituted with His.

TABLE 41

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 41 | $71^{st}$ position in α-subunit | Arg | His | CGT | CAT |

Example 3

Construction (42) of the Substituted Amino Acid Having Nitrile Hydratase Activity For the substitution with Asp for the $148^{th}$ Gly in the α-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 43 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 42 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 42, in which it is known that the $148^{th}$ Gly in the α-subunit of the nitrile hydratase from the clone was substituted with Asp.

TABLE 42

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 42 | $148^{th}$ position in α-subunit | Gly | Asp | GGC | GAC |

Example 4

Construction (43) of the Substituted Amino Acid Having Nitrile Hydratase Activity For the substitution with Arg for the $204^{th}$ Val in the α-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 44 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 43 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 43, in which it is known that the $204^{th}$ Val in the α-subunit of the nitrile hydratase from the clone was substituted with Arg.

TABLE 43

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 43 | 204$^{th}$ position in α-subunit | Val | Arg | GTC | CGC |

TABLE 44

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 44 | 204$^{th}$ position in α-subunit | Val | Lys | GTC | AAA |

Example 5

Construction (44) of the Substituted Amino Acid Having Nitrile Hydratase Activity For the substitution with Lys for the 204$^{th}$ Val in the α-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 µl in total comprising 50 pmols of the primer having the sequence as forth in SEQ ID No: 45 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 44 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 44, in which it is known that the 204$^{th}$ Val in the α-subunit of the nitrile hydratase from the clone was substituted with Lys.

Example 6

Construction (45) of the Substituted Amino Acid Having Nitrile Hydratase Activity For the substitution with Trp for the 204$^{th}$ Val in the α-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 µl in total comprising 50 pmols of the primer having the sequence as forth in SEQ ID No: 46 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 45 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 45, in which it is known that the 204$^{th}$ Val in the α-subunit of the nitrile hydratase from the clone was substituted with Trp.

TABLE 45

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 45 | 204$^{th}$ position in α-subunit | Val | Trp | GTC | TGG |

Example 7

Construction (46) of the Substituted Amino Acid Having Nitrile Hydratase Activity For the substitution with Thr for the 204$^{th}$ Val in the α-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 47 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 46 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 46, in which it is known that the 204$^{th}$ Val in the α-subunit of the nitrile hydratase from the clone was substituted with Thr.

TABLE 46

| Clone Number | Mutated Site (in α-subunit) | Change in Amino Acid Sequence | | Change in Base Sequence | |
|---|---|---|---|---|---|
| | | Before Substitution | After Substitution | Before Substitution | After Substitution |
| No. 46 | 204$^{th}$ position in α-subunit | Val | Thr | GTC | ACC |

Example 8

Construction (47) of the Substituted Amino Acid Having Nitrile Hydratase Activity For the substitution with Asp for the 10$^{th}$ Thr in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 48 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 47 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 47, in which it is known that the 10$^{th}$ Thr in the β-subunit of the nitrile hydratase from the clone shown therein was substituted with Asp.

TABLE 47

| Clone Number | Mutated Site (in β-subunit) | Change in Amino Acid Sequence Before Substitution | Change in Amino Acid Sequence After Substitution | Change in Base Sequence Before Substitution | Change in Base Sequence After Substitution |
| --- | --- | --- | --- | --- | --- |
| No. 47 | 10th position in β-subunit | Thr | Asp | ACC | GAC |

TABLE 48

| Clone Number | Mutated Site (in β-subunit) | Change in Amino Acid Sequence Before Substitution | Change in Amino Acid Sequence After Substitution | Change in Base Sequence Before Substitution | Change in Base Sequence After Substitution |
| --- | --- | --- | --- | --- | --- |
| No. 48 | 10th position in β-subunit | Thr | Glu | ACC | GAA |

Example 9

Construction (48) of the Substituted Amino Acid Having Nitrile Hydratase Activity For the substitution with Glu for the 10th Thr in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 49 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 48 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 48, in which it is known that the 10th Thr in the β-subunit of the nitrile hydratase from the clone shown therein was substituted with Glu.

Example 10

Construction (49) of the Substituted Amino Acid Having Nitrile Hydratase Activity For the substitution with Trp for the 10th Thr in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 50 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 49 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 49, in which it is known that the 10th Thr in the β-subunit of the nitrile hydratase from the clone shown therein was substituted with Trp.

TABLE 49

| Clone Number | Mutated Site (in β-subunit) | Change in Amino Acid Sequence Before Substitution | Change in Amino Acid Sequence After Substitution | Change in Base Sequence Before Substitution | Change in Base Sequence After Substitution |
|---|---|---|---|---|---|
| No. 49 | 10$^{th}$ position in β-subunit | Thr | Trp | ACC | TGG |

TABLE 50

| Clone Number | Mutated Site (in β-subunit) | Change in Amino Acid Sequence Before Substitution | Change in Amino Acid Sequence After Substitution | Change in Base Sequence Before Substitution | Change in Base Sequence After Substitution |
|---|---|---|---|---|---|
| No. 50 | 10$^{th}$ position in β-subunit | Thr | Gly | ACC | GGC |

Example 11

Construction (50) of the Substituted Amino Acid Having Nitrile Hydratase Activity For the substitution with Gly for the 10$^{th}$ Thr in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 51 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 50 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 50, in which it is known that the 10$^{th}$ Thr in the β-subunit of the nitrile hydratase from the clone shown therein was substituted with Gly.

Example 12

Construction (51) of the Substituted Amino Acid Having Nitrile Hydratase Activity For the substitution with Tyr for the 10$^{th}$ Thr in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in. Example 1 as the template, PCRs of two different types were carried out. For the PCR reaction No. 1, a reaction system of 50 μl in total comprising 50 pmols of the primer having the sequence as forth in SEQ ID No: 52 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 51 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 51, in which it is known that the 10$^{th}$ Thr in the β-subunit of the nitrile hydratase from the clone shown therein was substituted with Tyr.

TABLE 51

| Clone Number | Mutated Site (in β-subunit) | Change in Amino Acid Sequence Before Substitution | Change in Amino Acid Sequence After Substitution | Change in Base Sequence Before Substitution | Change in Base Sequence After Substitution |
|---|---|---|---|---|---|
| No. 51 | 10$^{th}$ position in β-subunit | Thr | Tyr | ACC | TAC |

TABLE 52

| Clone Number | Mutated Site (in β-subunit) | Change in Amino Acid Sequence Before Substitution | Change in Amino Acid Sequence After Substitution | Change in Base Sequence Before Substitution | Change in Base Sequence After Substitution |
|---|---|---|---|---|---|
| No. 52 | 10$^{th}$ position in β-subunit | Thr | Cys | ACC | TGC |

Example 13

Construction (52) of the Substituted Amino Acid Having Nitrile Hydratase Activity For the substitution with Cys for the 10$^{th}$ Thr in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 µl in total comprising 50 pmols of the primer having the sequence as forth in SEQ ID No: 53 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 52 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells, by alkaline SDS extraction. Next, the base sequence of the nitrile hydratase gene was determined by the dideoxy chain termination method using a sequencing kit and an Autosequencer 373A manufactured by ABI. The results are shown in Table 52, in which it is known that the 10$^{th}$ Thr in the β-subunit of the nitrile hydratase from the clone shown therein was substituted with Cys.

Example 14

Construction (53) of the Substituted Amino Acid Having Nitrile Hydratase Activity For the substitution with Gly for the 32$^{nd}$ Val in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 µl in total comprising 50 pmols of the primer having the sequence as forth in SEQ ID No: 54 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 53 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 53, in which it is known that the 32$^{nd}$ Val in the β-subunit of the nitrile hydratase from the clone shown therein was substituted with Gly.

TABLE 53

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 53 | 32$^{nd}$ position in β-subunit | Val | Gly | GTC | GGC |

TABLE 54

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 54 | 37$^{th}$ position in β-subunit | Phe | Thr | TTC | ACC |

Example 15

Construction (54) of the Substituted Amino Acid Having Nitrile Hydratase Activity For the substitution with Thr for the 37$^{th}$ Phe in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 µl in total comprising 50 pmols of the primer having the sequence as forth in SEQ ID No: 55 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 54 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 54, in which it is known that the 37$^{th}$ Phe in the β-subunit of the nitrile hydratase from the clone shown therein was substituted with Thr.

Example 16

Construction (55) of the Substituted Amino Acid Having Nitrile Hydratase Activity For the substitution with Ala for the 37$^{th}$ Phe in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 µl in total comprising 50 pmols of the primer having the sequence as forth in SEQ ID No: 56 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 55 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 55, in which it is known that the 37$^{th}$ Phe in the β-subunit of the nitrile hydratase from the clone shown therein was substituted with Ala.

TABLE 55

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 55 | 37th position in β-subunit | Phe | Ala | TTC | GCC |

TABLE 56

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 56 | 37th position in β-subunit | Phe | Leu | TTC | CTC |

Example 17

Construction (56) of the Substituted Amino Acid Having Nitrile Hydratase Activity For the substitution with Leu for the 37th Phe in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 µl in total comprising 50 pmols of the primer having the sequence as forth in SEQ ID No: 57 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 56 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 56, in which it is known that the 37th Phe in the β-subunit of the nitrile hydratase from the clone shown therein was substituted with Leu.

Example 18

Construction (57) of the Substituted Amino Acid Having Nitrile Hydratase Activity For the substitution with Ile for the 37th Phe in the β-subunit; using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 µl in total comprising 50 pmols of the primer having the sequence as forth in SEQ ID No: 58 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 57 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 57, in which it is known that the 37th Phe in the β-subunit of the nitrile hydratase from the clone shown therein was substituted with Ile.

TABLE 57

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 57 | 37th position in β-subunit | Phe | Ile | TTC | ATC |

TABLE 58

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 58 | 37th position in β-subunit | Phe | Val | TTC | GTC |

Example 19

Construction (58) of the Substituted Amino Acid Having Nitrile Hydratase Activity For the substitution with Val for the 37th Phe in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 59 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 58 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 58, in which it is known that the 37th Phe in the β-subunit of the nitrile hydratase from the clone shown therein was substituted with Val.

Example 20

Construction (59) of the Substituted Amino Acid Having Nitrile Hydratase Activity For the substitution with Glu for the 41st Phe in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 60 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 59 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 59, in which it is known that the 41st Phe in the β-subunit of the nitrile hydratase from the clone shown therein was substituted with Glu.

TABLE 59

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 59 | 41$^{st}$ position in β-subunit | Phe | Glu | TTC | GAA |

TABLE 60

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 60 | 41$^{st}$ position in β-subunit | Phe | Thr | TTC | ACC |

Example 21

Construction (60) of the Substituted Amino Acid Having Nitrile Hydratase Activity For the substitution with Thr for the 41$^{st}$ Phe in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 61 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 60 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 60, in which it is known that the 41$^{st}$ Phe in the β-subunit of the nitrile hydratase from the clone shown therein was substituted with Thr.

Example 22

Construction (61) of the Substituted Amino Acid Having Nitrile Hydratase Activity For the substitution with Ala for the 41$^{st}$ Phe in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 62 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 61 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 61, in which it is known that the 41$^{st}$ Phe in the β-subunit of the nitrile hydratase from the clone shown therein was substituted with Ala.

TABLE 61

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 61 | 41$^{st}$ position in β-subunit | Phe | Ala | TTC | GCC |

TABLE 62

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 62 | 41$^{st}$ position in β-subunit | Phe | Leu | TTC | CTC |

Example 23

Construction (62) of the Substituted Amino Acid Having Nitrile Hydratase Activity For the substitution with Leu for the 41$^{st}$ Phe in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 µl in total comprising 50 pmols of the primer having the sequence as forth in SEQ ID No: 63 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 62 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 62, in which it is known that the 41$^{st}$ Phe in the β-subunit of the nitrile hydratase from the clone shown therein was substituted with Leu.

Example 24

Construction (63) of the Substituted Amino Acid Having Nitrile Hydratase Activity For the substitution with Ile for the 41$^{st}$ Phe, in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 µl in total comprising 50 pmols of the primer having the sequence as forth in SEQ ID No: 64 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 63 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 63, in which it is known that the 41$^{st}$ Phe in the β-subunit of the nitrile hydratase from the clone shown therein was substituted with Ile.

TABLE 63

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 63 | 41$^{st}$ position in β-subunit | Phe | Ile | TTC | ATC |

TABLE 64

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 64 | 41$^{st}$ position in β-subunit | Phe | Val | TTC | GTC |

Example 25

Construction (64) of the Substituted Amino Acid Having Nitrile Hydratase Activity For the substitution with Val for the 41$^{st}$ Phe in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 65 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 64 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 64, in which it is known that the 41$^{st}$ Phe in the β-subunit of the nitrile hydratase from the clone shown therein was substituted with Val.

Example 26

Construction (65) of the Substituted Amino Acid Having Nitrile Hydratase Activity For the substitution with Gly for the 46$^{th}$ Met in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 66 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 65 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 65, in which it is known that the 46$^{th}$ Met in the β-subunit of the nitrile hydratase from the clone shown therein was substituted with Gly.

TABLE 65

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 65 | 46th position in β-subunit | Met | Gly | ATG | GGG |

TABLE 66

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 66 | 46th position in β-subunit | Met | Tyr | ATG | TAT |

Example 27

Construction (66) of the Substituted Amino Acid Having Nitrile Hydratase Activity For the substitution with Tyr for the 46th Met in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 µl in total comprising 50 pmols of the primer having the sequence as forth in SEQ ID No: 67 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 66 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 66, in which it is known that the 46th Met in the β-subunit of the nitrile hydratase from the clone shown therein was substituted with Tyr.

Example 28

Construction (67) of the Substituted Amino Acid Having Nitrile Hydratase Activity For the substitution with Leu for the 46th Met in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 µl in total comprising 50 pmols of the primer having the sequence as forth in SEQ ID No: 68 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 67 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 67, in which it is known that the 46th Met in the β-subunit of the nitrile hydratase from the clone shown therein was substituted with Leu.

TABLE 67

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 67 | 46th position in β-subunit | Met | Leu | ATG | CTG |

TABLE 68

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 68 | 46th position in β-subunit | Met | Lys | ATG | AAG |

Example 29

Construction (68) of the Substituted Amino Acid Having Nitrile Hydratase Activity For the substitution with Lys for the 46th Met in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 69 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 68 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 68, in which it is known that the 46th Met in the β-subunit of the nitrile hydratase from the clone shown therein was substituted with Lys.

Example 30

Construction (69) of the Substituted Amino Acid Having Nitrile Hydratase Activity For the substitution with Asp for the 46th Met in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 70 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 69 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 69, in which it is known that the 46th Met in the β-subunit of the nitrile hydratase from the clone shown therein was substituted with Asp.

TABLE 69

| Clone Number | Mutated Site (in β-subunit) | Change in Amino Acid Sequence Before Substitution | After Substitution | Change in Base Sequence Before Substitution | After Substitution |
|---|---|---|---|---|---|
| No. 69 | 46th position in β-subunit | Met | Asp | ATG | GAT |

TABLE 70

| Clone Number | Mutated Site (in β-subunit) | Change in Amino Acid Sequence Before Substitution | After Substitution | Change in Base Sequence Before Substitution | After Substitution |
|---|---|---|---|---|---|
| No. 70 | 48th position in β-subunit | Leu | Gly | CTG | GGG |

Example 31

Construction (70) of the Substituted Amino Acid Having Nitrile Hydratase Activity For the substitution with Gly for the 48th Leu in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 71 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 70 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 70, in which it is known that the 48th Leu in the β-subunit of the nitrile hydratase from the clone shown therein was substituted with Gly.

Example 32

Construction (71) of the Substituted Amino Acid Having Nitrile Hydratase Activity For the substitution with Ala for the 48th Leu in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 72 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 71 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 71, in which it is known that the 48th Leu in the β-subunit of the nitrile hydratase from the clone shown therein was substituted with Ala.

TABLE 71

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 71 | 48$^{th}$ position in β-subunit | Leu | Ala | CTG | GCG |

TABLE 72

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 72 | 48$^{th}$ position in β-subunit | Leu | Val | CTG | GTG |

Example 33

Construction (72) of the Substituted Amino Acid Having Nitrile Hydratase Activity For the substitution with Val for the 48$^{th}$ Leu in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 73 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 72 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 72, in which it is known that the 48$^{th}$ Leu in the β-subunit of the nitrile hydratase from the clone shown therein was substituted with Val.

Example 34

Construction (73) of the Substituted Amino Acid Having Nitrile Hydratase Activity For the substitution with Ser for the 48$^{th}$ Leu in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 74 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 73 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 73, in which it is known that the 48$^{th}$ Leu in the β-subunit of the nitrile hydratase from the clone shown therein was substituted with Ser.

TABLE 73

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 73 | 48$^{th}$ position in β-subunit | Leu | Ser | CTG | TCG |

TABLE 74

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 74 | 48$^{th}$ position in β-subunit | Leu | Thr | CTG | ACG |

Example 35

Construction (74) of the Substituted Amino Acid Having Nitrile Hydratase Activity For the substitution with Thr for the 48$^{th}$ Leu in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 µl in total comprising 50 pmols of the primer having the sequence as forth in SEQ ID No: 75 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 74 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 74, in which it is known that the 48$^{th}$ Leu in the β-subunit of the nitrile hydratase from the clone shown therein was substituted with Thr.

Example 36

Construction (75) of the Substituted Amino Acid Having Nitrile Hydratase Activity For the substitution with Arg for the 48$^{th}$ Leu in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 µl in total comprising 50 pmols of the primer having the sequence as forth in SEQ ID No: 76 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 75 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 75, in which it is known that the 48$^{th}$ Leu in the β-subunit of the nitrile hydratase from the clone shown therein was substituted with Arg.

TABLE 75

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 75 | 48$^{th}$ position in β-subunit | Leu | Arg | CTG | CGG |

TABLE 76

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 76 | 51$^{st}$ position in β-subunit | Phe | Ala | TTC | GCC |

Example 37

Construction (76) of the Substituted Amino Acid Having Nitrile Hydratase Activity For the substitution with Ala for the 51$^{st}$ Phe in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 77 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 76 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 76; in which it is known that the 51$^{st}$ Phe in the β-subunit of the nitrile hydratase from the clone shown therein was substituted with Ala.

Example 38

Construction (77) of the Substituted Amino Acid Having Nitrile Hydratase Activity For the substitution with Val for the 51$^{st}$ Phe in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 78 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 77 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 77, in which it is known that the 51$^{st}$ Phe in the β-subunit of the nitrile hydratase from the clone shown therein was substituted with Val.

TABLE 77

| Clone Number | Mutated Site (in β-subunit) | Change in Amino Acid Sequence Before Substitution | Change in Amino Acid Sequence After Substitution | Change in Base Sequence Before Substitution | Change in Base Sequence After Substitution |
|---|---|---|---|---|---|
| No. 77 | 51$^{st}$ position in β-subunit | Phe | Val | TTC | GTC |

TABLE 78

| Clone Number | Mutated Site (in β-subunit) | Change in Amino Acid Sequence Before Substitution | Change in Amino Acid Sequence After Substitution | Change in Base Sequence Before Substitution | Change in Base Sequence After Substitution |
|---|---|---|---|---|---|
| No. 78 | 72$^{nd}$ position in β-subunit | Trp | Phe | TGG | TTT |

Example 39

Construction (78) of the Substituted Amino Acid Having Nitrile Hydratase Activity For the substitution with Phe for the 72$^{nd}$ Trp in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 79 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 78 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 78, in which it is known that the 72$^{nd}$ Trp in the β-subunit of the nitrile hydratase from the clone shown therein was substituted with Phe.

Example 40

Construction (79) of the Substituted Amino Acid Having Nitrile Hydratase Activity For the substitution with Ala for the 118$^{th}$ Phe in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 80 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 79 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 79, in which it is known that the 118$^{th}$ Phe in the β-subunit of the nitrile hydratase from the clone shown therein was substituted with Ala.

TABLE 79

| Clone Number | Mutated Site (in β-subunit) | Change in Amino Acid Sequence Before Substitution | Change in Amino Acid Sequence After Substitution | Change in Base Sequence Before Substitution | Change in Base Sequence After Substitution |
|---|---|---|---|---|---|
| No. 79 | 118$^{th}$ position in β-subunit | Phe | Ala | TTC | GCC |

TABLE 80

| Clone Number | Mutated Site (in β-subunit) | Change in Amino Acid Sequence Before Substitution | Change in Amino Acid Sequence After Substitution | Change in Base Sequence Before Substitution | Change in Base Sequence After Substitution |
|---|---|---|---|---|---|
| No. 80 | 118$^{th}$ position in β-subunit | Phe | Leu | TTC | CTC |

Example 41

Construction (80) of the Substituted Amino Acid Having Nitrile Hydratase Activity For the substitution with Leu for the 118$^{th}$ Phe in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 81 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 80 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 80, in which it is known that the 118$^{th}$ Phe in the β-subunit of the nitrile hydratase from the clone shown therein was substituted with Leu.

Example 42

Construction (81) of the Substituted Amino Acid Having Nitrile Hydratase Activity For the substitution with Ile for the 118$^{th}$ Phe in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 82 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 81 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 81, in which it is known that the 118$^{th}$ Phe in the β-subunit of the nitrile hydratase from the clone shown therein was substituted with Ile.

TABLE 81

| Clone Number | Mutated Site (in β-subunit) | Change in Amino Acid Sequence Before Substitution | Change in Amino Acid Sequence After Substitution | Change in Base Sequence Before Substitution | Change in Base Sequence After Substitution |
|---|---|---|---|---|---|
| No. 81 | 118th position in β-subunit | Phe | Ile | TTC | ATC |

TABLE 82

| Clone Number | Mutated Site (in β-subunit) | Change in Amino Acid Sequence Before Substitution | Change in Amino Acid Sequence After Substitution | Change in Base Sequence Before Substitution | Change in Base Sequence After Substitution |
|---|---|---|---|---|---|
| No. 82 | 118th position in β-subunit | Phe | Val | TTC | GTC |

Example 43

Construction (82) of the Substituted Amino Acid Having Nitrile Hydratase Activity For the substitution with Val for the 118th Phe in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 83 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 82 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 82, in which it is known that the 118th Phe in the β-subunit of the nitrile hydratase from the clone shown therein was substituted with Val.

Example 44

Construction (83) of the Substituted Amino Acid Having Nitrile Hydratase Activity For the substitution with Ala for the 127th Leu in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 84 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 83 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 83, in which it is known that the 127th Leu in the β-subunit of the nitrile hydratase from the clone shown therein was substituted with Ala.

TABLE 83

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 83 | 127$^{th}$ position in β-subunit | Leu | Ala | CTG | GCG |

TABLE 84

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 84 | 127$^{th}$ position in β-subunit | Leu | Val | CTG | GTG |

Example 45

Construction (84) of the Substituted Amino Acid Having Nitrile Hydratase Activity For the substitution with Val for the 127$^{th}$ Leu in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 85 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 84 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 84, in which it is known that the 127$^{th}$ Leu in the β-subunit of the nitrile hydratase from the clone shown therein was substituted with Val.

Example 46

Construction (85) of the Substituted Amino Acid Having Nitrile Hydratase Activity For the substitution with Ser for the 127$^{th}$ Leu in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 86 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 85 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 85, in which it is known that the 127$^{th}$ Leu in the β-subunit of the nitrile hydratase from the clone shown therein was substituted with Ser.

TABLE 85

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 85 | 127th position in β-subunit | Leu | Ser | CTG | TCG |

TABLE 86

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 86 | 146th position in β-subunit | Arg | Gly | CGG | GGG |

Example 47

Construction (86) of the Substituted Amino Acid Having Nitrile Hydratase Activity For the substitution with Gly for the 146th Arg in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 87 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 86 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 86, in which it is known that the 146th Arg in the β-subunit of the nitrile hydratase from the clone shown therein was substituted with Gly.

Example 48

Construction (87) of the Substituted Amino Acid Having Nitrile Hydratase Activity For the substitution with Leu for the 160th Arg in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 88 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 87 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 87, in which it is known that the 160th Arg in the β-subunit of the nitrile hydratase from the clone shown therein was substituted with Leu.

TABLE 87

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 87 | 160$^{th}$ position in β-subunit | Arg | Leu | CGG | CTG |

TABLE 88

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 88 | 160$^{th}$ position in β-subunit | Arg | Trp | CGG | TGG |

Example 49

Construction (88) of the Substituted Amino Acid Having Nitrile Hydratase Activity For the substitution with Trp for the 160$^{th}$ Arg in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 89 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer. RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 88 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 88, in which it is known that the 160$^{th}$ Arg in the β-subunit of the nitrile hydratase from the clone shown therein was substituted with Trp.

Example 50

Construction (89) of the Substituted Amino Acid Having Nitrile Hydratase Activity For the substitution with Glu for the 186$^{th}$ Leu in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 90 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 89 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 89, in which it is known that the 186$^{th}$ Leu in the β-subunit of the nitrile hydratase from the clone shown therein was substituted with Glu.

TABLE 89

| Clone Number | Mutated Site (in β-subunit) | Change in Amino Acid Sequence Before Substitution | Change in Amino Acid Sequence After Substitution | Change in Base Sequence Before Substitution | Change in Base Sequence After Substitution |
| --- | --- | --- | --- | --- | --- |
| No. 89 | 186$^{th}$ position in β-subunit | Leu | Glu | CTG | GAG |

TABLE 90

| Clone Number | Mutated Site (in β-subunit) | Change in Amino Acid Sequence Before Substitution | Change in Amino Acid Sequence After Substitution | Change in Base Sequence Before Substitution | Change in Base Sequence After Substitution |
| --- | --- | --- | --- | --- | --- |
| No. 90 | 186$^{th}$ position in β-subunit | Leu | Asp | CTG | GAT |

Example 51

Construction (90) of the Substituted Amino Acid Having Nitrile Hydratase Activity For the substitution with Asp for the 186$^{th}$ Leu in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 µl in total comprising 50 pmols of the primer having the sequence as forth in SEQ ID No: 91 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one. PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 90 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 90, in which it is known that the 186$^{th}$ Leu in the β-subunit of the nitrile hydratase from the clone shown therein was substituted with Asp.

Example 52

Construction (91) of the Substituted Amino Acid Having Nitrile Hydratase Activity For the substitution with Lys for the 186$^{th}$ Leu in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 µl in total comprising 50 pmols of the primer having the sequence as forth in SEQ ID No: 92 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 91 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 91, in which it is known that the 186$^{th}$ Leu in the β-subunit of the nitrile hydratase from the clone shown therein was substituted with Lys.

TABLE 91

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 91 | 186$^{th}$ position in β-subunit | Leu | Lys | CTG | AAG |

TABLE 92

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 92 | 186$^{th}$ position in β-subunit | Leu | Arg | CTG | CGG |

Example 53

Construction (92) of the Substituted Amino Acid Having Nitrile Hydratase Activity For the substitution with Arg for the 186$^{th}$ Leu in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 93 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 92 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 92, in which it is known that the 186$^{th}$ Leu in the β-subunit of the nitrile hydratase from the clone shown therein was substituted with Arg.

Example 54

Construction (93) of the Substituted Amino Acid Having Nitrile Hydratase Activity For the substitution with Asn for the 186$^{th}$ Leu in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 μl in total comprising 50 pmols of the primer having the sequence as forth in SEQ ID No: 94 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 93 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 93, in which it is known that the 186$^{th}$ Leu in the β-subunit of the nitrile hydratase from the clone shown therein was substituted with Asn.

TABLE 93

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 93 | 186$^{th}$ position in β-subunit | Leu | Asn | CTG | AAC |

TABLE 94

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 94 | 186$^{th}$ position in β-subunit | Leu | Ser | CTG | TCG |

Example 55

Construction (94) of the Substituted Amino Acid Having Nitrile Hydratase Activity For the substitution with Ser for the 186$^{th}$ Leu in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 µl in total comprising 50 pmols of the primer having the sequence as forth in SEQ ID No: 95 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 94 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 94, in which it is known that the 186$^{th}$ Leu in the β-subunit of the nitrile hydratase from the clone shown therein was substituted with Ser.

Example 56

Construction (95) of the Substituted Amino Acid Having Nitrile Hydratase Activity For the substitution with Gly for the 186$^{th}$ Leu in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 µl in total comprising 50 pmols of the primer having the sequence as forth in SEQ ID No: 96 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 95 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 95, in which it is known that the 186$^{th}$ Leu in the β-subunit of the nitrile hydratase from the clone shown therein was substituted with Gly.

TABLE 95

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 95 | 186th position in β-subunit | Leu | Gly | CTG | GGG |

TABLE 96

| Clone Number | Mutated Site (in β-subunit) | Change in Amino Acid Sequence | | Change in Base Sequence | |
|---|---|---|---|---|---|
| | | Before Substitution | After Substitution | Before Substitution | After Substitution |
| No. 96 | 217th position in β-subunit | Asp | Gly | GAC | GGC |

Example 57

Construction (96) of the Substituted Amino Acid Having Nitrile Hydratase Activity For the substitution with Gly for the 217th Asp in the β-subunit, using the plasmid DNA pPT-DB1 as the template, the plasmid DNA pPT-DB1 was subjected to introduction of site-specific mutation in the same manner as in Example 1.

Using 10 ng of the plasmid DNA pPT-DB1 as prepared in Example 1 as the template, PCRs of two different types were carried out. For the PCR reaction No. 1, a reaction system of 50 µl in total comprising 50 pmols of the primer having the sequence as forth in SEQ ID No: 97 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 96 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 96, in which it is known that the 217th Asp in the β-subunit of the nitrile hydratase from the clone shown therein was substituted with Gly.

Example 58

Construction (97) of the Substituted Amino Acid Having Nitrile Hydratase Activity This is to demonstrate that the mutant with the substituted amino acid sequence comprising both of the mutated position from the clone No. 40 (where the 36th Thr in the α-subunit was substituted with Met) and that from the clone No. 11 (where the 126th Phe in the α-subunit was substituted with Tyr) still had the nitrile hydratase activity.

10 ml of a liquid LB medium was put into a 30 ml test tube, and sterilized by autoclaving at 121° C. for 20 minutes. Ampicillin was added to this medium to have a final concentration of 100 µg/ml. On the medium, one platinum loop of the cells of the clone No. 11 as prepared in Reference Example 11 was inoculated and incubated therein at 37° C. for about 20 hours with stirring at 300 rpm. 1 ml of the resulting culture was put into a suitable centrifugal tube, and this was subjected to centrifugation (15,000 rpm, 5 minutes) to separate the cells from the culture. The plasmid DNA was prepared from the cells by alkaline SDS extraction.

Using 10 ng of the prepared plasmid DNA as the template, PCRs of two different types were carried out. For the PCR reaction No. 1, a reaction system of 50 µl in total comprising 50 pmols of the primer having the sequence as forth in SEQ ID No: 41 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 97 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 97, in which it is known that the 36$^{th}$ Thr in the α-subunit in the wild nitrile hydratase was substituted with Met and the 126$^{th}$ Phe in the same was substituted with Tyr.

TABLE 97

| Clone Number | Mutated Site (in α-subunit) | Change in Amino Acid Sequence | | Change in Base Sequence | |
| --- | --- | --- | --- | --- | --- |
| | | Wild Type | Mutant | Wild Type | Mutant |
| No. 97 | 36$^{th}$ position in α-subunit | Thr | Met | ACG | ATG |
| | 126$^{th}$ position in α-subunit | Phe | Tyr | TTC | TAC |

Example 59

Construction (98) of the Substituted Amino Acid Having Nitrile Hydratase Activity This is to demonstrate that the mutant with the substituted amino acid sequence comprising both of the mutated position from the clone No. 42 (where the 148$^{th}$ Gly in the α-subunit was substituted with Asp) and that from the clone No. 43 (where the 204$^{th}$ Val in the α-subunit was substituted with Arg) still had the nitrile hydratase activity.

10 ml of a liquid LB medium was put into a 30 ml test tube, and sterilized by autoclaving at 121° C. for 20 minutes. Ampicillin was added to this medium to have a final concentration of 100 μg/ml. On the medium, one platinum loop of the cells of the clone No. 43 as prepared in Example 4 was inoculated and incubated therein at 37° C. for about 20 hours with stirring at 300 rpm. 1 ml of the resulting culture was put into a suitable centrifugal tube, and this was subjected to centrifugation (15,000 rpm, 5 minutes) to separate the cells from the culture. The plasmid DNA was prepared from the cells by alkaline SDS extraction.

Using 10 ng of the prepared plasmid DNA as the template, PCRs of two different types were carried out. For the PCR reaction No. 1, a reaction system of 50 μl in total comprising 50 pmols of the primer having the sequence as forth in SEQ ID No: 43 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 98 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 98, in which it is known that the 148$^{th}$ Gly in the α-subunit in the wild nitrile hydratase was substituted with Asp and the 204$^{th}$ Val in the same was substituted with Arg.

TABLE 98

| Clone Number | Mutated Site (in α-subunit) | Change in Amino Acid Sequence | | Change in Base Sequence | |
| --- | --- | --- | --- | --- | --- |
| | | Wild Type | Mutant | Wild Type | Mutant |
| No. 98 | 148$^{th}$ position in α-subunit | Gly | Asp | GGC | GAC |
| | 204$^{th}$ position in α-subunit | Val | Arg | GTC | CGC |

Example 60

Construction (99) of the Substituted Amino Acid Having Nitrile Hydratase Activity This is to demonstrate that the mutant with the substituted amino acid sequence comprising both of the mutated position from the clone No. 77 (where the 51$^{st}$ Phe in the β-subunit was substituted with Val) and that from the clone No. 20 (where the 108$^{th}$ Glu in the β-subunit was substituted with Asp) still had the nitrile hydratase activity.

10 ml of a liquid LB medium was put into a 30 ml test tube, and sterilized by autoclaving at 121° C. for 20 minutes. Ampicillin was added to this medium to have a final concentration of 100 μg/ml. On the medium, one platinum loop of the cells of the clone No. 20 as prepared in Reference Example 20 was inoculated and incubated therein at 37° C. for about 20 hours with stirring at 300 rpm. 1 ml of the resulting culture was put into a suitable centrifugal tube, and this was subjected to centrifugation (15,000 rpm, 5 minutes) to separate the cells from the culture. The plasmid DNA was prepared from the cells by alkaline SDS extraction.

Using 10 ng of the prepared plasmid DNA as the template, PCRs of two different types were carried out. For the PCR reaction No. 1, a reaction system of 50 μl in total comprising 50 pmols of the primer having the sequence as forth in SEQ ID No: 78 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 99 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 99, in which it is known that the $51^{st}$ Phe in the β-subunit in the wild nitrile hydratase was substituted with Val and the $108^{th}$ Glu in the same was substituted with Asp.

TABLE 99

| Clone Number | Mutated Site (in β-subunit) | Change in Amino Acid Sequence | | Change in Base Sequence | |
|---|---|---|---|---|---|
| | | Wild Type | Mutant | Wild Type | Mutant |
| No. 99 | $51^{st}$ position in β-subunit | Phe | Val | TTC | GTC |
| | $108^{th}$ position in β-subunit | Glu | Asp | GAG | GAT |

Reference Example 40

Construction (100) of the Substituted Amino Acid Having Nitrile Hydratase Activity This is to demonstrate that the mutant with the substituted amino acid sequence comprising both of the mutated position from the clone No. 20 (where the $108^{th}$ Glu in the β-subunit was substituted with Asp) and that from the clone No. 30 (where the $200^{th}$ Ala in the β-subunit was substituted with Glu) still had the nitrile hydratase activity.

10 ml of a liquid LB medium was put into a 30 ml test tube, and sterilized by autoclaving at 121° C. for 20 minutes. Ampicillin was added to this medium to have a final concentration of 100 μg/ml. On the medium, one platinum loop of the cells of the clone No. 30 as prepared in Reference Example 30 was inoculated and incubated therein at 37° C. for about 20 hours with stirring at 300 rpm. 1 ml of the resulting culture was put into a suitable centrifugal tube, and this was subjected to centrifugation (15,000 rpm, 5 minutes) to separate the cells from the culture. The plasmid DNA was prepared from the cells by alkaline SDS extraction.

Using 10 ng of the prepared plasmid DNA as the template, PCRs of two different types were carried out. For the PCR reaction No. 1, a reaction system of 50 μl in total comprising 50 pmols of the primer having the sequence as forth in SEQ ID No: 29 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 100 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 100, in which it is known that the $108^{th}$ Glu in the β-subunit in the wild nitrile hydratase was substituted with Asp and the $200^{th}$ Ala in the same was substituted with Glu.

TABLE 100

| Clone Number | Mutated Site (in β-subunit) | Change in Amino Acid Sequence | | Change in Base Sequence | |
|---|---|---|---|---|---|
| | | Wild Type | Mutant | Wild Type | Mutant |
| No. 100 | $108^{th}$ position in β-subunit | Glu | Asp | GAG | GAT |
| | $200^{th}$ position in β-subunit | Ala | Glu | GCC | GAC |

Example 61

Construction (101) of the Substituted Amino Acid Having Nitrile Hydratase Activity This is to demonstrate that the mutant with the substituted amino acid sequence comprising both of the mutated position from the clone No. 82 (where the $118^{th}$ Phe in the β-subunit was substituted with Val) and that from the clone No. 30 (where the $200^{th}$ Ala in the β-subunit was substituted with Glu) still had the nitrile hydratase activity.

10 ml of a liquid LB medium was put into a 30 ml test tube, and sterilized by autoclaving at 121° C. for 20 minutes. Ampicillin was added to this medium to have a final concentration of 100 μg/ml. On the medium, one platinum loop of the cells of the clone No. 30 as prepared in Reference Example 30 was inoculated and incubated therein at 37° C. for about 20 hours with stirring at 300 rpm. 1 ml of the resulting culture was put into a suitable centrifugal tube, and this was subjected to centrifugation (15,000 rpm, 5 minutes) to separate the cells from the culture. The plasmid DNA was prepared from the cells by alkaline SDS extraction.

Using 10 ng of the prepared plasmid DNA as the template, PCRs of two different types were carried out. For the PCR reaction No. 1, a reaction system of 50 µl in total comprising 50 pmols of the primer having the sequence as forth in SEQ ID No: 83 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 101 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 101, in which it is known that the $118^{th}$ Phe in the β-subunit in the wild nitrile hydratase was substituted with Val and the $200^{th}$ Ala in the same was substituted with Glu.

TABLE 101

| Clone Number | Mutated Site (in β-subunit) | Change in Amino Acid Sequence | | Change in Base Sequence | |
|---|---|---|---|---|---|
| | | Wild Type | Mutant | Wild Type | Mutant |
| No. 101 | $118^{th}$ position in β-subunit | Phe | Val | TTC | GTC |
| | $200^{th}$ position in β-subunit | Ala | Glu | GCC | GAC |

Example 62

Construction (102) of the Substituted Amino Acid Having Nitrile Hydratase Activity This is to demonstrate that the mutant with the substituted amino acid sequence comprising both of the mutated position from the clone No. 88 (where the $160^{th}$ Arg in the β-subunit was substituted with Trp) and that from the clone No. 92 (where the $186^{th}$ Leu in the β-subunit was substituted with Arg) still had the nitrile hydratase activity.

10 ml of a liquid LB medium was put into a 30 ml test tube, and sterilized by autoclaving at 121° C. for 20 minutes. Ampicillin was added to this medium to have a final concentration of 100 µg/ml. On the medium, one platinum loop of the cells of the clone No. 92 as prepared in Example 53 was inoculated and incubated therein at 37° C. for about 20 hours with stirring at 300 rpm. 1 ml of the resulting culture was put into a suitable centrifugal tube, and this was subjected to centrifugation (15,000 rpm, 5 minutes) to separate the cells from the culture. The plasmid DNA was prepared from the cells by alkaline SDS extraction.

Using 10 ng of the prepared plasmid DNA as the template, PCRs of two different types were carried out. For the PCR reaction No. 1, a reaction system of 50 µl in total comprising 50 pmols of the primer having the sequence as forth in SEQ ID No: 89 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 µl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 µl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 102 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 102, in which it is known that the $160^{th}$ Arg in the β-subunit in the wild nitrile hydratase was substituted with Trp and the $186^{th}$ Leu in the same was substituted with Arg.

TABLE 102

| Clone Number | Mutated Site (in β-subunit) | Change in Amino Acid Sequence | | Change in Base Sequence | |
|---|---|---|---|---|---|
| | | Wild Type | Mutant | Wild Type | Mutant |
| No. 102 | $160^{th}$ position in β-subunit | Arg | Trp | CGG | TGG |
| | $186^{th}$ position in β-subunit | Leu | Arg | CTG | CGG |

Example 63

Construction (103) of the Substituted Amino Acid Having Nitrile Hydratase Activity This is to demonstrate that the mutant with the substituted amino acid sequence comprising both of the mutated position from the clone No. 2 (where the $6^{th}$ Leu in the α-subunit was substituted with Thr) and that from the clone No. 97 (where the 36$^{th}$ Thr in the α-subunit was substituted with Met and the 126$^{th}$ Phe in the α-subunit was substituted with Tyr) still had the nitrile hydratase activity.

10 ml of a liquid LB medium was put into a 30 ml test tube, and sterilized by autoclaving at 121° C. for 20 minutes. Ampicillin was added to this medium to have a final concentration of 100 μg/ml. On the medium, one platinum loop of the cells of the clone No. 97 as prepared in Example 58 was inoculated and incubated therein at 37° C. for about 20 hours with stirring at 300 rpm. 1 ml of the resulting culture was put into a suitable centrifugal tube, and this was subjected to centrifugation (15,000 rpm, 5 minutes) to separate the cells from the culture. The plasmid DNA was prepared from the cells by alkaline SDS extraction.

Using 10 ng of the prepared plasmid DNA as the template, PCRs of two different types were carried out. For the PCR reaction No. 1, a reaction system of 50 μl in total comprising 50 pmols of the primer having the sequence as forth in SEQ ID No: 11 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 103 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 103, in which it is known that the 6$^{th}$ Leu in the α-subunit in the wild nitrile hydratase was substituted with Thr, the 36$^{th}$ Thr in the same was substituted with Met and the 126$^{th}$ Phe in the same was substituted with Tyr.

TABLE 103

| Clone Number | Mutated Site (in α-subunit) | Change in Amino Acid Sequence | | Change in Base Sequence | |
|---|---|---|---|---|---|
| | | Wild Type | Mutant | Wild Type | Mutant |
| No. 103 | 6$^{th}$ position in α-subunit | Leu | Thr | CTG | ACG |
| | 36$^{th}$ position in α-subunit | Thr | Met | ACG | ATG |

TABLE 103-continued

| Clone Number | Mutated Site (in α-subunit) | Change in Amino Acid Sequence | | Change in Base Sequence | |
|---|---|---|---|---|---|
| | | Wild Type | Mutant | Wild Type | Mutant |
| | 126$^{th}$ position in α-subunit | Phe | Tyr | TTC | TAC |

Example 64

Construction (104) of the Substituted Amino Acid Having Nitrile Hydratase Activity This is to demonstrate that the mutant with the substituted amino acid sequence comprising both of the mutated position from the clone No. 41 (where the 71$^{st}$ Arg in the α-subunit was substituted with His) and that from the clone No. 32 (where the 19$^{th}$ Ala in the α-subunit was substituted with Val and the 126$^{th}$ Phe in the α-subunit was substituted with Tyr) still had the nitrile hydratase activity.

10 ml of a liquid LB medium was put into a 30 ml test tube, and sterilized by autoclaving at 121° C. for 20 minutes. Ampicillin was added to this medium to have a final concentration of 100 μg/ml. On the medium, one platinum loop of the cells of the clone No. 32 as prepared in Reference Example 32 was inoculated and incubated therein at 37° C. for about 20 hours with stirring at 300 rpm. 1 ml of the resulting culture was put into a suitable centrifugal tube, and this was subjected to centrifugation (15,000 rpm, 5 minutes) to separate the cells from the culture. The plasmid DNA was prepared from the cells by alkaline SDS extraction.

Using 10 ng of the prepared plasmid DNA as the template, PCRs of two different types were carried out. For the PCR reaction No. 1, a reaction system of 50 μl in total comprising 50 pmols of the primer having the sequence as forth in SEQ ID No: 42 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 104 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 104, in which it is known that the 19$^{th}$ Ala in the α-subunit in the wild nitrile hydratase was substituted with Val, the 71$^{st}$ Arg in the same was substituted with His and the 126$^{th}$ Phe in the same was substituted with Tyr.

TABLE 104

| Clone Number | Mutated Site (in α-subunit) | Change in Amino Acid Sequence | | Change in Base Sequence | |
|---|---|---|---|---|---|
| | | Wild Type | Mutant | Wild Type | Mutant |
| No. 104 | 19$^{th}$ position in α-subunit | Ala | Val | GCG | GTG |
| | 71$^{st}$ position in α-subunit | Arg | His | CGT | CAT |
| | 126$^{th}$ position in α-subunit | Phe | Tyr | TTC | TAC |

Example 65

Construction (105) of the Substituted Amino Acid Having Nitrile Hydratase Activity This is to demonstrate that the mutant with the substituted amino acid sequence comprising both of the mutated position from the clone No. 40 (where the 36$^{th}$ Thr in the α-subunit was substituted with Met) and that from the clone No. 98 (where the 148$^{th}$ Gly in the α-subunit was substituted with Asp and the 204$^{th}$ Val in the α-subunit was substituted with Arg) still had the nitrile hydratase activity.

10 ml of a liquid LB medium was put into a 30 ml test tube, and sterilized by autoclaving at 121° C. for 20 minutes. Ampicillin was added to this medium to have a final concentration of 100 μg/ml. On the medium, one platinum loop of the cells of the clone No. 98 as prepared in Example 59 was inoculated and incubated therein at 37° C. for about 20 hours with stirring at 300 rpm. 1 ml of the resulting culture was put into a suitable centrifugal tube, and this was subjected to centrifugation (15,000 rpm, 5 minutes) to separate the cells from the culture. The plasmid DNA was prepared from the cells by alkaline SDS extraction.

Using 10 ng of the prepared plasmid DNA as the template, PCRs of two different types were carried out. For the PCR reaction No. 1, a reaction system of 50 μl in total comprising 50 pmols of the primer having the sequence as forth in SEQ ID No: 41 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 105 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 105, in which it is known that the 36$^{th}$ Thr in the α-subunit in the wild nitrile hydratase was substituted with Met, the 148$^{th}$ Gly in the same was substituted with Asp and the 204$^{th}$ Val in the same was substituted with Arg.

TABLE 105

| Clone Number | Mutated Site (in α-subunit) | Change in Amino Acid Sequence | | Change in Base Sequence | |
|---|---|---|---|---|---|
| | | Wild Type | Mutant | Wild Type | Mutant |
| No. 105 | 36$^{th}$ position in α-subunit | Thr | Met | ACG | ATG |
| | 148$^{th}$ position in α-subunit | Gly | Asp | GGC | GAC |
| | 204$^{th}$ position in α-subunit | Val | Arg | GTC | CGC |

Example 66

Construction (106) of the Substituted Amino Acid Having Nitrile Hydratase Activity This is to demonstrate that the mutant with the substituted amino acid sequence comprising both of the mutated position from the clone No. 47 (where the 10$^{th}$ Thr in the β-subunit was substituted with Asp) and that from the clone No. 101 (where the 118$^{th}$ Phe in the β-subunit was substituted with Val and the 200$^{th}$ Ala in the β-subunit was substituted with Glu) still had the nitrile hydratase activity.

10 ml of a liquid LB medium was put into a 30 ml test tube, and sterilized by autoclaving at 121° C. for 20 minutes. Ampicillin was added to this medium to have a final concentration of 100 μg/ml. On the medium, one platinum loop of the cells of the clone No. 101 as prepared in Example 61 was inoculated and incubated therein at 37° C. for about 20 hours with stirring at 300 rpm. 1 ml of the resulting culture was put into a suitable centrifugal tube, and this was subjected to centrifugation (15,000 rpm, 5 minutes) to separate the cells from the culture. The plasmid DNA was prepared from the cells by alkaline SDS extraction.

Using 10 ng of the prepared plasmid DNA as the template, PCRs of two different types were carried out. For the PCR reaction No. 1, a reaction system of 50 μl in total comprising 50 pmols of the primer having the sequence as forth in SEQ ID No: 48 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No.

2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 106 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 106, in which it is known that the $10^{th}$ Thr in the β-subunit in the wild nitrile hydratase was substituted with Asp, the $118^{th}$ Phe in the same was substituted with Val and the $200^{th}$ Ala in the same was substituted with Glu.

TABLE 106

| Clone Number | Mutated Site (in β-subunit) | Change in Amino Acid Sequence | | Change in Base Sequence | |
| --- | --- | --- | --- | --- | --- |
| | | Wild Type | Mutant | Wild Type | Mutant |
| No. 106 | $10^{th}$ position in β-subunit | Thr | Asp | ACC | GAC |
| | $118^{th}$ position in β-subunit | Phe | Val | TTC | GTC |
| | $200^{th}$ position in β-subunit | Ala | Glu | GCC | GAC |

Example 67

Construction (107) of the Substituted Amino Acid Having Nitrile Hydratase Activity This is to demonstrate that the mutant with the substituted amino acid sequence comprising both of the mutated position from the clone No. 56 (where the $37^{th}$ Phe in the β-subunit was substituted with Leu) and that from the clone No. 100 (where the $108^{th}$ Glu in the β-subunit was substituted with Asp and the $200^{th}$ Ala in the β-subunit was substituted with Glu) still had the nitrile hydratase activity.

10 ml of a liquid LB medium was put into a 30 ml test tube, and sterilized by autoclaving at 121° C. for 20 minutes. Ampicillin was added to this medium to have a final concentration of 100 μg/ml. On the medium, one platinum loop of the cells of the clone No. 100 as prepared in Reference Example 40 was inoculated and incubated therein at 37° C. for about 20 hours with stirring at 300 rpm. 1 ml of the resulting culture was put into a suitable centrifugal tube, and this was subjected to centrifugation (15,000 rpm, 5 minutes) to separate the cells from the culture. The plasmid DNA was prepared from the cells by alkaline SDS extraction.

Using 10 ng of the prepared plasmid DNA as the template, PCRs of two different types were carried out. For the PCR reaction No. 1, a reaction system of 50 μl in total comprising 50 pmols of the primer having the sequence as forth in SEQ ID No: 57 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 107 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 107, in which it is known that the $37^{th}$ Phe in the β-subunit in the wild nitrile hydratase was substituted with Leu, the $108^{th}$ Glu in the same was substituted with Asp and the $200^{th}$ Ala in the same was substituted with Glu.

TABLE 107

| Clone Number | Mutated Site (in β-subunit) | Change in Amino Acid Sequence | | Change in Base Sequence | |
| --- | --- | --- | --- | --- | --- |
| | | Wild Type | Mutant | Wild Type | Mutant |
| No. 107 | $37^{th}$ position in β-subunit | Phe | Leu | TTC | CTC |
| | $108^{th}$ position in β-subunit | Glu | Asp | GAG | GAT |
| | $200^{th}$ position in β-subunit | Ala | Glu | GCC | GAC |

Example 68

Construction (108) of the Substituted Amino Acid Having Nitrile Hydratase Activity This is to demonstrate that the mutant with the substituted amino acid sequence comprising both of the mutated position from the clone No. 58 (where the $37^{th}$ Phe in the β-subunit was substituted with Val) and that from the clone No. 100 (where the $108^{th}$ Glu in the β-subunit was substituted with Asp and the $200^{th}$ Ala in the β-subunit was substituted with Glu) still had the nitrile hydratase activity.

10 ml of a liquid LB medium was put into a 30 ml test tube, and sterilized by autoclaving at 121° C. for 20 minutes. Ampicillin was added to this medium to have a final concentration of 100 μg/ml. On the medium, one platinum loop of the cells of the clone No. 100 as prepared in Reference Example 40 was inoculated and incubated therein at 37° C. for about 20 hours with stirring at 300 rpm. 1 ml of the resulting culture was put into a suitable centrifugal tube, and this was subjected to centrifugation (15,000 rpm, 5 minutes) to separate the cells from the culture. The plasmid DNA was prepared from the cells by alkaline SDS extraction.

Using 10 ng of the prepared plasmid DNA as the template, PCRs of two different types were carried out. For the PCR reaction No. 1, a reaction system of 50 μl in total comprising 50 pmols of the primer having the sequence as forth in SEQ ID No: 59 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 108 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 108, in which it is known that the $37^{th}$ Phe in the β-subunit in the wild nitrile hydratase was substituted with Val, the $108^{th}$ Glu in the same was substituted with Asp and the $200^{th}$ Ala in the same was substituted with Glu.

TABLE 108

| Clone Number | Mutated Site (in β-subunit) | Change in Amino Acid Sequence | | Change in Base Sequence | |
|---|---|---|---|---|---|
| | | Wild Type | Mutant | Wild Type | Mutant |
| No. 108 | $37^{th}$ position in β-subunit | Phe | Val | TTC | GTC |
| | $108^{th}$ position in β-subunit | Glu | Asp | GAG | GAT |
| | $200^{th}$ position in β-subunit | Ala | Glu | GCC | GAC |

Example 69

Construction (109) of the Substituted Amino Acid Having Nitrile Hydratase Activity This is to demonstrate that the mutant with the substituted amino acid sequence comprising both of the mutated position from the clone No. 63 (where the $41^{st}$ Phe in the β-subunit was substituted with Ile) and that from the clone No. 99 (where the $51^{st}$ Phe in the β-subunit was substituted with Val and the $108^{th}$ Glu in the β-subunit was substituted with Asp) still had the nitrile hydratase activity.

10 ml of a liquid LB medium was put into a 30 ml test tube, and sterilized by autoclaving at 121° C. for 20 minutes. Ampicillin was added to this medium to have a final concentration of 100 μg/ml. On the medium, one platinum loop of the cells of the clone No. 99 as prepared in Example 60 was inoculated and incubated therein at 37° C. for about 20 hours with stirring at 300 rpm. 1 ml of the resulting culture was put into a suitable centrifugal tube, and this was subjected to centrifugation (15,000 rpm, 5 minutes) to separate the cells from the culture. The plasmid DNA was prepared from the cells by alkaline SDS extraction.

Using 10 ng of the prepared plasmid DNA as the template, PCRs of two different types were carried out. For the PCR reaction No. 1, a reaction system of 50 μl in total comprising 50 pmols of the primer having the sequence as forth in SEQ ID No: 64 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 109 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 109, in which it is known that the $41^{st}$ Phe in the β-subunit in the wild nitrile hydratase was substituted with Ile, the $51^{st}$ Phe in the same was substituted with Val and the $108^{th}$ Glu in the same was substituted with Asp.

TABLE 109

| Clone Number | Mutated Site (in β-subunit) | Change in Amino Acid Sequence | | Change in Base Sequence | |
|---|---|---|---|---|---|
| | | Wild Type | Mutant | Wild Type | Mutant |
| No. 109 | 41$^{st}$ position in β-subunit | Phe | Ile | TTC | ATC |
| | 51$^{st}$ position in β-subunit | Phe | Val | TTC | GTC |
| | 108$^{th}$ position in β-subunit | Glu | Asp | GAG | GAT |

Example 70

Construction (110) of the Substituted Amino Acid Having Nitrile Hydratase Activity This is to demonstrate that the mutant with the substituted amino acid sequence comprising both of the mutated position from the clone No. 68 (where the 46$^{th}$ Met in the β-subunit was substituted with Lys) and that from the clone No. 37 (where the 108$^{th}$ Glu in the β-subunit was substituted with Arg and the 212$^{th}$ Ser in the β-subunit was substituted with Tyr) still had the nitrile hydratase activity.

10 ml of a liquid LB medium was put into a 30 ml test tube, and sterilized by autoclaving at 121° C. for 20 minutes. Ampicillin was added to this medium to have a final concentration of 100 μg/ml. On the medium, one platinum loop of the cells of the clone No. 37 as prepared in Reference Example 37 was inoculated and incubated therein at 37° C. for about 20 hours with stirring at 300 rpm. 1 ml of the resulting culture was put into a suitable centrifugal tube, and this was subjected to centrifugation (15,000 rpm, 5 minutes) to separate the cells from the culture. The plasmid DNA was prepared from the cells by alkaline SDS extraction.

Using 10 ng of the prepared plasmid DNA as the template, PCRs of two different types were carried out. For the PCR reaction No. 1, a reaction system of 50 μl in total comprising 50 pmols of the primer having the sequence as forth in SEQ ID No: 69 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 110 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 110, in which it is known that the 46$^{th}$ Met in the β-subunit in the wild nitrile hydratase was substituted with Lys, the 108$^{th}$ Glu in the same was substituted with Arg and the 212$^{th}$ Ser in the same was substituted with Tyr.

TABLE 110

| Clone Number | Mutated Site (in β-subunit) | Change in Amino Acid Sequence | | Change in Base Sequence | |
|---|---|---|---|---|---|
| | | Wild Type | Mutant | Wild Type | Mutant |
| No. 110 | 46$^{th}$ position in β-subunit | Met | Lys | ATG | AAG |
| | 108$^{th}$ position in β-subunit | Glu | Arg | GAG | CGG |
| | 212$^{th}$ position in β-subunit | Ser | Tyr | TCC | TAC |

Example 71

Construction (111) of the Substituted Amino Acid Having Nitrile Hydratase Activity This is to demonstrate that the mutant with the substituted amino acid sequence comprising both of the mutated position from the clone No. 72 (where the 48$^{th}$ Leu in the β-subunit was substituted with Val) and that from the clone No. 37 (where the 108$^{th}$ Glu in the β-subunit was substituted with Arg and the 212$^{th}$ Ser in the β-subunit was substituted with Tyr) still had the nitrile hydratase activity.

10 ml of a liquid LB medium was put into a 30 ml test tube, and sterilized by autoclaving at 121° C. for 20 minutes. Ampicillin was added to this medium to have a final concentration of 100 μg/ml. On the medium, one platinum loop of the cells of the clone No. 37 as prepared in Reference Example 37 was inoculated and incubated therein at 37° C. for about 20 hours with stirring at 300 rpm. 1 ml of the resulting culture was put into a suitable centrifugal tube, and this was subjected to centrifugation (15,000 rpm, 5 minutes) to separate the cells from the culture. The plasmid DNA was prepared from the cells by alkaline SDS extraction.

Using 10 ng of the prepared plasmid DNA as the template, PCRs of two different types were carried out. For the PCR reaction No. 1, a reaction system of 50 μl in total comprising 50 pmols of the primer having the sequence as forth in SEQ ID No: 73 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 111 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 111, in which it is known that the 48$^{th}$ Leu in the β-subunit in the wild nitrile hydratase was substituted with Val, the 108$^{th}$ Glu in the same was substituted with Arg and the 212$^{th}$ Ser in the same was substituted with Tyr.

TABLE 111

| Clone Number | Mutated Site (in β-subunit) | Change in Amino Acid Sequence | | Change in Base Sequence | |
|---|---|---|---|---|---|
| | | Wild Type | Mutant | Wild Type | Mutant |
| No. 111 | 48$^{th}$ position in β-subunit | Leu | Val | CTG | GTG |
| | 108$^{th}$ position in β-subunit | Glu | Arg | GAG | CGG |
| | 212$^{th}$ position in β-subunit | Ser | Tyr | TCC | TAC |

Example 72

Construction (112) of the Substituted Amino Acid Having Nitrile Hydratase Activity This is to demonstrate that the mutant with the substituted amino acid sequence comprising both of the mutated position from the clone No. 85 (where the 127$^{th}$ Leu in the β-subunit was substituted with Ser) and that from the clone No. 102 (where the 160$^{th}$ Arg in the β-subunit was substituted with Trp and the 186$^{th}$ Leu in the β-subunit was substituted with Arg) still had the nitrile hydratase activity.

10 ml of a liquid LB medium was put into a 30 ml test tube, and sterilized by autoclaving at 121° C. for 20 minutes. Ampicillin was added to this medium to have a final concentration of 100 μg/ml. On the medium, one platinum loop of the cells of the clone No. 102 as prepared in Example 62 was inoculated and incubated therein at 37° C. for about 20 hours with stirring at 300 rpm. 1 ml of the resulting culture was put into a suitable centrifugal tube, and this was subjected to centrifugation (15,000 rpm, 5 minutes) to separate the cells from the culture. The plasmid DNA was prepared from the cells by alkaline SDS extraction.

Using 10 ng of the prepared plasmid DNA as the template, PCRs of two different types were carried out. For the PCR reaction No. 1, a reaction system of 50 μl in total comprising 50 pmols of the primer having the sequence as forth in SEQ ID No: 86 in the Sequence Listing and 50 pmols of an M13 primer M4 (having the sequence as forth in SEQ ID No: 8 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 120 seconds. For the PCR reaction No. 2, a reaction system of 50 μl in total comprising 50 pmols of an MUT4 primer (having the sequence as forth in SEQ ID No: 9 in the Sequence Listing) and 50 pmols of an M13 primer RV (having the sequence as forth in SEQ ID No: 10 in the Sequence Listing) (for the composition of the system, the manufacturer's instructions for the kit were followed) was used, and the reaction was carried out following the same procedure as the PCR reaction No. 1. After completion of the PCR reaction Nos. 1 and 2, 5 μl of the reaction mixture was subjected to agarose gel electrophoresis (where the agarose concentration was 1.0% by weight), and an assay of the DNA amplification product was carried out, thereby it being possible to confirm the presence of an amplified DNA product. A transformant No. 112 was then obtained in completely the same manner as in Example 1.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 112, in which it is known that the 127$^{th}$ Leu in the β-subunit in the wild nitrile hydratase was substituted with Ser, the 160$^{th}$ Arg in the same was substituted with Trp and the 186$^{th}$ Leu in the same was substituted with Arg.

TABLE 112

| Clone Number | Mutated Site (in β-subunit) | Change in Amino Acid Sequence | | Change in Base Sequence | |
|---|---|---|---|---|---|
| | | Wild Type | Mutant | Wild Type | Mutant |
| No. 112 | 127$^{th}$ position in β-subunit | Leu | Ser | CTG | TCG |
| | 160$^{th}$ position in β-subunit | Arg | Trp | CGG | TGG |
| | 186$^{th}$ position in β-subunit | Leu | Arg | CTG | CGG |

Example 73

Construction (113) of the Substituted Amino Acid Having Nitrile Hydratase Activity This is to demonstrate that the mutant with the substituted amino acid sequence comprising both of the mutated position from the clone No. 34 and that from the clone No. 110 still had the nitrile hydratase activity.

10 ml of a liquid LB medium was put into a 30 ml test tube, and sterilized by autoclaving at 121° C. for 20 minutes. Ampicillin was added to this medium to have a final concentration of 100 μg/ml. On the medium, one platinum loop of the cells of the clone No. 34 as prepared in Reference Example 34 and the clone No. 110 as prepared in Example 70 was inoculated and incubated therein at 37° C. for about 20 hours with stirring at 300 rpm. 1 ml of the resulting culture was put into a suitable centrifugal tube, and this was subjected to centrifugation (15,000 rpm, 5 minutes) to separate the cells from the culture. From the cells extracted the plasmid DNA of the clone No. 34 and the plasmid DNA of the clone No. 110 through alkaline SDS extraction.

The plasmid DNA from the clone No. 110 was cleaved by means of restriction endonucleases EcoRI and NotI at the cleaving sites thereof, and then subjected to agarose gel electrophoresis (using Type VII low-melting-point agarose, manufactured by Sigma Corporation; agarose concentration of 1.0%), through which the DNA fragment of about 770 bp was cut out of the agarose gel. In the same manner, the plasmid DNA from the clone No. 34 was cleaved by means of restriction endonucleases EcoRI and NotI at the cleaving sites thereof, and then subjected to agarose gel electrophoresis (using Type VII low-melting-point agarose, manufactured by Sigma Corporation; at an agarose concentration of 0.7%), through which the DNA fragment of about 3.8 kbp was cut out of the agarose gel. Both the thus-cut agarose fragments (about 0.1 g each) were finely pulverized, then separately suspended in 1 ml of a TE solution, and kept at 55° C. for 1 hour, whereby the agarose fragments were completely melted. The resulting agarose melts were separately subjected to phenol/chloroform extraction and ethanol precipitation, to purify the DNA fragment. Finally, these were separately dissolved in 10 µl of TE.

The DNA fragment of about 770 bp obtained from the clone No. 110 and the DNA fragment of about 3.8 kbp obtained from the clone No. 34 were subjected to DNA ligation, using a DNA ligation kit (manufactured by Takara Shuzo Co., Ltd.), to construct a plasmid. This plasmid DNA was introduced into competent cells of *E. coli* HB101 (manufactured by Toyobo Co., Ltd.). Thus was obtained a transformant No. 113.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 113, in which it is known that the 6$^{th}$ Leu in the α-subunit in the wild nitrile hydratase was substituted with Thr, the 19$^{th}$ Ala in the same was substituted with Val, the 126$^{th}$ Phe in the same was substituted with Tyr, while the 46$^{th}$ Met in the β-subunit in the wild nitrile hydratase was substituted with Lys, the 108$^{th}$ Glu in the same was substituted with Arg, and the 212$^{th}$ Ser in the same was substituted with Tyr.

TABLE 113

| Clone Number | Mutated Site | Change in Amino Acid Sequence | | Change in Base Sequence | |
|---|---|---|---|---|---|
| | | Wild Type | Mutant | Wild Type | Mutant |
| No. 113 | 6$^{th}$ position in α-subunit | Leu | Thr | CTG | ACG |
| | 19$^{th}$ position in α-subunit | Ala | Val | GCG | GTG |
| | 126$^{th}$ position in α-subunit | Phe | Tyr | TTC | TAC |
| | 46$^{th}$ position in β-subunit | Met | Lys | ATG | AAG |
| | 108$^{th}$ position in β-subunit | Glu | Arg | GAG | CGG |
| | 212$^{th}$ position in β-subunit | Ser | Tyr | TCC | TAC |

Example 74

Construction (114) of the Substituted Amino Acid Having Nitrile Hydratase Activity This is to demonstrate that the mutant with the substituted amino acid sequence comprising both of the mutated position from the clone No. 34 and that from the clone No. 111 still had the nitrile hydratase activity.

10 ml of a liquid LB medium was put into a 30 ml test tube, and sterilized by autoclaving at 121° C. for 20 minutes. Ampicillin was added to this medium to have a final concentration of 100 µg/ml. On the medium, one platinum loop of the cells of the clone No. 34 as prepared in Reference Example 34 and the clone No. 111 as prepared in Example 71 was inoculated and incubated therein at 37° C. for about 20 hours with stirring at 300 rpm. 1 ml of the resulting culture was put into a suitable centrifugal tube, and this was subjected to centrifugation (15,000 rpm, 5 minutes) to separate the cells from the culture. From the cells extracted the plasmid DNA of the clone No. 34 and the plasmid DNA of the clone No. 111 through alkaline SDS extraction.

The plasmid DNA from the clone No. 111 was cleaved by means of restriction endonucleases EcoRI and NotI at the cleaving sites thereof, and then subjected to agarose gel electrophoresis (using Type VII low-melting-point agarose, manufactured by Sigma Corporation; agarose concentration of 1.0%), through which the DNA fragment of about 770 bp was cut out of the agarose gel. In the same manner, the plasmid DNA from the clone No. 34 was cleaved by means of restriction endonucleases EcoRI and NotI at the cleaving sites thereof, and then subjected to agarose gel electrophoresis (using Type VII low-melting-point agarose, manufactured by Sigma Corporation; at an agarose concentration of 0.7%), through which the DNA fragment of about 3.8 kbp was cut out of the agarose gel. Both the thus-cut agarose fragments (about 0.1 g each) were finely pulverized, then separately suspended in 1 ml of a TE solution, and kept at 55° C. for 1 hour, whereby the agarose fragments were completely melted. The resulting agarose melts were separately subjected to phenol/chloroform extraction and ethanol precipitation, to purify the DNA fragments. Finally, these were separately dissolved in 10 µl of TE.

The DNA fragment of about 770 bp obtained from the clone No. 111 and the DNA fragment of about 3.8 kbp obtained from the clone No. 34 were subjected to DNA ligation, using a DNA ligation kit (manufactured by Takara Shuzo Co., Ltd.), to construct a plasmid. This plasmid DNA was introduced into competent cells of *E. coli* HB101 (manufactured by Toyobo Co., Ltd.). Thus was obtained a transformant No. 114.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 114, in which it is known that the 6$^{th}$ Leu in the α-subunit in the wild nitrile hydratase was substituted with Thr, the 19$^{th}$ Ala in the same was substituted with Val, the 126$^{th}$ Phe in the same was substituted with Tyr, while the 48$^{th}$ Leu in the β-subunit in the wild nitrile hydratase was substituted with Val, the 108$^{th}$ Glu in the same was substituted with Arg, and the 212$^{th}$ Ser in the same was substituted with Tyr.

TABLE 114

| Clone Number | Mutated Site | Change in Amino Acid Sequence | | Change in Base Sequence | |
|---|---|---|---|---|---|
| | | Wild Type | Mutant | Wild Type | Mutant |
| No. 114 | 6th position in α-subunit | Leu | Thr | CTG | ACG |
| | 19th position in α-subunit | Ala | Val | GCG | GTG |
| | 126th position in α-subunit | Phe | Tyr | TTC | TAC |
| | 48th position in β-subunit | Leu | Val | CTG | GTG |
| | 108th position in β-subunit | Glu | Arg | GAG | CGG |
| | 212th position in β-subunit | Ser | Tyr | TCC | TAC |

Example 75

Construction (115) of the Substituted Amino Acid Having Nitrile Hydratase Activity This is to demonstrate that the mutant with the substituted amino acid sequence comprising both of the mutated position from the clone No. 35 and that from the clone No. 112 still had the nitrile hydratase activity.

10 ml of a liquid LB medium was put into a 30 ml test tube, and sterilized by autoclaving at 121° C. for 20 minutes. Ampicillin was added to this medium to have a final concentration of 100 µg/ml. On the medium, one platinum loop of the cells of the clone No. 35 as prepared in Reference Example 35 and the clone No. 112 as prepared in Example 72 was inoculated and incubated therein at 37° C. for about 20 hours with stirring at 300 rpm. 1 ml of the resulting culture was put into a suitable centrifugal tube, and this was subjected to centrifugation (15,000 rpm, 5 minutes) to separate the cells from the culture. From the cells extracted the plasmid DNA of the clone No. 35 and the plasmid DNA of the clone No. 112 through alkaline SDS extraction.

The plasmid DNA from the clone No. 112 was cleaved by means of restriction endonucleases EcoRI and NotI at the cleaving sites thereof, and then subjected to agarose gel electrophoresis (using Type VII low-melting-point agarose, manufactured by Sigma Corporation; at an agarose concentration of 1.0%), through which the DNA fragment of about 770 bp was cut out of the agarose gel. In the same manner, the plasmid DNA from the clone No. 35 was cleaved by means of restriction endonucleases EcoRI and NotI at the cleaving sites thereof, and then subjected to agarose gel electrophoresis (using Type VII low-melting-point agarose, manufactured by Sigma Corporation; at an agarose concentration of 0.7%), through which the DNA fragment of about 3.8 kbp was cut out of the agarose gel. Both the thus-cut agarose fragments (about 0.1 g each) were finely pulverized, then separately suspended in 1 ml of a TE solution, and kept at 55° C. for 1 hour, whereby the agarose fragments were completely melted. The resulting agarose melts were separately subjected to phenol/chloroform extraction and ethanol precipitation, to purify the DNA fragments. Finally, these were separately dissolved in 10 µl of TE.

The DNA fragment of about 770 bp obtained from the clone No. 112 and the DNA fragment of about 3.8 kbp obtained from the clone No. 35 were subjected to DNA ligation, using a DNA ligation kit (manufactured by Takara Shuzo Co., Ltd.), to construct a plasmid. This plasmid DNA was introduced into competent cells of E. coli HB101 (manufactured by Toyobo Co., Ltd.). Thus was obtained a transformant No. 115.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 115, in which it is known that the 6th Leu in the α-subunit in the wild nitrile hydratase was substituted with Ala, the 19th Ala in the same was substituted with Val, the 126th Phe in the same was substituted with Tyr, while the 127th Leu in the β-subunit in the wild nitrile hydratase was substituted with Ser, the 160th Arg in the same was substituted with Trp, and the 186th Leu in the same was substituted with Arg.

TABLE 115

| Clone Number | Mutated Site | Change in Amino Acid Sequence | | Change in Base Sequence | |
|---|---|---|---|---|---|
| | | Wild Type | Mutant | Wild Type | Mutant |
| No. 115 | 6th position in α-subunit | Leu | Ala | CTG | GCG |
| | 19th position in α-subunit | Ala | Val | GCG | GTG |
| | 126th position in α-subunit | Phe | Tyr | TTC | TAC |
| | 127th position in β-subunit | Leu | Ser | CTG | TCG |
| | 160th position in β-subunit | Arg | Trp | CGG | TGG |
| | 186th position in β-subunit | Leu | Arg | CTG | CGG |

Example 76

Construction (116) of the Substituted Amino Acid Having Nitrile Hydratase Activity This is to demonstrate that the mutant with the substituted amino acid sequence comprising both of the mutated position from the clone No. 103 and that from the clone No. 106 still had the nitrile hydratase activity.

10 ml of a liquid LB medium was put into a 30 ml test tube, and sterilized by autoclaving at 121° C. for 20 minutes. Ampicillin was added to this medium to have a final concentration of 100 µg/ml. On the medium, one platinum loop of the cells of the clone No. 103 as prepared in Example 63 and the clone No. 106 as prepared in Example 66 was inoculated and incubated therein at 37° C. for about 20 hours with stirring at 300 rpm. 1 ml of the resulting culture was put into a suitable centrifugal tube, and this was subjected to centrifugation (15,000 rpm, 5 minutes) to separate the cells from the culture. From the cells extracted the plasmid DNA of the clone No. 103 and the plasmid DNA of the clone No. 106 through alkaline SDS extraction.

The plasmid DNA from the clone No. 106 was cleaved by means of restriction endonucleases EcoRI and NotI at the cleaving sites thereof, and then subjected to agarose gel electrophoresis (using Type VII low-melting-point agarose, manufactured by Sigma Corporation; at an agarose concentration of 1.0%), through which the DNA fragment of about 770 bp was cut out of the agarose gel. In the same manner, the plasmid DNA from the clone No. 103 was cleaved by means of restriction endonucleases EcoRI and NotI at the cleaving sites thereof, and then subjected to agarose gel electrophoresis (using Type VII low-melting-point agarose, manufactured by Sigma Corporation; at an agarose concentration of 0.7%), through which the DNA fragment of about 3.8 kbp was cut out of the agarose gel. Both the thus-cut agarose fragments (about 0.1 g each) were finely pulverized, then separately suspended in 1 ml of a TE solution, and kept at 55° C. for 1 hour, whereby the agarose fragments were completely melted. The resulting agarose melts were separately subjected to phenol/chloroform extraction and ethanol precipitation, to purify the DNA fragments. Finally, these were separately dissolved in 10 μl of TE.

The DNA fragment of about 770 bp obtained from the clone No. 106 and the DNA fragment of about 3.8 kbp obtained from the clone No. 103 were subjected to DNA ligation, using a DNA ligation kit (manufactured by Takara Shuzo Co., Ltd.), to construct a plasmid. This plasmid DNA was introduced into competent cells of *E. coli* HB101 (manufactured by Toyobo Co., Ltd.). Thus was obtained a transformant No. 116.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 116, in which it is known that the $6^{th}$ Leu in the α-subunit in the wild nitrile hydratase was substituted with Thr, the $36^{th}$ Thr in the same was substituted with Met, the $126^{th}$ Phe in the same was substituted with Tyr, while the $10^{th}$ Thr in the β-subunit in the wild nitrile hydratase was substituted with Asp, the $118^{th}$ Phe in the same was substituted with Val, and the $200^{th}$ Ala in the same was substituted with Glu.

TABLE 116

| Clone Number | Mutated Site | Change in Amino Acid Sequence | | Change in Base Sequence | |
| --- | --- | --- | --- | --- | --- |
| | | Wild Type | Mutant | Wild Type | Mutant |
| No. 116 | $6^{th}$ position in α-subunit | Leu | Thr | CTG | ACG |
| | $36^{th}$ position in α-subunit | Thr | Met | ACG | ATG |
| | $126^{th}$ position in α-subunit | Phe | Tyr | TTC | TAC |
| | $10^{th}$ position in β-subunit | Thr | Asp | ACC | GAC |
| | $118^{th}$ position in β-subunit | Phe | Val | TTC | GTC |
| | $200^{th}$ position in β-subunit | Ala | Glu | GCC | GAC |

Example 77

Construction (117) of the Substituted Amino Acid Having Nitrile Hydratase Activity This is to demonstrate that the mutant with the substituted amino acid sequence comprising both of the mutated position from the clone No. 104 and that from the clone No. 107 still had the nitrile hydratase activity.

10 ml of a liquid LB medium was put into a 30 ml test tube, and sterilized by autoclaving at 121° C. for 20 minutes. Ampicillin was added to this medium to have a final concentration of 100 μg/ml. On the medium, one platinum loop of the cells of the clone No. 104 as prepared in Example 64 and the clone No. 107 as prepared in Example 67 was inoculated and incubated therein at 37° C. for about 20 hours with stirring at 300 rpm. 1 ml of the resulting culture was put into a suitable centrifugal tube, and this was subjected to centrifugation (15,000 rpm, 5 minutes) to separate the cells from the culture. From the cells extracted the plasmid DNA of the clone No. 104 and the plasmid DNA of the clone No. 107 through alkaline SDS extraction.

The plasmid DNA from the clone No. 107 was cleaved by means of restriction endonucleases EcoRI and NotI at the cleaving sites thereof, and then subjected to agarose gel electrophoresis (using Type VII low-melting-point agarose, manufactured by Sigma Corporation; at an agarose concentration of 1.0%), through which the DNA fragment of about 770 bp was cut out of the agarose gel. In the same manner, the plasmid DNA from the clone No. 104 was cleaved by means of restriction endonucleases EcoRI and NotI at the cleaving sites thereof, and then subjected to agarose gel electrophoresis (using Type VII low-melting-point agarose, manufactured by Sigma Corporation; at an agarose concentration of 0.7%), through which the DNA fragment of about 3.8 kbp was cut out of the agarose gel. Both the thus-cut agarose fragments (about 0.1 g each) were finely pulverized, then separately suspended in 1 ml of a TE solution, and kept at 55° C. for 1 hour, whereby the agarose fragments were completely melted. The resulting agarose melts were separately subjected to phenol/chloroform extraction and ethanol precipitation, to purify the DNA fragments. Finally, these were separately dissolved in 10 μl of TE.

The DNA fragment of about 770 bp obtained from the clone No. 107 and the DNA fragment of about 3.8 kbp obtained from the clone No. 104 were subjected to DNA ligation, using a DNA ligation kit (manufactured by Takara Shuzo Co., Ltd.), to construct a plasmid. This plasmid DNA was introduced into competent cells of *E. coli* HB101 (manufactured by Toyobo Co., Ltd.). Thus was obtained a transformant No. 117.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 117, in which it is known that the $19^{th}$ Ala in the α-subunit in the wild nitrile hydratase was substituted with Val, the $71^{st}$ Arg in the same was substituted with His, the $126^{th}$ Phe in the same was substituted with Tyr, while the $37^{th}$ Phe in the β-subunit in the wild nitrile hydratase was substituted with Leu, the $108^{th}$ Glu in the same was substituted with Asp, and the $200^{th}$ Ala in the same was substituted with Glu.

TABLE 117

| Clone Number | Mutated Site | Change in Amino Acid Sequence | | Change in Base Sequence | |
|---|---|---|---|---|---|
| | | Wild Type | Mutant | Wild Type | Mutant |
| No. 117 | 19$^{th}$ position in α-subunit | Ala | Val | GCG | GTG |
| | 71$^{st}$ position in α-subunit | Arg | His | CGT | CAT |
| | 126$^{th}$ position in α-subunit | Phe | Tyr | TTC | TAC |
| | 37$^{th}$ position in β-subunit | Phe | Leu | TTC | CTC |
| | 108$^{th}$ position in β-subunit | Glu | Asp | GAG | GAT |
| | 200$^{th}$ position in β-subunit | Ala | Glu | GCC | GAC |

Example 78

Construction (118) of the Substituted Amino Acid Having Nitrile Hydratase Activity This is to demonstrate that the mutant with the substituted amino acid sequence comprising both of the mutated position from the clone No. 104 and that from the clone No. 108 still had the nitrile hydratase activity.

10 ml of a liquid LB medium was put into a 30 ml test, tube, and sterilized by autoclaving at 121° C. for 20 minutes. Ampicillin was added to this medium to have a final concentration of 100 μg/ml. On the medium, one platinum loop of the cells of the clone No. 104 as prepared in Example 64 and the clone No. 108 as prepared in Example 68 was inoculated and incubated therein at 37° C. for about 20 hours with stirring at 300 rpm. 1 ml of the resulting culture was put into a suitable centrifugal tube, and this was subjected to centrifugation (15,000 rpm, 5 minutes) to separate the cells from the culture. From the cells extracted the plasmid DNA of the clone No. 104 and the plasmid DNA of the clone No. 108 through alkaline SDS extraction.

The plasmid DNA from the clone No. 108 was cleaved by means of restriction endonucleases EcoRI and NotI at the cleaving sites thereof, and then subjected to agarose gel electrophoresis (using Type VII low-melting-point agarose, manufactured by Sigma Corporation; at an agarose concentration of 1.0%), through which the DNA fragment of about 770 bp was cut out of the agarose gel. In the same manner, the plasmid DNA from the clone No. 104 was cleaved by means of restriction endonucleases EcoRI and NotI at the cleaving sites thereof, and then subjected to agarose gel electrophoresis (using Type VII low-melting-point agarose, manufactured by Sigma Corporation; at an agarose concentration of 0.7%), through which the DNA fragment of about 3.8 kbp was cut out of the agarose gel. Both the thus-cut agarose fragments (about 0.1 g each) were finely pulverized, then separately suspended in 1 ml of a TE solution, and kept at 55° C. for 1 hour, whereby the agarose fragments were completely melted. The resulting agarose melts were separately subjected to phenol/chloroform extraction and ethanol precipitation, to purify the DNA fragments. Finally, these were separately dissolved in 10 μl of TE.

The DNA fragment of about 770 bp obtained from the clone No. 108 and the DNA fragment of about 3.8 kbp obtained from the clone No. 104 were subjected to DNA ligation, using a DNA ligation kit (manufactured by Takara Shuzo Co., Ltd.), to construct a plasmid. This plasmid DNA was introduced into competent cells of E. coli HB101 (manufactured by Toyobo Co., Ltd.). Thus was obtained a transformant No. 118.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 118, in which it is known that the 19$^{th}$ Ala in the α-subunit in the wild nitrile hydratase was substituted with Val, the 71$^{st}$ Arg in the same was substituted with His, the 126$^{th}$ Phe in the same was substituted with Tyr, while the 37$^{th}$ Phe in the β-subunit in the wild nitrile hydratase was substituted with Val, the 108$^{th}$ Glu in the same was substituted with Asp, and the 200$^{th}$ Ala in the same was substituted with Glu.

TABLE 118

| Clone Number | Mutated Site | Change in Amino Acid Sequence | | Change in Base Sequence | |
|---|---|---|---|---|---|
| | | Wild Type | Mutant | Wild Type | Mutant |
| No. 118 | 19$^{th}$ position in α-subunit | Ala | Val | GCG | GTG |
| | 71$^{st}$ position in α-subunit | Arg | His | CGT | CAT |
| | 126$^{th}$ position in α-subunit | Phe | Tyr | TTC | TAC |
| | 37$^{th}$ position in β-subunit | Phe | Val | TTC | GTC |
| | 108$^{th}$ position in β-subunit | Glu | Asp | GAG | GAT |
| | 200$^{th}$ position in β-subunit | Ala | Glu | GCC | GAC |

Example 79

Construction (119) of the Substituted Amino Acid Having Nitrile Hydratase Activity This is to demonstrate that the mutant with the substituted amino acid sequence comprising both of the mutated position from the clone No. 105 and that from the clone No. 109 still had the nitrile hydratase activity.

10 ml of a liquid LB medium was put into a 30 ml test tube, and sterilized by autoclaving at 121° C. for 20 minutes. Ampicillin was added to this medium to have a final concentration of 100 μg/ml. On the medium, one platinum loop of the cells of the clone No. 105 as prepared in Example 65 and the clone No. 109 as prepared in Example 69 was inoculated and incubated therein at 37° C. for about 20 hours with stirring at 300 rpm. 1 ml of the resulting culture was put into a suitable centrifugal tube, and this was subjected to centrifugation (15,000 rpm, 5 minutes) to separate the cells from the culture. From the cells extracted the plasmid DNA of the clone No. 105 and the plasmid DNA of the clone No. 109 through alkaline SDS extraction.

The plasmid DNA from the clone No. 109 was cleaved by means of restriction endonucleases EcoRI and NotI at the cleaving sites thereof, and then subjected to agarose gel electrophoresis (using Type VII low-melting-point agarose, manufactured by Sigma Corporation; at an agarose concentration of 1.0%), through which the DNA fragment of about 770 bp was cut out of the agarose gel. In the same manner, the plasmid DNA from the clone No. 105 was cleaved by means of restriction endonucleases EcoRI and NotI at the cleaving sites thereof, and then subjected to agarose gel electrophoresis (using Type VII low-melting-point agarose, manufactured by Sigma Corporation; at an agarose concentration of 0.7%), through which the DNA fragment of about 3.8 kbp was cut out of the agarose gel. Both the thus-cut agarose fragments (about 0.1 g each) were finely pulverized, then separately suspended in 1 ml of a TE solution, and kept at 55° C. for 1 hour, whereby the agarose fragments were completely melted. The resulting agarose melts were separately subjected to phenol/chloroform extraction and ethanol precipitation, to purify the DNA fragments. Finally, these were separately dissolved in 10 μl of TE.

The DNA fragment of about 770 bp obtained from the clone No. 109 and the DNA fragment of about 3.8 kbp obtained from the clone No. 105 were subjected to DNA ligation, using a DNA ligation kit (manufactured by Takara Shuzo Co., Ltd.), to construct a plasmid. This plasmid DNA was introduced into competent cells of $E.\ coli$ HB101 (manufactured by Toyobo Co., Ltd.). Thus was obtained a transformant No. 119.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 119, in which it is known that the $36^{th}$ Thr in the α-subunit in the wild nitrile hydratase was substituted with Met, the $148^{th}$ Gly in the same was substituted with Asp, the $204^{th}$ Val in the same was substituted with Arg, while the $41^{st}$ Phe in the β-subunit in the wild nitrile hydratase was substituted with Ile, the $51^{st}$ Phe in the same was substituted with Val, and the $108^{th}$ Glu in the same was substituted with Asp.

TABLE 119

| Clone Number | Mutated Site | Change in Amino Acid Sequence | | Change in Base Sequence | |
|---|---|---|---|---|---|
| | | Wild Type | Mutant | Wild Type | Mutant |
| No. 119 | $36^{th}$ position in α-subunit | Thr | Met | ACG | ATG |
| | $148^{th}$ position in α-subunit | Gly | Asp | GGC | GAC |
| | $204^{th}$ position in α-subunit | Val | Arg | GTC | CGC |
| | $41^{st}$ position in β-subunit | Phe | Ile | TTC | ATC |
| | $51^{st}$ position in β-subunit | Phe | Val | TTC | GTC |
| | $108^{th}$ position in β-subunit | Glu | Asp | GAG | GAT |

Example 80

Construction (120) of the Substituted Amino Acid Having Nitrile Hydratase Activity This is to demonstrate that the mutant with the substituted amino acid sequence comprising both of the mutated position from the clone No. 98 and that from the clone No. 100 still had the nitrile hydratase activity.

10 ml of a liquid LB medium was put into a 30 ml test tube, and sterilized by autoclaving at 121° C. for 20 minutes. Ampicillin was added to this medium to have a final concentration of 100 μg/ml. On the medium, one platinum loop of the cells of the clone No. 98 as prepared in Example 59 and the clone No. 100 as prepared in Reference Example 40 was inoculated and incubated therein at 37° C. for about 20 hours with stirring at 300 rpm. 1 ml of the resulting culture was put into a suitable centrifugal tube, and this was subjected to centrifugation (15,000 rpm, 5 minutes) to separate the cells from the culture. From the cells extracted the plasmid DNA of the clone No. 98 and the plasmid DNA of the clone No. 100 through alkaline SDS extraction.

The plasmid DNA from the clone No. 100 was cleaved by means of restriction endonucleases EcoRI and NotI at the cleaving sites thereof, and then subjected to agarose gel electrophoresis (using Type VII low-melting-point agarose, manufactured by Sigma Corporation; at an agarose concentration of 1.0%), through which the DNA fragment of about 770 bp was cut out of the agarose gel. In the same manner, the plasmid DNA from the clone No. 98 was cleaved by means of restriction endonucleases EcoRI and NotI at the cleaving sites thereof, and then subjected to agarose gel electrophoresis (using Type VII low-melting-point agarose, manufactured by Sigma Corporation; at an agarose concentration of 0.7%), through which the DNA fragment of about 3.8 kbp was cut out of the agarose gel. Both the thus-cut agarose fragments (about 0.1 g each) were finely pulverized, then separately suspended in 1 ml of a TE solution, and kept at 55° C. for 1 hour, whereby the agarose fragments were completely melted. The resulting agarose melts were separately subjected to phenol/chloroform extraction and ethanol precipitation, to purify the DNA fragments. Finally, these were separately dissolved in 10 μl of TE.

The DNA fragment of about 770 bp obtained from the clone No. 100 and the DNA fragment of about 3.8 kbp obtained from the clone No. 98 were subjected to DNA ligation, using a DNA ligation kit (manufactured by Takara Shuzo Co., Ltd.), to construct a plasmid. This plasmid DNA was introduced into competent cells of $E.\ coli$ HB101 (manufactured by Toyobo Co., Ltd.). Thus was obtained a transformant No. 120.

Thereafter, the addition rate and the selectivity were determined in the same manner as in Reference Example 1, and the conversion and the selectivity were 100%, respectively.

Moreover, the plasmid was prepared from the cells by alkaline SDS extraction. Next, the base sequence of the nitrile hydratase gene was determined by the dideoxy chain termination method using a sequencing kit and an Autosequencer 373A manufactured by ABI. The results are shown in Table 120, in which it is known that the $148^{th}$ Gly in the α-subunit in the wild nitrile hydratase was substituted with Asp, the $204^{th}$ Val in the same was substituted with Arg, while the $108^{th}$ Glu in the β-subunit in the wild nitrile hydratase was substituted with Asp, and the $200^{th}$ Ala in the same was substituted with Glu.

TABLE 120

| Clone Number | Mutated Site | Change in Amino Acid Sequence | | Change in Base Sequence | |
| --- | --- | --- | --- | --- | --- |
| | | Wild Type | Mutant | Wild Type | Mutant |
| No. 120 | 148th position in α-subunit | Gly | Asp | GGC | GAC |
| | 204th position in α-subunit | Val | Arg | GTC | CGC |
| | 108th position in β-subunit | Glu | Asp | GAG | GAT |
| | 200th position in β-subunit | Ala | Glu | GCC | GAC |

Example 81

Preparation of Genomic DNA from *Rhodococcus rhodochrous* Strain J1

In a 500 ml Erlenmeyer flask with baffles, 100 ml of a medium of the following composition was prepared and sterilized by autoclaving at 121° C. for 20 minutes.

Medium composition;

Glucose: 10.0 g/L, potassium dihydrogen phosphate: 0.5 g/L, dipotassium hydrogen phosphate: 0.5 g/L, magnesium sulfate.heptahydrate: 0.5 g/L, yeast extract: 1.0 g/L, peptone: 7.5 g/L, urea: 7.5 g/L, cobalt chloride.hexahydrate: 10.0 mg/L, pH 7.2

On this medium, one platinum loop of the cells of *Rhodococcus rhodochrous* strain J1 (deposited with the above-mentioned depository authority under the deposit number of FERM BP-1478 under the Budapest Treaty for the international recognition of the deposit of microorganisms for the purposes of patent procedure and may be distributed to anyone on request) as described in Patent Document 1 was inoculated and incubated therein at 30° C. for 72 hours with stirring at 130 rpm. The cells were separated from the resulting culture by centrifugation (15,000 G×15 minutes). The cells were resuspended in 50 ml of physiological saline, and then subjected to another centrifugation, thereby wet cells being obtained.

To 2 g of the wet cells obtained above, 40 ml of an aqueous solution (pH 8.0) of 50 mM EDTA.2Na containing 0.15 M NaCl was added to prepare a cell suspension, which was boiled at 90° C. for 10 minutes. The resulting suspension was cooled to 37° C., to which was added 100 mg of egg white lysozyme, and was kept at 37° C. for 1 hour. To this, next, 30 mg of zymolylase of 20,000 U/mg was added, followed by keeping at 37° C. for 1 hour. Subsequently, 5 mg of proteinase K of 20 U/mg was added to this, followed by keeping at 37° C. for 1 hour. Further, 2 ml of 10% SDS solution was added to this, followed by keeping at 65° C. for 1 hour, and then the mixture was immediately subjected to phenol/chloroform extraction. First, 42 ml of a phenol solution saturated with TE (10 mM Tris-HCl aqueous solution containing 1 mM EDTA.2Na; pH 8.0) was added to the reaction mixture, which was gently stirred. This was subjected to centrifugation (3,000 rpm, 10 minutes) to separate it into an aqueous phase and an organic phase, and only the aqueous phase was collected. To this aqueous phase, 21 ml of the aforementioned TE-saturated phenol solution and 21 ml of chloroform were added, and the mixture was gently stirred again. Then, this was subjected to centrifugation (3,000 rpm, 10 minutes) again to separate an aqueous phase and an organic phase, and only the aqueous phase was further collected. To this aqueous phase, 42 ml of chloroform was added, and the mixture was gently stirred. Then, this was subjected to centrifugation (3,000 rpm, 10 minutes) again to separate an aqueous phase and an organic phase, and only the aqueous phase was collected. To this aqueous phase, 4 ml of a TE solution containing 1.1 M NaCl and 92 ml of ethanol were added, and the mixture was left as such at room temperature for a while. Then, thus precipitated yarn-like DNA was collected by winding it around a glass rod. This was dehydrated through treatment with aqueous solutions of 70%, 80% and 90% ethanol in that order and then dried in the air. Then, thus collected DNA was redissolved in 40 ml of a TE solution. To this, 30 µg of RNase A was added, followed by keeping at 37° C. for 1 hour. Then, this was partially cleaved by means of a restriction endonuclease BamHI. The DNA thus partially cleaved was again purified by phenol extraction/chloroform extraction and ethanol precipitation, and it was dissolved in a TE solution to a final concentration of 1.0 µg/ml.

Example 82

Preparation of Nitrile Hydratase Gene from the Genomic DNA of *Rhodococcus rhodochrous* Strain J1 Using PCR Based on the base sequence of the nitrile hydratase gene as disclosed Patent Document 2 and Non-patent Document 1, the primers having the sequence as set forth in SEQ ID NOs: 105 and 106 in the Sequence Listing were synthesized. PCR was performed using 3 µg of the partially cleaved chromosome DNA as prepared in Example 81 as the template. In the PCR reaction, a system of 50 µl containing 200 ng of each primer and 1 U of KOD polymerase (manufactured by Toyobo Co., Ltd.) was subjected to 40 PCR cycles comprising thermal denaturation (98° C.) for 15 seconds, annealing (58° C.) for 15 seconds and chain extension (68° C.) for 2 minutes. After completion of the PCR reaction, the reaction mixture was subjected to agarose gel electrophoresis (using Type VII low-melting-point agarose, product by Sigma Corporation; agarose concentration 0.8% by weight) and an assay of the DNA amplification product was carried out, thereby it being possible to confirm the presence of an amplified DNA product of about 1.3 Kbp.

Subsequently, an agarose fragment comprising only a DNA fragment of about 1.3 kbp was cut out of the agarose gel. The thus-cut agarose fragment (about 0.1 g) was finely pulverized, suspended in 1 ml of a TE solution, and kept at 55° C. for 1 hour, whereby the agarose fragment was completely melted. The resulting agarose melt was subjected to phenol/chloroform extraction and ethanol precipitation. First, to this, 1 ml of a phenol solution saturated with TE (an aqueous solution of 10 mM Tris-HCl containing 1 mM EDTA.2Na; pH 8.0) was added, and the mixture was gently stirred. This was subjected to centrifugation (3,000 rpm, 10 minutes) to separate an aqueous phase and an organic phase, and only the aqueous phase was collected. After repeating this operation three times, to the obtained aqueous phase, 0.4 ml of the TE-saturated phenol solution and 0.4 ml of chloroform were added, and the mixture was again gently stirred. Then, this was subjected to centrifugation (3,000 rpm, 10 minutes) again to separate an aqueous phase and an organic phase, and only the aqueous phase was further collected. To this aqueous phase, 0.8 ml of chloroform was added, and the mixture was gently stirred. This was subjected to centrifugation (3,000 rpm, 10 minutes) again to separate an aqueous phase and an organic phase, and only the aqueous phase was collected. To this aqueous phase, 80 µl of a TE solution containing 1.1 M NaCl and 1.7 ml of ethanol were added, and after being stood still at −80° C. for 30 minutes, the mixture was subjected to centrifugation (15,000 rpm, 20 minutes, 4° C.) to recover DNA fragments. These DNA fragments were dried in the air and finally dissolved in 10 µl of TE.

After the purified amplified DNA fragment of about 1.3 kbp was cleaved by means of restriction endonucleases EcoRI and ScaI, an assay of the DNA amplification product was carried out by agarose gel electrophoresis (using Type VII low-melting-point agarose, product by Sigma Corporation; agarose concentration 0.8% by weight), and it was possible to confirm the presence of a DNA of about 1.3 Kbp. An agarose fragment comprising only the DNA fragment of about 1.3 kbp was cut out of the agarose gel. The thus-cut agarose fragment (about 0.1 g) was finely pulverized, suspended in 1 ml of a TE solution, and kept at 55° C. for 1 hour, whereby the agarose fragment was completely melted. The resulting agarose melt was subjected to phenol/chloroform extraction and ethanol precipitation. First, to this, 1 ml of a phenol solution saturated with TE (an aqueous solution of 10 mM Tris-HCl containing 1 mM EDTA.2Na; pH 8.0) was added, and the mixture was gently stirred. This was subjected to centrifugation (3,000 rpm, 10 minutes) to separate an aqueous phase and an organic phase, and only the aqueous phase was collected. After repeating this operation three times, to the obtained aqueous phase, 0.4 ml of the TE-saturated phenol solution and 0.4 ml of chloroform were added, and the mixture was again gently stirred. Then, this was subjected to centrifugation (3,000 rpm, 10 minutes) again to separate an aqueous phase and an organic phase, and only the aqueous phase was collected. To this aqueous phase, 0.8 ml of chloroform was added, and the mixture was gently stirred. This was subjected to centrifugation (3,000 rpm, 10 minutes) again to separate an aqueous phase and an organic phase, and only the aqueous phase was collected. To this aqueous phase, 80 µl of a TE solution containing 1.1 M NaCl and 1.7 ml of ethanol were added, and after being stood still at −80° C. for 30 minutes, the mixture was subjected to centrifugation (15,000 rpm, 20 minutes, 4° C.) to recover the DNA fragment. This DNA fragment was dried in the air and finally dissolved in 10 µl of TE.

Example 83

Preparation of Plasmid Vector to Express the *Rhodococcus rhodochrous* Strain J1-Derived Nitrile Hydratase Gene In a 500 ml Erlenmeyer flask with baffles, 100 ml of a liquid LB medium of the following composition containing 40 µg/ml of ferric sulfate.heptahydrate and 10 µg/ml of cobalt chloride.hexahydrate was prepared and sterilized by autoclaving at 121° C. for 20 minutes.

Medium composition;

Yeast extract: 5.0 g/L, polypeptone: 10.0 g/L, NaCl: 5.0 g/L, cobalt chloride.hexahydrate: 10.0 mg/L, ferric sulfate.theptahydrate: 40.0 mg/L, pH 7.5

To this medium, ampicillin was added to a final concentration of 100 µg/ml. Subsequently, one platinum loop of the cells of MT10822 (FERM BP-5785) as described in Patent Document 3 was inoculated and incubated therein at 37° C. for 16 hours with stirring at 130 rpm. The cells were separated from the resulting culture by centrifugation (15,000 G×15 minutes). Subsequently, the cells were resuspended in 50 ml of physiological saline, and then subjected to another centrifugation, thereby wet cells being obtained. The plasmid DNA pPT-DB1 (FIG. 1) was prepared from these wet cells by alkaline SDS extraction, and the product was subjected to addition of 30 µg of RNase A and incubation at 37° C. for 1 hour. Subsequently, the mixture was subjected to phenol extraction/chloroform extraction and ethanol precipitation to purify the DNA, and the DNA was dissolved in a TE solution to a final concentration of 1.0 µg/µl.

After 1 µg of the purified plasmid was cleaved by means of restriction endonucleases EcoRI and Eco47III, an assay of the DNA amplification product was carried out by agarose gel electrophoresis (using Type VII low-melting-point agarose, product by Sigma Corporation; agarose concentration 0.8% by weight), and it was possible to confirm the presence of DNAs of about 3.3 kbp and of about 1.3 kbp. An agarose fragment comprising only the DNA fragment of about 3.3 kbp was cut out of the agarose gel. The thus-cut agarose fragment (about 0.1 g) was finely pulverized, suspended in 1 ml of a TE solution, and kept at 55° C. for 1 hour, whereby the agarose fragment was completely melted. The resulting agarose melt was subjected to phenol/chloroform extraction and ethanol precipitation. First, to this, 1 ml of a phenol solution saturated with TE (an aqueous solution of 10 mM Tris-HCl containing 1 mM EDTA.2Na; pH 8.0) was added, and the mixture was gently stirred. This was subjected to centrifugation (3,000 rpm, 10 minutes) to separate an aqueous phase and an organic phase, and only the aqueous phase was collected. After repeating this operation three times, to the obtained aqueous phase, 0.4 ml of the TE-saturated phenol solution and 0.4 ml of chloroform were added, and the mixture was again gently stirred. Then, this was subjected to centrifugation (3,000 rpm, 10 minutes) again to separate an aqueous phase and an organic phase, and only the aqueous phase was further collected. To this aqueous phase, 0.8 ml of chloroform was added, and the mixture was gently stirred. This was subjected to centrifugation (3,000 rpm, 10 minutes) again to separate an aqueous phase and an organic phase, and only the aqueous phase was collected. To this aqueous phase, 80 µl of a TE solution containing 1.1 M NaCl and 1.7 ml of ethanol were added, and after being stood still at −80° C. for 30 minutes, the mixture was subjected to centrifugation (15,000 rpm, 20 minutes, 4° C.) to recover the DNA fragment. This DNA fragment was dried in the air and finally dissolved in 10 µl of TE.

Example 84

Construction of Transformant to Activate and Express the *Rhodocuccus rhodochrous* Strain J1-Derived Nitrile Hydratase A mixture of the DNA fragment of about 1.3 kbp which was prepared in Example 82 by cleavage by means of EcoRI and ScaI, and the DNA fragment of about 3.3 kbp which was prepared in Example 83 by cleavage by means of EcoRI and Eco47III was subjected to DNA ligation. A competent cell of *E. coli* HB101 (manufactured by Toyobo Co., Ltd.) was transformed with the reaction product to obtain transformant No. 200.

In a 500 ml Erlenmeyer flask with baffles, 100 ml of a liquid LB medium containing 40 µg/ml of ferric sulfate.heptahydrate and 10 µg/ml of cobalt chloride.hexahydrate was prepared and sterilized by autoclaving at 121° C. for 20 minutes. To this medium, ampicillin was added to a final concentration of 100 µg/ml. Subsequently, one platinum loop of the transformant No. 200 was inoculated and incubated therein at 37° C. for 20 hours with stirring at 130 rpm. The transformants were separated from the resulting culture by centrifugation (5,000 G×15 minutes). The transformants were resuspended in 50 ml of physiological saline and then subjected to another centrifugation (5,000 G×15 minutes), thereby the transformants being isolated.

0.1 g of thus isolated transformants were suspended in 20 ml of an aqueous solution (pH 7.0) of 50 mM potassium phosphate. To this, 0.5 ml of acrylonitrile or methacrylonitrile was added, and this mixture was gently stirred at 30° C. for 1 hour to react. After completion of the reaction, an analysis of the reaction solution was carried out with HPLC, and it was found that the reaction solution contained only an amide compound (acrylamide or methacrylamide) of a molar amount corresponding to the amount of the added nitrile compound (acrylonitrile or methacrylonitrile), and that the nitrile compound (acrylonitrile or methacrylonitrile) and the corresponding organic acid (acrylic acid or methacrylic acid) were absent. Thereafter, the conversion and the selectivity were 100%, respectively.

Further, a plasmid was prepared from this isolated transformant by alkaline SDS extraction, and the product was subjected to addition of 30 μg of RNase A and incubation at 37° C. for 1 hour. Subsequently, the mixture was subjected to phenol extraction/chloroform extraction and ethanol precipitation to purify the DNA, and the DNA was dissolved in a TE solution to a final concentration of 1.0 μg/μl. The base sequence of the nitrile hydratase gene was determined by the dideoxy chain termination method using a sequencing kit and an Autosequencer 373A manufactured by ABI. As a result, it was confirmed that the plasmid contained in its sequence the ORF which codes for the nitrile hydratase activating protein as set forth in SEQ ID NO: 103 in the Sequence Listing and the ORF which codes for the Rhodococcus rhodochrous strain J1-derived nitrile hydratase as set forth in SEQ ID NO: 104 in the Sequence Listing. This plasmid was named as pJ1H-DB1 (FIG. 2).

Example 85

Extraction of the Target of Mutation from Nitrile Hydratase Before Modification (1)

As the subject of the method for modification, Rhodococcus rhodochrous strain J1-derived nitrile hydratase was used as an example. Extraction of the target was carried out employing the method of specifying the amino acid residues which serve as the target of mutation as described in Claims 56 to 62 as an example. In the alignment of amino acid sequences for the method for specification as described in Claims 56 and 57, DNASIS manufactured by Hitach Software Engineering co., Ltd. was used. In the modeling of stereostructure based on the alignment of amino acid sequences for the method for specification as described in Claims 58 to 62, Modeler or Homology produced by Accelrys, Inc. was used.

As a result, in all cases, the extracted amino acid residues contained the 48$^{th}$ Trp of the amino acid sequence of the β-subunit, which is one of the two polypeptides constituting the nitrile hydratase. Thus, it was decided to use the 48$^{th}$ Trp of the amino acid sequence of the β-subunit of the Rhodococcus rhodochrous stain J1-derived nitrile hydratase as the example for the target of mutation.

Example 86

Extraction of the Target of Mutation from Nitrile Hydratase Before Modification (2)

As the subject of the method for modification, Pseudonocardia thermophila JCM3095-derived nitrile hydratase was used as an example. Extraction of the target was carried out employing the method of specifying the amino acid residues which serve as the target of mutation as described in Claims 56 to 62 as an example. In the alignment of amino acid sequences for the method for specification as described in Claims 56 and 57, DNASIS manufactured by Hitach Software Engineering co., Ltd. was used. In the modeling of stereostructure based on the alignment of amino acid sequences for the method for specification as described in Claims 58 to 62, Modeler or Homology produced by Accelrys, Inc. was used.

As a result, it was decided to use, among the amino acid residues extracted as the amino acid residues that are present in the region involved with forming a channel through which a substrate passes from the outside of the enzyme toward the active center or a product passes from the active center toward the outside of the enzyme, the 36$^{th}$ Thr and 48$^{th}$ Asn of the amino acid sequence of the α-subunit which is one of the two polypeptides constituting the nitrile hydratase, and the 32$^{nd}$ Val, 33$^{rd}$ Ala, 37$^{th}$ Phe, 40$^{th}$ Thr, 41$^{st}$ Phe, 46$^{th}$ Met, 48$^{th}$ Leu, 51$^{st}$ Phe, 61$^{st}$ Ala, 72$^{nd}$ Trp, 112$^{th}$ Lys, 118$^{th}$ Phe and 127$^{th}$ Leu of the amino acid sequence of the β-subunit which is another polypeptide, as the representative examples for the target of mutation, respectively.

Example 87

Extraction of the Target of Mutation from Nitrile Hydratase Before Modification (3)

As the subject of the method for modification, Pseudonocardia thermophila JCM3095-derived nitrile hydratase was used as an example. Extraction of the target was carried out employing the method of specifying the amino acid residues which serve as the target of mutation as described in Claims 56 to 62 as an example. In the alignment of amino acid sequences for the method for specification as described in Claims 56 and 57, DNASIS manufactured by Hitach Software Engineering co., Ltd. was used. In the modeling of stereostructure based on the alignment of amino acid sequences for the method for specification as described in Claims 58 to 62, Modeler or Homology produced by Accelrys, Inc. was used.

As a result, it was decided to use, among the amino acid residues extracted as the amino acid residues that are present in the region forming an associative interface between the α-subunit and the β-subunit which is involved with the formation of dimers or in the region forming an interface which is involved with the association of dimers, the 36$^{th}$ Thr, 148$^{th}$ Gly, 188$^{th}$ Thr and 204$^{th}$ Val of the amino acid sequence of the α-subunit which is one of the two polypeptides constituting the nitrile hydratase, and the 10$^{th}$ Thr, 32$^{nd}$ Val, 33$^{rd}$ Ala, 112$^{th}$ Lys, 118$^{th}$ Phe, 127$^{th}$ Leu, 146$^{th}$ Arg, 150$^{th}$ Ala, 160$^{th}$ Arg, 168$^{th}$ Thr, 171$^{st}$ Lys, 176$^{th}$ Tyr, 186$^{th}$ Leu, 217$^{th}$ Asp and 218$^{th}$ Cys of the amino acid sequence of the β-subunit which is another polypeptide, as the representative examples for the target of mutation, respectively.

Example 88

Introduction of Mutation for Construction of Modified Enzyme (1)

In order to introduce mutation to the amino acid sequence of the polypeptides constituting nitrile hydratase, introduction of site-specific mutation was performed using a "LA PCR in vitro mutagenesis Kit" (manufactured by Takara Shuzo Co., Ltd.). The "LA PCR in vitro mutagenesis Kit" is simply referred to as the kit. In the following examples, the kit was handled on the basis of the principle thereof and in accordance with the manufacturer's instructions for the kit.

Onto a plasmid: pJ1H-DB1 containing the ORF that codes for the *Rhodococcus rhodochrous* strain J1-derived nitrile hydratase as constructed in Example 84, mutation was performed to change the 48$^{th}$ Trp of the amino acid sequence of the β-subunit, which is the target of mutation as extracted in Example 85, to another amino acid.

Using 10 ng of pJ1H-DB1 as the template, PCRs of two different types were carried out. For the PCR reaction No. 1, a reaction system of 50 µl in total comprising 50 pmol of the primer having the sequence as forth in SEQ ID NO: 110 in the Sequence Listing and 50 pmol of an M13 primer M4 (having the sequence as set forth in SEQ ID NO: 107 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes. For the PCR reaction No. 2, a reaction system of 50 µl in total comprising 50 pmol of an MUT4 primer (having the sequence as set forth in SEQ ID NO: 108 in the Sequence Listing) and 50 pmol of an M13 primer RV (having the sequence as set forth in SEQ ID NO: 109 in the Sequence Listing) (for the composition of the system, the manufacturer's instructions for the kit were followed) was used, and the reaction was carried out following the same procedure as the PCR reaction No. 1.

After completion of the PCR reaction Nos. 1 and 2, 5 µl of the reaction mixture was subjected to agarose gel electrophoresis (where the agarose concentration was 1.0% by weight), and an assay of the DNA amplification product was carried out. This assay revealed the production of the amplified DNA products in the both PCR reactions. From each of these PCR reaction mixtures, the excess primers and dNTP were removed using Microcon 100 (manufactured by Takara Shuzo Co., Ltd.), and then TE was added to each of the mixtures to prepare 50 µl each of TE solutions. An annealing solution of 47.5 µl in total containing 0.5 µl of both of the above TE solutions (for the composition of the system, the manufacturer's instructions for the kit were followed) was prepared, and this solution was subjected to annealing by performing thermal denaturation of the solution at 98° C. for 10 minutes, subsequently cooling the solution to 37° C. at a constant cooling rate over a period of 60 minutes, and then maintaining it at 37° C. for 15 minutes.

To thus annealed solution, 0.5 µl of TAKARA LA Taq was added, and the solution was heated at 72° C. for 3 minutes, thus completing the formation of heterologous double-stranded DNA. This was then subjected to PCR reaction No. 3. For PCR reaction No. 3, a reaction system of 50 µl in total comprising 50 pmol of an M13 primer M4 (having the sequence as set forth in SEQ ID NO: 107 in the Sequence Listing) and 50 pmol of an M13 primer RV (having the sequence as set forth in SEQ ID NO: 109 in the Sequence Listing) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes.

After completion of the PCR reaction No. 3, 5 µl of the reaction mixture was subjected to agarose gel electrophoresis (using Type VII low-melting-point agarose, product by Sigma Corporation; agarose concentration 0.8% by weight), and an assay of the DNA amplification product was carried out, thereby it being possible to confirm the presence of an amplified DNA product of about 1.9 Kbp. An agarose fragment comprising only the DNA fragment of about 1.9 kbp was cut out of the agarose gel. The thus-cut agarose fragment (about 0.1 g) was finely pulverized, suspended in 1 ml of a TE solution, and kept at 55° C. for 1 hour, whereby the agarose fragment was completely melted. The resulting agarose melt was subjected to phenol/chloroform extraction and ethanol precipitation to purify the DNA fragment. Thus purified DNA fragment was finally dissolved in 10 µl of TE.

After the purified amplified DNA fragment of about 1.9 kbp was cleaved by means of restriction endonucleases EcoRI and HindIII, this mixture treated with restriction endonucleases was subjected to phenol/chloroform extraction and ethanol precipitation to purify the DNA fragment. Thus purified DNA fragment was finally dissolved in 10 µl of TE. Likewise, pJ1H-DB1 was cleaved by means of EcoRI and HindIII, and the mixture was subjected to agarose gel electrophoresis (using Type VII low-melting-point agarose, product by Sigma Corporation; agarose concentration of 0.7%). An agarose fragment comprising only the DNA fragment of about 2.7 kbp was cut out of the agarose gel. The thus-cut agarose fragment (about 0.1 g) was finely pulverized, suspended in 1 ml of a TE solution, and kept at 55° C. for 1 hour, whereby the agarose fragment was completely melted. The resulting agarose melt was subjected to phenol/chloroform extraction and ethanol precipitation to purify the DNA fragment. Thus purified DNA fragment was finally dissolved in 10 µl of TE.

Thus obtained DNA fragments of about 1.9 kbp and of about 2.7 kbp were subjected to DNA ligation. A competent cell of *E. coli* HB101 (manufactured by Toyobo Co., Ltd.) was transformed with the reaction product to obtain a number of transformants. Plasmids were prepared from the respective transformants, and the plasmids were subjected to addition of 30 µg of RNase A and incubation at 37° C. for 1 hour. Subsequently, the mixtures were subjected to phenol extraction/chloroform extraction and ethanol precipitation to purify the DNAs, and they were each dissolved in a TE solution to a final concentration of 1.0 µg/µl. The base sequences thereof were determined by the dideoxy chain termination method using a sequencing kit and an Autosequencer 373A manufactured by ABI.

As a result, it was found that the plasmids from the above-obtained transformants were such that the base sequence corresponding to the codon encoding the 48$^{th}$ amino acid in the amino acid sequence of the β-subunit of *Rhodococcus rhodochrous* strain J1-derived nitrile hydratase had been changed to a base sequence corresponding to the codon encoding an amino acid other than Trp, as compared with pJ1H-DB1.

In Table 121 below, the numbers of the obtained transformants as well as the corresponding mutated sites, changes in amino acid sequence and changes in base sequence are given.

TABLE 121

| Number | Mutated site | Change in amino acid sequence | | Change in base sequence | |
|---|---|---|---|---|---|
| | | Before mutation | After mutation | Before mutation | After mutation |
| No. 201 | 48$^{th}$ position in β-subunit | Trp | Tyr | tgg | tat |
| No. 202 | 48$^{th}$ position in β-subunit | Trp | Val | tgg | gtg |
| No. 203 | 48$^{th}$ position in β-subunit | Trp | Ala | tgg | gcg |

TABLE 121-continued

| Number | Mutated site | Change in amino acid sequence | | Change in base sequence | |
|---|---|---|---|---|---|
| | | Before mutation | After mutation | Before mutation | After mutation |
| No. 204 | 48th position in β-subunit | Trp | Gly | tgg | ggg |

Example 89

Introduction of Mutation for Construction of Modified Enzyme (2)

Onto a plasmid: pPT-DB1 containing the ORF that codes for the *Pseudonocardia thermophila* JCM3095-derived nitrile hydratase as constructed from MT10822 in Example 83, mutation was performed to change the 36th Thr of the amino acid sequence of the α-subunit, which is the target of mutation as extracted in Example 86 or 87, to another amino acid.

Using 10 ng of pPT-DB1 as the template, PCRs of two different types were carried out. For the PCR reaction No. 1, a reaction system of 50 µl in total comprising 50 pmol of the primer having the sequence as forth in SEQ ID NO: 111 in the Sequence Listing and 50 pmol of an M13 primer M4 (having the sequence as set forth in SEQ ID NO: 107 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes. For the PCR reaction No. 2, a reaction system of 50 µl in total comprising 50 pmol of an MUT4 primer (having the sequence as set forth in SEQ ID NO: 108 in the Sequence Listing) and 50 pmol of an M13 primer RV (having the sequence as set forth in SEQ ID NO: 109 in the Sequence Listing) (for the composition of the system, the manufacturer's instructions for the kit were followed) was used, and the reaction was carried out following the same procedure as the PCR reaction No. 1.

After completion of the PCR reaction Nos. 1 and 2, 5 µl of the reaction mixture was subjected to agarose gel electrophoresis (where the agarose concentration was 1.0% by weight), and an assay of the DNA amplification product was carried out. This assay revealed the production of the amplified DNA products in the both PCR reactions. From each of these PCR reaction mixtures, the excess primers and dNTP were removed using Microcon 100 (manufactured by Takara Shuzo Co., Ltd.), and then TE was added to each of the mixtures to prepare 50 µl each of TE solutions. An annealing solution of 47.5 µl in total containing 0.5 µl of both of the above TE solutions (for the composition of the system, the manufacturer's instructions for the kit were followed) was prepared, and this solution was subjected to annealing by performing thermal denaturation of the solution at 98° C. for 10 minutes, subsequently cooling the solution to 37° C. at a constant cooling rate over a period of 60 minutes, and then maintaining it at 37° C. for 15 minutes.

To thus annealed solution, 0.5 µl of TAKARA LA Taq was added, and the solution was heated at 72° C. for 3 minutes, thus completing the formation of heterologous double-stranded DNA. This was then subjected to PCR reaction No. 3. For PCR reaction No. 3, a reaction system of 50 µl in total comprising 50 pmol of an M13 primer M4 (having the sequence as set forth in SEQ ID NO: 107 in the Sequence Listing) and 50 pmol of an M13 primer RV (having the sequence as set forth in SEQ ID NO: 109 in the Sequence Listing) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes.

After completion of the PCR reaction No. 3, 5 µl of the reaction mixture was subjected to agarose gel electrophoresis (using Type VII low-melting-point agarose, product by Sigma Corporation; agarose concentration 0.8% by weight), and an assay of the DNA amplification product was carried out, thereby it being possible to confirm the presence of an amplified DNA product of about 1.9 Kbp. An agarose fragment comprising only the DNA fragment of about 1.9 kbp was cut out of the agarose gel. The thus-cut agarose fragment (about 0.1 g) was finely pulverized, suspended in 1 ml of a TE solution, and kept at 55° C. for 1 hour, whereby the agarose fragment was completely melted. The resulting agarose melt was subjected to phenol/chloroform extraction and ethanol precipitation to purify the DNA fragment. Thus purified DNA fragment was finally dissolved in 10 µl of TE.

After the purified amplified DNA fragment of about 1.9 kbp was cleaved by means of restriction endonucleases EcoRI and HindIII, this mixture treated with restriction endonucleases was subjected to phenol/chloroform extraction and ethanol precipitation to purify the DNA fragment. Thus purified DNA fragment was finally dissolved in 10 µl of TE. Likewise, pPT-DB1 was cleaved by means of EcoRI and HindIII, and then subjected to agarose gel electrophoresis (using Type VII low-melting-point agarose, product by Sigma Corporation; agarose concentration of 0.7%). An agarose fragment comprising only the DNA fragment of about 2.7 kbp was cut out of the agarose gel. The thus-cut agarose fragment (about 0.1 g) was finely pulverized, suspended in 1 ml of a TE solution, and kept at 55° C. for 1 hour, whereby the agarose fragment was completely melted. The resulting agarose melt was subjected to phenol/chloroform extraction and ethanol precipitation to purify the DNA fragment. Thus purified DNA fragment was finally dissolved in 10 µl of TE.

Thus obtained DNA fragments of about 1.9 kbp and of about 2.7 kbp were subjected to DNA ligation. A competent cell of *E. coli* HB101 (manufactured by Toyobo Co., Ltd.) was transformed with the reaction product to obtain a number of transformants. Plasmids were prepared from the respective transformants, and the plasmids were subjected to addition of 30 µg of RNase A and incubation at 37° C. for 1 hour. Subsequently, the mixtures were subjected to phenol extraction/chloroform extraction and ethanol precipitation to purify the DNAs, and they were each dissolved in a TE solution to a final concentration of 1.0 µg/µl. The base sequences thereof were determined by the dideoxy chain termination method using a sequencing kit and an Autosequencer 373A manufactured by ABI.

As a result, it was found that the plasmids from the above-obtained transformants were such that the base sequence corresponding to the codon encoding the 36th amino acid in the amino acid sequence of the α-subunit of *Pseudonocardia thermophila* JCM3095-derived nitrile hydratase had been changed to a base sequence corresponding to the codon encoding an amino acid other than Thr, as compared with pPT-DB1.

In Table 122 below, the numbers of the obtained transformants as well as the corresponding mutated sites, changes in amino acid sequence and changes in base sequence are given.

TABLE 122

| Number | Mutated site | Change in amino acid sequence | | Change in base sequence | |
|---|---|---|---|---|---|
| | | Before mutation | After mutation | Before mutation | After mutation |
| No. 40 | 36th position in α-subunit | Thr | Met | acg | atg |
| No. 40a | 36th position in α-subunit | Thr | Ser | acg | tcg |
| No. 40b | 36th position in α-subunit | Thr | Ala | acg | gcg |
| No. 40c | 36th position in α-subunit | Thr | Gly | acg | ggg |
| No. 40d | 36th position in α-subunit | Thr | Trp | acg | tgg |

Example 90

Introduction of Mutation for Construction of Modified Enzyme (3)

Onto a plasmid: pPT-DB1 containing the ORF that codes for the *Pseudonocardia thermophila* JCM3095-derived nitrile hydratase as constructed from MT10822 in Example 83, mutation was performed to change the 48$^{th}$ Asn of the amino acid sequence of the α-subunit, which is the target of mutation as extracted in Example 86 or 87, to another amino acid.

Using 10 ng of pPT-DB1 as the template, PCRs of two different types were carried out. For the PCR reaction No. 1, a reaction system of 50 µl in total comprising 50 pmol of the primer having the sequence as forth in SEQ ID NO: 112 in the Sequence Listing and 50 pmol of an M13 primer M4 (having the sequence as set forth in SEQ ID NO: 107 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes. For the PCR reaction No. 2, a reaction system of 50 µl in total comprising 50 pmol of an MUT4 primer (having the sequence as set forth in SEQ ID NO: 108 in the Sequence Listing) and 50 pmol of an M13 primer RV (having the sequence as set forth in SEQ ID NO: 109 in the Sequence Listing) (for the composition of the system, the manufacturer's instructions for the kit were followed) was used, and the reaction was carried out following the same procedure as the PCR reaction No. 1.

Thereafter, the same procedure as in Example 89 was carried out to obtain a number of transformants. Plasmids were prepared from the respective transformants, and the plasmids were subjected to addition of 30 µg of RNase A and incubation at 37° C. for 1 hour. Subsequently, the mixtures were subjected to phenol extraction/chloroform extraction and ethanol precipitation to purify the DNAs, and they were each dissolved in a TE solution to a final concentration of 1.0 µg/µl. The base sequences thereof were determined by the dideoxy chain termination method using a sequencing kit and an Autosequencer 373A manufactured by ABI.

As a result, it was found that the plasmids from the above-obtained transformants were such that the base sequence corresponding to the codon encoding the 48$^{th}$ amino acid in the amino acid sequence of the α-subunit of *Pseudonocardia thermophila* JCM3095-derived nitrile hydratase had been changed to a base sequence corresponding to the codon encoding an amino acid other than Asn, as compared with pPT-DB1.

In Table 123 below, the numbers of the obtained transformants as well as the corresponding mutated sites, changes in amino acid sequence and changes in base sequence are given.

TABLE 123

| Number | Mutated site | Change in amino acid sequence | | Change in base sequence | |
|---|---|---|---|---|---|
| | | Before mutation | After mutation | Before mutation | After mutation |
| No. 40e | 48th position in α-subunit | Asn | Gln | aac | caa |
| No. 40f | 48th position in α-subunit | Asn | Glu | aac | gaa |

Example 91

Introduction of Mutation for Construction of Modified Enzyme (4)

Onto a plasmid: pPT-DB1 containing the ORF that codes for the *Pseudonocardia thermophila* JCM3095-derived nitrile hydratase as constructed from MT10822 in Example 83, mutation was performed to change the 71$^{st}$ Arg of the amino acid sequence of the α-subunit, which is the target of mutation as extracted in Example 86 or 87, to another amino acid.

Using 10 ng of pPT-DB1 as the template, PCRs of two different types were carried out. For the PCR reaction No. 1, a reaction system of 50 µl in total comprising 50 pmol of the primer having the sequence as forth in SEQ ID NO: 113 in the Sequence Listing and 50 pmol of an M13 primer M4 (having the sequence as set forth in SEQ ID NO: 107 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes. For the PCR reaction No. 2, a reaction system of 50 µl in total comprising 50 pmol of an MUT4 primer (having the sequence as set forth in SEQ ID NO: 108 in the Sequence Listing) and 50 pmol of an M13 primer RV (having the sequence as set forth in SEQ ID NO: 109 in the Sequence Listing) (for the composition of the system, the manufacturer's instructions for the kit were followed) was used, and the reaction was carried out following the same procedure as the PCR reaction No. 1.

Thereafter, the same procedure as in Example 89 was carried out to obtain a number of transformants. Plasmids were prepared from the respective transformants, and the plasmids were subjected to addition of 30 µg of RNase A and incubation at 37° C. for 1 hour. Subsequently, the mixtures were subjected to phenol extraction/chloroform extraction and ethanol precipitation to purify the DNAs, and they were each dissolved in a TE solution to a final concentration of 1.0 µg/µl. The base sequences thereof were determined by the dideoxy chain termination method using a sequencing kit and an Autosequencer 373A manufactured by ABI.

As a result, it was found that the plasmids from the above-obtained transformants were such that the base sequence corresponding to the codon encoding the 71$^{st}$ amino acid in the amino acid sequence of the α-subunit of *Pseudonocardia thermophila* JCM3095-derived nitrile hydratase had been changed to a base sequence corresponding to the codon encoding an amino acid other than Arg, as compared with pPT-DB1.

In Table 124 below, the numbers of the obtained transformants as well as the corresponding mutated sites, changes in amino acid sequence and changes in base sequence are given.

TABLE 124

| Number | Mutated site | Change in amino acid sequence | | Change in base sequence | |
|---|---|---|---|---|---|
| | | Before mutation | After mutation | Before mutation | After mutation |
| No. 41 | 71$^{st}$ position in α-subunit | Arg | His | cgt | cat |

Example 92

Introduction of Mutation for Construction of Modified Enzyme (5)

Onto a plasmid: pPT-DB1 containing the ORF that codes for the *Pseudonocardia thermophila* JCM3095-derived nitrile hydratase as constructed from MT10822 in Example 83, mutation was performed to change the 148$^{th}$ Gly of the amino acid sequence of the α-subunit, which is the target of mutation as extracted in Example 86 or 87, to another amino acid.

Using 10 ng of pPT-DB1 as the template, PCRs of two different types were carried out. For the PCR reaction No. 1, a reaction system of 50 μl in total comprising 50 pmol of the primer having the sequence as forth in SEQ ID NO: 114 in the Sequence Listing and 50 pmol of an M13 primer M4 (having the sequence as set forth in SEQ ID NO: 107 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes. For the PCR reaction No. 2, a reaction system of 50 μl in total comprising 50 pmol of an MUT4 primer (having the sequence as set forth in SEQ ID NO: 108 in the Sequence Listing) and 50 pmol of an M13 primer RV (having the sequence as set forth in SEQ ID NO: 109 in the Sequence Listing) (for the composition of the system, the manufacturer's instructions for the kit were followed) was used, and the reaction was carried out following the same procedure as the PCR reaction No. 1.

Thereafter, the same procedure as in Example 89 was carried out to obtain a number of transformants. Plasmids were prepared from the respective transformants, and the plasmids were subjected to addition of 30 μg of RNase A and incubation at 37° C. for 1 hour. Subsequently, the mixtures were subjected to phenol extraction/chloroform extraction and ethanol precipitation to purify the DNAs, and they were each dissolved in a TE solution to a final concentration of 1.0 μg/μl. The base sequences thereof were determined by the dideoxy chain termination method using a sequencing kit and an Autosequencer 373A manufactured by ABI.

As a result, it was found that the plasmids from the above-obtained transformants were such that the base sequence corresponding to the codon encoding the 148$^{th}$ amino acid in the amino acid sequence of the α-subunit of *Pseudonocardia thermophila* JCM3095-derived nitrile hydratase had been changed to a base sequence corresponding to the codon encoding an amino acid other than Gly, as compared with pPT-DB1.

In Table 125 below, the numbers of the obtained transformants as well as the corresponding mutated sites, changes in amino acid sequence and changes in base sequence are given.

TABLE 125

| Number | Mutated site | Change in amino acid sequence | | Change in base sequence | |
|---|---|---|---|---|---|
| | | Before mutation | After mutation | Before mutation | After mutation |
| No. 42 | 148$^{th}$ position in α-subunit | Gly | Asp | ggc | gac |

Example 93

Introduction of Mutation for Construction of Modified Enzyme (6)

Onto a plasmid: pPT-DB1 containing the ORF that codes for the *Pseudonocardia thermophila* JCM3095-derived nitrile hydratase as constructed from MT10822 in Example 83, mutation was performed to change the 188$^{th}$ Thr of the amino acid sequence of the α-subunit, which is the target of mutation as extracted in Example 86 or 87, to another amino acid.

Using 10 ng of pPT-DB1 as the template, PCRs of two different types were carried out. For the PCR reaction No. 1, a reaction system of 50 μl in total comprising 50 pmol of the primer having the sequence as forth in SEQ ID NO: 115 in the Sequence Listing and 50 pmol of an M13 primer M4 (having the sequence as set forth in SEQ ID NO: 107 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes. For the PCR reaction No. 2, a reaction system of 50 μl in total comprising 50 pmol of an MUT4 primer (having the sequence as set forth in SEQ ID NO: 108 in the Sequence Listing) and 50 pmol of an M13 primer RV (having the sequence as set forth in SEQ ID NO: 109 in the Sequence Listing) (for the composition of the system, the manufacturer's instructions for the kit were followed) was used, and the reaction was carried out following the same procedure as the PCR reaction No. 1.

Thereafter, the same procedure as in Example 89 was carried out to obtain a number of transformants. Plasmids were prepared from the respective transformants, and the plasmids were subjected to addition of 30 μg of RNase A and incubation at 37° C. for 1 hour. Subsequently, the mixtures were subjected to phenol extraction/chloroform extraction and ethanol precipitation to purify the DNAs, and they were each dissolved in a TE solution to a final concentration of 1.0 μg/μl. The base sequences thereof were determined by the dideoxy chain termination method using a sequencing kit and an Autosequencer 373A manufactured by ABI.

As a result, it was found that the plasmids from the above-obtained transformants were such that the base sequence corresponding to the codon encoding the 188$^{th}$ amino acid in the amino acid sequence of the α-subunit of *Pseudonocardia thermophila* JCM3095-derived nitrile hydratase had been changed to a base sequence corresponding to the codon encoding an amino acid other than Thr, as compared with pPT-DB1.

In Table 126 below, the numbers of the obtained transformants as well as the corresponding mutated sites, changes in amino acid sequence and changes in base sequence are given.

TABLE 126

| Number | Mutated site | Change in amino acid sequence | | Change in base sequence | |
|---|---|---|---|---|---|
| | | Before mutation | After mutation | Before mutation | After mutation |
| No. 42a | 188th position in α-subunit | Thr | Gly | acc | ggc |

Example 94

Introduction of Mutation for Construction of Modified Enzyme (7)

Onto a plasmid: pPT-DB1 containing the ORF that codes for the *Pseudonocardia thermophila* JCM3095-derived nitrile hydratase as constructed from MT10822 in Example 83, mutation was performed to change the 204th Val of the amino acid sequence of the α-subunit, which is the target of mutation as extracted in Example 86 or 87, to another amino acid.

Using 10 ng of pPT-DB1 as the template, PCRs of two different types were carried out. For the PCR reaction No. 1, a reaction system of 50 μin total comprising 50 pmol of the primer having the sequence as forth in SEQ ID NO: 116 in the Sequence Listing and 50 pmol of an M13 primer M4 (having the sequence as set forth in SEQ ID NO: 107 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes. For the PCR reaction No. 2, a reaction system of 50 μl in total comprising 50 pmol of an MUT4 primer (having the sequence as set forth in SEQ ID NO: 108 in the Sequence Listing) and 50 pmol of an M13 primer RV (having the sequence as set forth in SEQ ID NO: 109 in the Sequence Listing) (for the composition of the system, the manufacturer's instructions for the kit were followed) was used, and the reaction was carried out following the same procedure as the PCR reaction No. 1.

Thereafter, the same procedure as in Example 89 was carried out to obtain a number of transformants. Plasmids were prepared from the respective transformants, and the plasmids were subjected to addition of 30 μg of RNase A and incubation at 37° C. for 1 hour. Subsequently, the mixtures were subjected to phenol extraction/chloroform extraction and ethanol precipitation to purify the DNAs, and they were each dissolved in a TE solution to a final concentration of 1.0 μg/μl. The base sequences thereof were determined by the dideoxy chain termination method using a sequencing kit and an Autosequencer 373A manufactured by ABI.

As a result, it was found that the plasmids from the above-obtained transformants were such that the base sequence corresponding to the codon encoding the 204th amino acid in the amino acid sequence of the α-subunit of *Pseudonocardia thermophila* JCM3095-derived nitrile hydratase had been changed to a base sequence corresponding to the codon encoding an amino acid other than Val, as compared with pPT-DB1.

In Table 127 below, the numbers of the obtained transformants as well as the corresponding mutated sites, changes in amino acid sequence and changes in base sequence are given.

TABLE 127

| Number | Mutated site | Change in amino acid sequence | | Change in base sequence | |
|---|---|---|---|---|---|
| | | Before mutation | After mutation | Before mutation | After mutation |
| No. 43 | 204th position in α-subunit | Val | Arg | gtc | cgc |
| No. 44 | 204th position in α-subunit | Val | Lys | gtc | aaa |
| No. 45 | 204th position in α-subunit | Val | Trp | gtc | tgg |
| No. 46 | 204th position in α-subunit | Val | Thr | gtc | acc |

Example 95

Introduction of Mutation for Construction of Modified Enzyme (8)

Onto a plasmid: pPT-DB1 containing the ORF that codes for the *Pseudonocardia thermophila* JCM3095-derived nitrile hydratase as constructed from MT10822 in Example 83, mutation was performed to change the 10th Thr of the amino acid sequence of the β-subunit, which is the target of mutation as extracted in Example 86 or 87, to another amino acid.

Using 10 ng of pPT-DB1 as the template, PCRs of two different types were carried out. For the PCR reaction No. 1, a reaction system of 50 μl in total comprising 50 pmol of the primer having the sequence as forth in SEQ ID NO: 117 in the Sequence Listing and 50 pmol of an M13 primer M4 (having the sequence as set forth in SEQ ID NO: 107 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes. For the PCR reaction No. 2, a reaction system of 50 μl in total comprising 50 pmol of an MUT4 primer (having the sequence as set forth in SEQ ID NO: 108 in the Sequence Listing) and 50 pmol of an M13 primer RV (having the sequence as set forth in SEQ ID NO: 109 in the Sequence Listing) (for the composition of the system, the manufacturer's instructions for the kit were followed) was used, and the reaction was carried out following the same procedure as the PCR reaction No. 1.

Thereafter, the same procedure as in Example 89 was carried out to obtain a number of transformants. Plasmids were prepared from the respective transformants, and the plasmids were subjected to addition of 30 μg of RNase A and incubation at 37° C. for 1 hour. Subsequently, the mixtures were subjected to phenol extraction/chloroform extraction and ethanol precipitation to purify the DNAs, and they were each dissolved in a TE solution to a final concentration of 1.0 μg/μl. The base sequences thereof were determined by the dideoxy chain termination method using a sequencing kit and an Autosequencer 373A manufactured by ABI.

As a result, it was found that the plasmids from the above-obtained transformants were such that the base sequence corresponding to the codon encoding the 10$^{th}$ amino acid in the amino acid sequence of the β-subunit of *Pseudonocardia thermophila* JCM3095-derived nitrile hydratase had been changed to a base sequence corresponding to the codon encoding an amino acid other than Thr, as compared with pPT-DB1.

In Table 128 below, the numbers of the obtained transformants as well as the corresponding mutated sites, changes in amino acid sequence and changes in base sequence are given.

TABLE 128

| | | Change in amino acid sequence | | Change in base sequence | |
|---|---|---|---|---|---|
| Number | Mutated site | Before mutation | After mutation | Before mutation | After mutation |
| No. 47 | 10$^{th}$ position in β-subunit | Thr | Asp | acc | gac |
| No. 48 | 10$^{th}$ position in β-subunit | Thr | Glu | acc | gaa |
| No. 49 | 10$^{th}$ position in β-subunit | Thr | Trp | acc | tgg |
| No. 50 | 10$^{th}$ position in β-subunit | Thr | Gly | acc | ggc |
| No. 51 | 10$^{th}$ position in β-subunit | Thr | Tyr | acc | tac |
| No. 52 | 10$^{th}$ position in β-subunit | Thr | Cys | acc | tgc |

Example 96

Introduction of Mutation for Construction of Modified Enzyme (9)

Onto a plasmid: pPT-DB1 containing the ORF that codes for the *Pseudonocardia thermophila* JCM3095-derived nitrile hydratase as constructed from MT10822 in Example 83, mutation was performed to change the 32$^{nd}$ Val of the amino acid sequence of the β-subunit, which is the target of mutation as extracted in Example 86 or 87, to another amino acid.

Using 10 ng of pPT-DB1 as the template, PCRs of two different types were carried out. For the PCR reaction No. 1, a reaction system of 50 μl in total comprising 50 pmol of the primer having the sequence as forth in SEQ ID NO: 118 in the Sequence Listing and 50 pmol of an M13 primer M4 (having the sequence as set forth in SEQ ID NO: 107 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes. For the PCR reaction No. 2, a reaction system of 50 μl in total comprising 50 pmol of an MUT4 primer (having the sequence as set forth in SEQ ID NO: 108 in the Sequence Listing) and 50 pmol of an M13 primer RV (having the sequence as set forth in SEQ ID NO: 109 in the Sequence Listing) (for the composition of the system, the manufacturer's instructions for the kit were followed) was used, and the reaction was carried out following the same procedure as the PCR reaction No. 1.

Thereafter, the same procedure as in Example 89 was carried out to obtain a number of transformants. Plasmids were prepared from the respective transformants, and the plasmids were subjected to addition of 30 μg of RNase A and incubation at 37° C. for 1 hour. Subsequently, the mixtures were subjected to phenol extraction/chloroform extraction and ethanol precipitation to purify the DNAs, and they were each dissolved in a TE solution to a final concentration of 1.0 μg/μl. The base sequences thereof were determined by the dideoxy chain termination method using a sequencing kit and an Autosequencer 373A manufactured by ABI.

As a result, it was found that the plasmids from the above-obtained transformants were such that the base sequence corresponding to the codon encoding the 32$^{nd}$ amino acid in the amino acid sequence of the β-subunit of *Pseudonocardia thermophila* JCM3095-derived nitrile hydratase had been changed to a base sequence corresponding to the codon encoding an amino acid other than Val, as compared with pPT-DB1.

In Table 129 below, the numbers of the obtained transformants as well as the corresponding mutated sites, changes in amino acid sequence and changes in base sequence are given.

TABLE 129

| | | Change in amino acid sequence | | Change in base sequence | |
|---|---|---|---|---|---|
| Number | Mutated site | Before mutation | After mutation | Before mutation | After mutation |
| No. 53 | 32$^{nd}$ positon in β-subunit | Val | Gly | gtc | ggc |

Example 97

Introduction of Mutation for Construction of Modified Enzyme (10)

Onto a plasmid: pPT-DB1 containing the ORF that codes for the *Pseudonocardia thermophila* JCM3095-derived nitrile hydratase as constructed from MT10822 in Example 83, mutation was performed to change the 33$^{rd}$ Ala of the amino acid sequence of the β-subunit, which is the target of mutation as extracted in Example 86 or 87, to another amino acid.

Using 10 ng of pPT-DB1 as the template, PCRs of two different types were carried out. For the PCR reaction No. 1, a reaction system of 50 μl in total comprising 50 pmol of the primer having the sequence as forth in SEQ ID NO: 119 in the Sequence Listing and 50 pmol of an M13 primer M4 (having the sequence as set forth in SEQ ID NO: 107 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes. For the PCR reaction No. 2, a reaction system of 50 μl in total comprising 50 pmol of an MUT4 primer (having the sequence as set forth in SEQ ID NO: 108 in the Sequence Listing) and 50 pmol of an M13 primer RV (having the sequence as set forth in SEQ ID NO: 109 in the Sequence Listing) (for the composition of the system, the manufacturer's instructions for the kit were followed) was used, and the reaction was carried out following the same procedure as the PCR reaction No. 1.

Thereafter, the same procedure as in Example 89 was carried out to obtain a number of transformants. Plasmids were prepared from the respective transformants, and the plasmids were subjected to addition of 30 μg of RNase A and incubation at 37° C. for 1 hour. Subsequently, the mixtures were subjected to phenol extraction/chloroform extraction and ethanol precipitation to purify the DNAs, and they were each dissolved in a TE solution to a final concentration of 1.0 µg/µl. The base sequences thereof were determined by the dideoxy chain termination method using a sequencing kit and an Autosequencer 373A manufactured by ABI.

As a result, it was found that the plasmids from the above-obtained transformants were such that the base sequence corresponding to the codon encoding the 33$^{rd}$ amino acid in the amino acid sequence of the β-subunit of *Pseudonocardia thermophila* JCM3095-derived nitrile hydratase had been changed to a base sequence corresponding to the codon encoding an amino acid other than Ala, as compared with pPT-DB1.

In Table 130 below, the numbers of the obtained transformants as well as the corresponding mutated sites, changes in amino acid sequence and changes in base sequence are given.

TABLE 130

| Number | Mutated site | Change in amino acid sequence | | Change in base sequence | |
|---|---|---|---|---|---|
| | | Before mutation | After mutation | Before mutation | After mutation |
| No. 53a | 33$^{rd}$ position in β-subunit | Ala | Val | gcg | gtg |
| No. 53b | 33$^{rd}$ position in β-subunit | Ala | Met | gcg | atg |

Example 98

Introduction of Mutation for Construction of Modified Enzyme (11)

Onto a plasmid: pPT-DB1 containing the ORF that codes for the *Pseudonocardia thermophila* JCM3095-derived nitrile hydratase as constructed from MT10822 in Example 83, mutation was performed to change the 37$^{th}$ Phe of the amino acid sequence of the β-subunit, which is the target of mutation as extracted in Example 86 or 87, to another amino acid.

Using 10 ng of pPT-DB1 as the template, PCRs of two different types were carried out. For the PCR reaction No. 1, a reaction system of 50 µl in total comprising 50 pmol of the primer having the sequence as forth in SEQ ID NO: 120 in the Sequence Listing and 50 pmol of an M13 primer M4 (having the sequence as set forth in SEQ ID NO: 107 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes. For the PCR reaction No. 2, a reaction system of 50 µl in total comprising 50 pmol of an MUT4 primer (having the sequence as set forth in SEQ ID NO: 108 in the Sequence Listing) and 50 pmol of an M13 primer RV (having the sequence as set forth in SEQ ID NO: 109 in the Sequence Listing) (for the composition of the system, the manufacturer's instructions for the kit were followed) was used, and the reaction was carried out following the same procedure as the PCR reaction No. 1.

Thereafter, the same procedure as in Example 89 was carried out to obtain a number of transformants. Plasmids were prepared from the respective transformants, and the plasmids were subjected to addition of 30 µg of RNase A and incubation at 37° C. for 1 hour. Subsequently, the mixtures were subjected to phenol extraction/chloroform extraction and ethanol precipitation to purify the DNAs, and they were each dissolved in a TE solution to a final concentration of 1.0 µg/µl. The base sequences thereof were determined by the dideoxy chain termination method using a sequencing kit and an Autosequencer 373A manufactured by ABI.

As a result, it was found that the plasmids from the above-obtained transformants were such that the base sequence corresponding to the codon encoding the 37$^{th}$ amino acid in the amino acid sequence of the β-subunit of *Pseudonocardia thermophila* JCM3095-derived nitrile hydratase had been changed to a base sequence corresponding to the codon encoding an amino acid other than Phe, as compared with pPT-DB1.

In Table 131 below, the numbers of the obtained transformants as well as the corresponding mutated sites, changes in amino acid sequence and changes in base sequence are given.

TABLE 131

| Number | Mutated site | Change in amino acid sequence | | Change in base sequence | |
|---|---|---|---|---|---|
| | | Before mutation | After mutation | Before mutation | After mutation |
| No. 54 | 37$^{th}$ position in β-subunit | Phe | Thr | ttc | acc |
| No. 55 | 37$^{th}$ position in β-subunit | Phe | Ala | ttc | gcc |
| No. 56 | 37$^{th}$ position in β-subunit | Phe | Leu | ttc | ctc |
| No. 57 | 37$^{th}$ position in β-subunit | Phe | Ile | ttc | atc |
| No. 58 | 37$^{th}$ position in β-subunit | Phe | Val | ttc | gtc |

Example 99

Introduction of Mutation for Construction of Modified Enzyme (12)

Onto a plasmid: pPT-DB1 containing the ORF that codes for the *Pseudonocardia thermophila* JCM3095-derived nitrile hydratase as constructed from MT10822 in Example 83, mutation was performed to change the 40$^{th}$ Thr of the amino acid sequence of the β-subunit, which is the target of mutation as extracted in Example 86 or 87, to another amino acid.

Using 10 ng of pPT1-DB1 as the template, PCRs of two different types we re carried out. For the PCR reaction No. 1, a reaction system of 50 µl in total comprising 5.0 pmol of the primer having the sequence as forth in SEQ ID NO: 121 in the Sequence Listing and 50 pmol of an M13 primer M4 (having the sequence as set forth in SEQ ID NO: 107 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes. For the PCR reaction No. 2, a reaction system of 50 µl in total comprising 50 pmol of an MUT4 primer (having the sequence as set forth in SEQ ID NO: 108 in the Sequence Listing) and 50 pmol of an M13 primer RV (having the sequence as set forth in SEQ ID NO: 109 in the Sequence Listing) (for the composition of the system, the manufacturer's instructions for the kit were followed) was used, and the reaction was carried out following the same procedure as the PCR reaction No. 1.

Thereafter, the same procedure as in Example 89 was carried out to obtain a number of transformants. Plasmids were prepared from the respective transformants, and the plasmids were subjected to addition of 30 µg of RNase A and incubation at 37° C. for 1 hour. Subsequently, the mixtures were subjected to phenol extraction/chloroform extraction and ethanol precipitation to purify the DNAs, and they were each dissolved in a TE solution to a final concentration of 1.0 µg/µl. The base sequences thereof were determined by the dideoxy chain termination method using a sequencing kit and an Autosequencer 373A manufactured by ABI.

As a result, it was found that the plasmids from the above-obtained transformants were such that the base sequence corresponding to the codon encoding the $40^{th}$ amino acid in the amino acid sequence of the β-subunit of *Pseudonocardia thermophila* JCM3095-derived nitrile hydratase had been changed to a base sequence corresponding to the codon encoding an amino acid other than Thr, as compared with pPT-DB1.

In Table 132 below, the numbers of the obtained transformants as well as the corresponding mutated sites, changes in amino acid sequence and changes in base sequence are given.

TABLE 132

| Number | Mutated site | Change in amino acid sequence | | Change in base sequence | |
|---|---|---|---|---|---|
| | | Before mutation | After mutation | Before mutation | After mutation |
| No. 58a | $40^{th}$ position in β-subunit | Thr | Val | acg | gtg |
| No. 58b | $40^{th}$ position in β-subunit | Thr | Leu | acg | ctg |
| No. 58c | $40^{th}$ position in β-subunit | Thr | Ile | acg | att |

Example 100

Introduction of Mutation for Construction of Modified Enzyme (13)

Onto a plasmid: pPT-DB1 containing the ORF that codes for the *Pseudonocardia thermophila* JCM3095-derived nitrile hydratase as constructed from MT10822 in Example 83, mutation was performed to change the $41^{st}$ Phe of the amino acid sequence of the β-subunit, which is the target of mutation as extracted in Example 86 or 87, to another amino acid.

Using 10 ng of pPT-DB1 as the template, PCRs of two different types were carried out. For the PCR reaction No. 1, a reaction system of 50 µl in total comprising 50 pmol of the primer having the sequence as forth in SEQ ID NO: 122 in the Sequence Listing and 50 pmol of an M13 primer M4 (having the sequence as set forth in SEQ ID NO: 107 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes. For the PCR reaction No. 2, a reaction system of 50 µl in total comprising 50 pmol of an MUT4 primer (having the sequence as set forth in SEQ ID NO: 108 in the Sequence Listing) and 50 pmol of an M13 primer RV (having the sequence as set forth in SEQ ID NO: 109 in the Sequence Listing) (for the composition of the system, the manufacturer's instructions for the kit were followed) was used, and the reaction was carried out following the same procedure as the PCR reaction No. 1.

Thereafter, the same procedure as in Example 89 was carried out to obtain a number of transformants. Plasmids were prepared from the respective transformants, and the plasmids were subjected to addition of 30 µg of RNase A and incubation at 37° C. for 1 hour. Subsequently, the mixtures were subjected to phenol extraction/chloroform extraction and ethanol precipitation to purify the DNAs, and they were each dissolved in a TE solution to a final concentration of 1.0 µg/µl. The base sequences thereof were determined by the dideoxy chain termination method using a sequencing kit and an Autosequencer 373A manufactured by ABI.

As a result, it was found that the plasmids from the above-obtained transformants were such that the base sequence corresponding to the codon encoding the $41^{st}$ amino acid in the amino acid sequence of the β-subunit of *Pseudonocardia thermophila* JCM3095-derived nitrile hydratase had been changed to a base sequence corresponding to the codon encoding an amino acid other than Phe, as compared with pPT-DB1.

In Table 133 below, the numbers of the obtained transformants as well as the corresponding mutated sites, changes in amino acid sequence and changes in base sequence are given.

TABLE 133

| Number | Mutated site | Change in amino acid sequence | | Change in base sequence | |
|---|---|---|---|---|---|
| | | Before mutation | After mutation | Before mutation | After mutation |
| No. 59 | $41^{st}$ position in β-subunit | Phe | Glu | ttc | gaa |
| No. 60 | $41^{st}$ position in β-subunit | Phe | Thr | ttc | acc |
| No. 61 | $41^{st}$ position in β-subunit | Phe | Ala | ttc | gcc |
| No. 62 | $41^{st}$ position in β-subunit | Phe | Leu | ttc | ctc |
| No. 63 | $41^{st}$ position in β-subunit | Phe | Ile | ttc | atc |
| No. 64 | $41^{st}$ position in β-subunit | Phe | Val | ttc | gtc |

Example 101

Introduction of Mutation for Construction of Modified Enzyme (14)

Onto a plasmid: pPT-DB1 containing the ORF that codes for the *Pseudonocardia thermophila* JCM3095-derived nitrile hydratase as constructed from MT10822 in Example 83, mutation was performed to change the $46^{th}$ Met of the amino acid sequence of the β-subunit, which is the target of mutation as extracted in Example 86 or 87, to another amino acid.

Using 10 ng of pPT-DB1 as the template, PCRs of two different types were carried out. For the PCR reaction No. 1, a reaction system of 50 µl in total comprising 50 pmol of the primer having the sequence as forth in SEQ ID NO: 123 in the Sequence Listing and 50 pmol of an M13 primer M4 (having the sequence as set forth in SEQ ID NO: 107 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes. For the PCR reaction No. 2, a reaction system of 50 µl in total comprising 50 pmol of an MUT4 primer (having the sequence as set forth in SEQ ID NO: 108 in the Sequence Listing) and 50 pmol of an M13 primer RV (having the sequence as set forth in SEQ ID NO: 109 in the Sequence Listing) (for the composition of the system, the manufacturer's instructions for the kit were followed) was used, and the reaction was carried out following the same procedure as the PCR reaction No. 1.

Thereafter, the same procedure as in Example 89 was carried out to obtain a number of transformants. Plasmids were prepared from the respective transformants, and the plasmids were subjected to addition of 30 μg of RNase A and incubation at 37° C. for 1 hour. Subsequently, the mixtures were subjected to phenol extraction/chloroform extraction and ethanol precipitation to purify the DNAs, and they were each dissolved in a TE solution to a final concentration of 1.0 μg/μl. The base sequences thereof were determined by the dideoxy chain termination method using a sequencing kit and an Autosequencer 373A manufactured by ABI.

As a result, it was found that the plasmids from the above-obtained transformants were such that the base sequence corresponding to the codon encoding the 46$^{th}$ amino acid in the amino acid sequence of the β-subunit of *Pseudonocardia thermophila* JCM3095-derived nitrile hydratase had been changed to a base sequence corresponding to the codon encoding an amino acid other than Met, as compared with pPT-DB1.

In Table 134 below, the numbers of the obtained transformants as well as the corresponding mutated sites, changes in amino acid sequence and changes in base sequence are given.

TABLE 134

| Number | Mutated site | Change in amino acid sequence | | Change in base sequence | |
|---|---|---|---|---|---|
| | | Before mutation | After mutation | Before mutation | After mutation |
| No. 65 | 46$^{th}$ position in β-subunit | Met | Gly | atg | ggg |
| No. 66 | 46$^{th}$ position in β-subunit | Met | Tyr | atg | tat |
| No. 67 | 46$^{th}$ position in β-subunit | Met | Leu | atg | ctg |
| No. 68 | 46$^{th}$ position in β-subunit | Met | Lys | atg | aag |
| No. 69 | 46$^{th}$ position in β-subunit | Met | Asp | atg | gat |

Example 102

Introduction of Mutation for Construction of Modified Enzyme (15)

Onto a plasmid: pPT-DB1 containing the ORF that codes for the *Pseudonocardia thermophila* JCM3095-derived nitrile hydratase as constructed from MT10822 in Example 83, mutation was performed to change the 48$^{th}$ Leu of the amino acid sequence of the β-subunit, which is the target of mutation as extracted in Example 86 or 87, to another amino acid.

Using 10 ng of pPT-DB1 as the template, PCRs of two different types were carried out. For the PCR reaction No. 1, a reaction system of 50 μl in total comprising 50 pmol of the primer having the sequence as forth in SEQ ID NO: 124 in the Sequence Listing and 50 pmol of an M13 primer M4 (having the sequence as set forth in SEQ ID NO: 107 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes. For the PCR reaction No. 2, a reaction system of 50 μl in total comprising 50 pmol of an MUT4 primer (having the sequence as set forth in SEQ ID NO: 108 in the Sequence Listing) and 50 pmol of an M13 primer RV (having the sequence as set forth in SEQ ID NO: 109 in the Sequence Listing) (for the composition of the system, the manufacturer's instructions for the kit were followed) was used, and the reaction was carried out following the same procedure as the PCR reaction No. 1.

Thereafter, the same procedure as in Example 89 was carried out to obtain a number of transformants. Plasmids were prepared from the respective transformants, and the plasmids were subjected to addition of 30 μg of RNase A and incubation at 37° C. for 1 hour. Subsequently, the mixtures were subjected to phenol extraction/chloroform extraction and ethanol precipitation to purify the DNAs, and they were each dissolved in a TE solution to a final concentration of 1.0 μg/μl. The base sequences thereof were determined by the dideoxy chain termination method using a sequencing kit and an Autosequencer 373A manufactured by ABI.

As a result, it was found that the plasmids from the above-obtained transformants were such that the base sequence corresponding to the codon encoding the 48$^{th}$ amino acid in the amino acid sequence of the β-subunit of *Pseudonocardia thermophila* JCM3095-derived nitrile hydratase had been changed to a base sequence corresponding to the codon encoding an amino acid other than Leu, as compared with pPT-DB1.

In Table 135 below, the numbers of the obtained transformants as well as the corresponding mutated sites, changes in amino acid sequence and changes in base sequence are given.

TABLE 135

| Number | Mutated site | Change in amino acid sequence | | Change in base sequence | |
|---|---|---|---|---|---|
| | | Before mutation | After mutation | Before mutation | After mutation |
| No. 70 | 48$^{th}$ position in β-subunit | Leu | Gly | ctg | ggg |
| No. 71 | 48$^{th}$ position in β-subunit | Leu | Ala | ctg | gcg |
| No. 72 | 48$^{th}$ position in β-subunit | Leu | Val | ctg | gtg |
| No. 73 | 48$^{th}$ position in β-subunit | Leu | Ser | ctg | tcg |
| No. 74 | 48$^{th}$ position in β-subunit | Leu | Thr | ctg | acg |
| No. 75 | 48$^{th}$ position in β-subunit | Leu | Arg | ctg | cgg |

Example 103

Introduction of Mutation for Construction of Modified Enzyme (16)

Onto a plasmid: pPT-DB1 containing the ORF that codes for the *Pseudonocardia thermophila* JCM3095-derived nitrile hydratase as constructed from MT10822 in Example 83, mutation was performed to change the 51$^{st}$ Phe of the amino acid sequence of the β-subunit, which is the target of mutation as extracted in Example 86 or 87, to another amino acid.

Using 10 ng of pPT-DB1 as the template, PCRs of two different types were carried out. For the PCR reaction No. 1, a reaction system of 50 μl in total comprising 50 pmol of the primer having the sequence as forth in SEQ ID NO: 125 in the Sequence Listing and 50 pmol of an M13 primer M4 (having the sequence as set forth in SEQ ID NO: 107 in the Sequence Listing) (for the composition of the system, the manufacturer's instructions for the kit were followed) was used, and the reaction consisted of 25 PCR cycles, in which one PCR cycle comrised thermal denaturation (98° C.) for 15 seconds, annealing (55° C.) for 30 seconds and chain extension (72° C.) for 2 minutes. For the PCR reaction No. 2, a reaction system of 50 µl in total comprising 50 pmol of an MUT4 primer (having the sequence as set forth in SEQ ID NO: 108 in the Sequence Listing) and 50 pmol of an M13 primer RV (having the sequence as set forth in SEQ ID NO: 109 in the Sequence Listing) (for the composition of the system, the manufacturer's instructions for the kit were followed) was used, and the reaction was carried out following the same procedure as the PCR reaction No. 1.

Thereafter, the same procedure as in Example 89 was carried out to obtain a number of transformants. Plasmids were prepared from the respective transformants, and the plasmids were subjected to addition of 30 µg of RNase A and incubation at 37° C. for 1 hour. Subsequently, the mixtures were subjected to phenol extraction/chloroform extraction and ethanol precipitation to purify the DNAs, and they were each dissolved in a TE solution to a final concentration of 1.0 µg/µl. The base sequences thereof were determined by the dideoxy chain termination method using a sequencing kit and an Autosequencer 373A manufactured by ABI.

As a result, it was found that the plasmids from the above-obtained transformants were such that the base sequence corresponding to the codon encoding the $51^{th}$ amino acid in the amino acid sequence of the β-subunit of *Pseudonocardia thermophila* JCM3095-derived nitrile hydratase had been changed to a base sequence corresponding to the codon encoding an amino acid other than Phe, as compared with pPT-DB1.

In Table 136 below, the numbers of the obtained transformants as well as the corresponding mutated sites, changes in amino acid sequence and changes in base sequence are given.

TABLE 136

| Number | Mutated site | Change in amino acid sequence | | Change in base sequence | |
|---|---|---|---|---|---|
| | | Before mutation | After mutation | Before mutation | After mutation |
| No. 76 | $51^{st}$ position in β-subunit | Phe | Ala | ttc | gcc |
| No. 77 | $51^{st}$ position in β-subunit | Phe | Val | ttc | gtc |

Example 104

Introduction of Mutation for Construction of Modified Enzyme (17)

Onto a plasmid: pPT-DB1 containing the ORF that codes for the *Pseudonocardia thermophila* JCM3095-derived nitrile hydratase as constructed from MT10822 in Example 83, mutation was performed to change the $61^{st}$ Ala of the amino acid sequence of the β-subunit, which is the target of mutation as extracted in Example 86 or 87, to another amino acid.

Using 10 ng of pPT-DB1 as the template, PCRs of two different types were carried out. For the PCR reaction No. 1, a reaction system of 50 µl in total comprising 50 pmol of the primer having the sequence as forth in SEQ ID NO: 126 in the Sequence Listing and 50 pmol of an M13 primer M4 (having the sequence as set forth in SEQ ID NO: 107 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes. For the PCR reaction No. 2, a reaction system of 50 µl in total comprising 50 pmol of an MUT4 primer (having the sequence as set forth in SEQ ID NO: 108 in the Sequence Listing) and 50 pmol of an M13 primer RV (having the sequence as set forth in SEQ ID NO: 109 in the Sequence Listing) (for the composition of the system, the manufacturer's instructions for the kit were followed) was used, and the reaction was carried out following the same procedure as the PCR reaction No. 1.

Thereafter, the same procedure as in Example 89 was carried out to obtain a number of transformants. Plasmids were prepared from the respective transformants, and the plasmids were subjected to addition of 30 µg of RNase A and incubation at 37° C. for 1 hour. Subsequently, the mixtures were subjected to phenol extraction/chloroform extraction and ethanol precipitation to purify the DNAs, and they were each dissolved in a TE solution to a final concentration of 1.0 µg/µl. The base sequences thereof were determined by the dideoxy chain termination method using a sequencing kit and an Autosequencer 373A manufactured by ABI.

As a result, it was found that the plasmids from the above-obtained transformants were such that the base sequence corresponding to the codon encoding the $61^{st}$ amino acid in the amino acid sequence of the β-subunit of *Pseudonocardia thermophila* JCM3095-derived nitrile hydratase had been changed to a base sequence corresponding to the codon encoding an amino acid other than Ala, as compared with pPT-DB1.

In Table 137 below, the numbers of the obtained transformants as well as the corresponding mutated sites, changes in amino acid sequence and changes in base sequence are given.

TABLE 137

| Number | Mutated site | Change in amino acid sequence | | Change in base sequence | |
|---|---|---|---|---|---|
| | | Before mutation | After mutation | Before mutation | After mutation |
| No. 77a | $61^{st}$ position in β-subunit | Ala | Val | gcc | gtc |
| No. 77b | $61^{st}$ position in β-subunit | Ala | Leu | gcc | ctc |
| No. 77c | $61^{st}$ position in β-subunit | Ala | Gly | gcc | ggc |
| No. 77d | $61^{st}$ position in β-subunit | Ala | Ser | gcc | tcg |
| No. 77e | $61^{st}$ position in β-subunit | Ala | Thr | gcc | acg |
| No. 77f | $61^{st}$ position in β-subunit | Ala | Trp | gcc | tgg |

Example 105

Introduction of Mutation for Construction of Modified Enzyme (18)

Onto a plasmid: pPT-DB1 containing the ORF that codes for the *Pseudonocardia thermophila* JCM3095-derived nitrile hydratase as constructed from MT10822 in Example 83, mutation was performed to change the $72^{nd}$ Trp of the amino acid sequence of the β-subunit, which is the target of mutation as extracted in Example 86 or 87, to another amino acid.

Using 10 ng of pPT-DB1 as the template, PCRs of two different types were carried out. For the PCR reaction No. 1, a reaction system of 50 µl in total comprising 50 pmol of the primer having the sequence as forth in SEQ ID NO: 127 in the Sequence Listing and 50 pmol of an M13 primer M4 (having the sequence as set forth in SEQ ID NO: 107 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes. For the PCR reaction No. 2, a reaction system of 50 µl in total comprising 50 pmol of an MUT4 primer (having the sequence as set forth in SEQ ID NO: 108 in the Sequence Listing) and 50 pmol of an M13 primer RV (having the sequence as set forth in SEQ ID NO: 109 in the Sequence Listing) (for the composition of the system, the manufacturer's instructions for the kit were followed) was used, and the reaction was carried out following the same procedure as the PCR reaction No. 1.

Thereafter, the same procedure as in Example 89 was carried out to obtain a number of transformants. Plasmids were prepared from the respective transformants, and the plasmids were subjected to addition of 30 µg of RNase A and incubation at 37° C. for 1 hour. Subsequently, the mixtures were subjected to phenol extraction/chloroform extraction and ethanol precipitation to purify the DNAs, and they were each dissolved in a TE solution to a final concentration of 1.0 µg/µl. The base sequences thereof were determined by the dideoxy chain termination method using a sequencing kit and an Autosequencer 373A manufactured by ABI.

As a result, it was found that the plasmids from the above-obtained transform ants were such that the base sequence corresponding to the codon encoding the $72^{nd}$ amino acid in the amino acid sequence of the β-subunit of *Pseudonocardia thermophila* JCM3095-derived nitrile hydratase had been changed to a base sequence corresponding to the codon encoding an amino acid other than Trp, as compared with pPT-DB1.

In Table 138 below, the numbers of the obtained transformants as well as the corresponding mutated sites, changes in amino acid sequence and changes in base sequence are given.

TABLE 138

| | | Change in amino acid sequence | | Change in base sequence | |
|---|---|---|---|---|---|
| Number | Mutated site | Before mutation | After mutation | Before mutation | After mutation |
| No. 78 | $72^{nd}$ position in β-subunit | Trp | Phe | tgg | ttt |

Example 106

Introduction of Mutation for Construction of Modified Enzyme, (19)

Onto a plasmid: pPT-DB1 containing the ORF that codes for the *Pseudonocardia thermophila* JCM3095-derived nitrile hydratase as constructed from MT10822 in Example 83, mutation was performed to change the $112^{th}$ Lys of the amino acid sequence of the β-subunit, which is the target of mutation as extracted in Example 86 or 87, to another amino acid.

Using 10 ng of pPT-DB1 as the template, PCRs of two different types were carried out. For the PCR reaction No. 1, a reaction system of 50 µl in total comprising 50 pmol of the primer having the sequence as forth in SEQ ID NO: 128 in the Sequence Listing and 50 pmol of an M13 primer M4 (having the sequence as set forth in SEQ ID NO: 107 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes. For the PCR reaction No. 2, a reaction system of 50 µl in total comprising 50 pmol of an MUT4 primer (having the sequence as set forth in SEQ ID NO: 108 in the Sequence Listing) and 50 pmol of an M13 primer RV (having the sequence as set forth in SEQ ID NO: 109 in the Sequence Listing) (for the composition of the system, the manufacturer's instructions for the kit were followed) was used, and the reaction was carried out following the same procedure as the PCR reaction No. 1.

Thereafter, the same procedure as in Example 89 was carried out to obtain a number of transformants. Plasmids were prepared from the respective transformants, and the plasmids were subjected to addition of 30 µg of RNase A and incubation at 37° C. for 1 hour. Subsequently, the mixtures were subjected to phenol extraction/chloroform extraction and ethanol precipitation to purify the DNAs, and they were each dissolved in a TE solution to a final concentration of 1.0 µg/µl. The base sequences thereof were determined by the dideoxy chain termination method using a sequencing kit and an Autosequencer 373A manufactured by ABI.

As a result, it was found that the plasmids from the above-obtained transformants were such that the base sequence corresponding to the codon encoding the $112^{th}$ amino acid in the amino acid sequence of the β-subunit of *Pseudonocardia thermophila* JCM3095-derived nitrile hydratase had been changed to a base sequence corresponding to the codon encoding an amino acid other than Lys, as compared with pPT-DB1.

In Table 139 below, the numbers of the obtained transformants as well as the corresponding mutated sites, changes in amino acid sequence and changes in base sequence are given.

TABLE 139

| | | Change in amino acid sequence | | Change in base sequence | |
|---|---|---|---|---|---|
| Number | Mutated site | Before mutation | After mutation | Before mutation | After mutation |
| No. 78a | $112^{th}$ position in β-subunit | Lys | Val | aag | gtg |
| No. 78b | $112^{th}$ position in β-subunit | Lys | Ile | aag | att |

Example 107

Introduction of Mutation for Construction of Modified Enzyme (20)

Onto a plasmid: pPT-DB1 containing the ORF that codes for the *Pseudonocardia thermophila* JCM3095-derived nitrile hydratase as constructed from MT10822 in Example 83, mutation was performed to change the 118$^{th}$ Phe of the amino acid sequence of the β-subunit, which is the target of mutation as extracted in Example 86 or 87, to another amino acid.

Using 10 ng of pPT-DB1 as the template, PCRs of two different types were carried out. For the PCR reaction No. 1, a reaction system of 50 µl in total comprising 50 pmol of the primer having the sequence as forth in SEQ ID NO: 129 in the Sequence Listing and 50 pmol of an M13 primer M4 (having the sequence as set forth in SEQ ID NO: 107 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes. For the PCR reaction No. 2, a reaction system of 50 µl in total comprising 50 pmol of an MUT4 primer (having the sequence as set forth in SEQ ID NO: 108 in the Sequence Listing) and 50 pmol of an M13 primer RV (having the sequence as set forth in SEQ ID NO: 109 in the Sequence Listing) (for the composition of the system, the manufacturer's instructions for the kit were followed) was used, and the reaction was carried out following the same procedure as the PCR reaction No. 1.

Thereafter, the same procedure as in Example 89 was carried out to obtain a number of transformants. Plasmids were prepared from the respective transformants, and the plasmids were subjected to addition of 30 µg of RNase A and incubation at 37° C. for 1 hour. Subsequently, the mixtures were subjected to phenol extraction/chloroform extraction and ethanol precipitation to purify the DNAs, and they were each dissolved in a TE solution to a final concentration of 1.0 µg/µl. The base sequences thereof were determined by the dideoxy chain termination method using a sequencing kit and an Autosequencer 373A manufactured by ABI.

As a result, it was found that the plasmids from the above-obtained transformants were such that the base sequence corresponding to the codon encoding the 118$^{th}$ amino acid in the amino acid sequence of the β-subunit of *Pseudonocardia thermophila* JCM3095-derived nitrile hydratase had been changed to a base sequence corresponding to the codon encoding an amino acid other than Phe, as compared with pPT-DB1.

In Table 140 below, the numbers of the obtained transformants as well as the corresponding mutated sites, changes in amino acid sequence and changes in base sequence are given.

TABLE 140

| Number | Mutated site | Change in amino acid sequence | | Change in base sequence | |
|---|---|---|---|---|---|
| | | Before mutation | After mutation | Before mutation | After mutation |
| No. 79 | 118$^{th}$ position in β-subunit | Phe | Ala | ttc | gcc |
| No. 80 | 118$^{th}$ position in β-subunit | Phe | Leu | ttc | ctc |
| No. 81 | 118$^{th}$ position in β-subunit | Phe | Ile | ttc | atc |
| No. 82 | 118$^{th}$ position in β-subunit | Phe | Val | ttc | gtc |

Example 108

Introduction of Mutation for Construction of Modified Enzyme (21)

Onto a plasmid: pPT-DB1 containing the ORF that codes for the *Pseudonocardia thermophila* JCM3095-derived nitrile hydratase as constructed from MT10822 in Example 83, mutation was performed to change the 127$^{th}$ Leu of the amino acid sequence of the β-subunit, which is the target of mutation as extracted in Example 86 or 87, to another amino acid.

Using 10 ng of pPT-DB1 as the template, PCRs of two different types were carried out. For the PCR reaction No. 1, a reaction system of 50 µl in total comprising 50 pmol of the primer having the sequence as forth in SEQ ID NO: 130 in the Sequence Listing and 50 pmol of an M13 primer M4 (having the sequence as set forth in SEQ ID NO: 107 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes. For the PCR reaction No. 2, a reaction system of 50 µl in total comprising 50 pmol of an MUT4 primer (having the sequence as set forth in SEQ ID NO: 108 in the Sequence Listing) and 50 pmol of an M13 primer RV (having the sequence as set forth in SEQ ID NO: 109 in the Sequence Listing) (for the composition of the system, the manufacturer's instructions for the kit were followed) was used, and the reaction was carried out following the same procedure as the PCR reaction No. 1.

Thereafter, the same procedure as in Example 89 was carried out to obtain a number of transformants. Plasmids were prepared from the respective transformants, and the plasmids were subjected to addition of 30 µg of RNase A and incubation at 37° C. for 1 hour. Subsequently, the mixtures were subjected to phenol extraction/chloroform extraction and ethanol precipitation to purify the DNAs, and they were each dissolved in a TE solution to a final concentration of 1.0 µg/µl. The base sequences thereof were determined by the dideoxy chain termination method using a sequencing kit and an Autosequencer 373A manufactured by ABI.

As a result, it was found that the plasmids from the above-obtained transformants were such that the base sequence corresponding to the codon encoding the 127$^{th}$ amino acid in the amino acid sequence of the β-subunit of *Pseudonocardia thermophila* JCM3095-derived nitrile hydratase had been changed to a base sequence corresponding to the codon encoding an amino acid other than Leu, as compared with pPT-DB1.

In Table 141 below, the numbers of the obtained transformants as well as the corresponding mutated sites, changes in amino acid sequence and changes in base sequence are given.

TABLE 141

| Number | Mutated site | Change in amino acid sequence | | Change in base sequence | |
|---|---|---|---|---|---|
| | | Before mutation | After mutation | Before mutation | After mutation |
| No. 83 | 127th position in β-subunit | Leu | Ala | ctg | gcg |
| No. 84 | 127th position in β-subunit | Leu | Val | ctg | gtg |
| No. 85 | 127th position in β-subunit | Leu | Ser | ctg | tcg |

Example 109

Introduction of Mutation for Construction of Modified Enzyme (22)

Onto a plasmid: pPT-DB1 containing the ORF that codes for the *Pseudonocardia thermophila* JCM3095-derived nitrile hydratase as constructed from MT10822 in Example 83, mutation was performed to change the 146th Arg of the amino acid sequence of the β-subunit, which is the target of mutation as extracted in Example 86 or 87, to another amino acid.

Using 10 ng of pPT-DB1 as the template, PCRs of two different types were carried out. For the PCR reaction No. 1, a reaction system of 50 μl in total comprising 50 pmol of the primer having the sequence as forth in SEQ ID NO: 131 in the Sequence Listing and 50 pmol of an M13 primer M4 (having the sequence as set forth in SEQ ID NO: 107 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes. For the PCR reaction No. 2, a reaction system of 50 μl in total comprising 50 pmol of an MUT4 primer (having the sequence as set forth in SEQ ID NO: 108 in the Sequence Listing) and 50 pmol of an M13 primer RV (having the sequence as set forth in SEQ ID NO: 109 in the Sequence Listing) (for the composition of the system, the manufacturer's instructions for the kit were followed) was used, and the reaction was carried out following the same procedure as the PCR reaction No. 1.

Thereafter, the same procedure as in Example 89 was carried out to obtain a number of transformants. Plasmids were prepared from the respective transformants, and the plasmids were subjected to addition of 30 μg of RNase A and incubation at 37° C. for 1 hour. Subsequently, the mixtures were subjected to phenol extraction/chloroform extraction and ethanol precipitation to purify the DNAs, and they were each dissolved in a TE solution to a final concentration of 1.0 μg/μl. The base sequences thereof were determined by the dideoxy chain termination method using a sequencing kit and an Autosequencer 373A manufactured by ABI.

As a result, it was found that the plasmids from the above-obtained transformants were such that the base sequence corresponding to the codon encoding the 146th amino acid in the amino acid sequence of the β-subunit of *Pseudonocardia thermophila* JCM3095-derived nitrile hydratase had been changed to a base sequence corresponding to the codon encoding an amino acid other than Arg, as compared with pPT-DB1.

In Table 142 below, the numbers of the obtained transformants as well as the corresponding mutated sites, changes in amino acid sequence and changes in base sequence are given.

TABLE 142

| Number | Mutated site | Change in amino acid sequence | | Change in base sequence | |
|---|---|---|---|---|---|
| | | Before mutation | After mutation | Before mutation | After mutation |
| No. 86 | 146th position in β-subunit | Arg | Gly | cgg | ggg |

Example 110

Introduction of Mutation for Construction of Modified Enzyme (23)

Onto a plasmid: pPT-DB1 containing the ORF that codes for the *Pseudonocardia thermophila* JCM3095-derived nitrile hydratase as constructed from MT10822 in Example 83, mutation was performed to change the 150th Ala of the amino acid sequence of the β-subunit, which is the target of mutation as extracted in Example 86 or 87, to another amino acid.

Using 10 ng of pPT-DB1 as the template, PCRs of two different types were carried out. For the PCR reaction No. 1, a reaction system of 50 μl in total comprising 50 pmol of the primer having the sequence as forth in SEQ ID NO: 132 in the Sequence Listing and 50 pmol of an M13 primer M4 (having the sequence as set forth in SEQ ID NO: 107 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes. For the PCR reaction No. 2, a reaction system of 50 μl in total comprising 50 pmol of an MUT4 primer (having the sequence as set forth in SEQ ID NO: 108 in the Sequence Listing) and 50 pmol of an M13 primer RV (having the sequence as set forth in SEQ ID NO: 109 in the Sequence Listing) (for the composition of the system, the manufacturer's instructions for the kit were followed) was used, and the reaction was carried out following the same procedure as the PCR reaction No. 1.

Thereafter, the same procedure as in Example 89 was carried out to obtain a number of transformants. Plasmids were prepared from the respective transformants, and the plasmids were subjected to addition of 30 μg of RNase A and incubation at 37° C. for 1 hour. Subsequently, the mixtures were subjected to phenol extraction/chloroform extraction and ethanol precipitation to purify the DNAs, and they were each dissolved in a TE solution to a final concentration of 1.0 μg/μl. The base sequences thereof were determined by the dideoxy chain termination method using a sequencing kit and an Autosequencer 373A manufactured by ABI.

As a result, it was found that the plasmids from the above-obtained transformants were such that the base sequence corresponding to the codon encoding the 150th amino acid in the amino acid sequence of the β-subunit of *Pseudonocardia thermophila* JCM3095-derived nitrile hydratase had been changed to a base sequence corresponding to the codon encoding an amino acid other than Ala, as compared with pPT-DB1.

In Table 143 below, the numbers of the obtained transformants as well as the corresponding mutated sites, changes in amino acid sequence and changes in base sequence are given.

TABLE 143

| Number | Mutated site | Change in amino acid sequence | | Change in base sequence | |
|---|---|---|---|---|---|
| | | Before mutation | After mutation | Before mutation | After mutation |
| No. 86a | 150$^{th}$ position in β-subunit | Ala | Ser | gcg | tcg |
| No. 86b | 150$^{th}$ position in β-subunit | Ala | Asn | gcg | aat |

Example 111

Introduction of Mutation for Construction of Modified Enzyme (24)

Onto a plasmid: pPT-DB1 containing the ORF that codes for the *Pseudonocardia thermophila* JCM3095-derived nitrile hydratase as constructed from MT10822 in Example 83, mutation was performed to change the 160$^{th}$ Arg of the amino acid sequence of the β-subunit, which is the target of mutation as extracted in Example 86 or 87, to another amino acid.

Using 10 ng of pPT-DB1 as the template, PCRs of two different types were carried out. For the PCR reaction No. 1, a reaction system of 50 μl in total comprising 50 pmol of the primer having the sequence as forth in SEQ ID NO: 133 in the Sequence Listing and 50 pmol of an M13 primer M4 (having the sequence as set forth in SEQ ID NO: 107 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes. For the PCR reaction No. 2, a reaction system of 50 μl in total comprising 50 pmol of an MUT4 primer (having the sequence as set forth in SEQ ID NO: 108 in the Sequence Listing) and 50 pmol of an M13 primer RV (having the sequence as set forth in SEQ ID NO: 109 in the Sequence Listing) (for the composition of the system, the manufacturer's instructions for the kit were followed) was used, and the reaction was carried out following the same procedure as the PCR reaction No. 1.

Thereafter, the same procedure as in Example 89 was carried out to obtain a number of transformants. Plasmids were prepared from the respective transformants, and the plasmids were subjected to addition of 30 μg of RNase A and incubation at 37° C. for 1 hour. Subsequently, the mixtures were subjected to phenol extraction/chloroform extraction and ethanol precipitation to purify the DNAs, and they were each dissolved in a TE solution to a final concentration of 1.0 μg/μl. The base sequences thereof were determined by the dideoxy chain termination method using a sequencing kit and an Autosequencer 373A manufactured by ABI.

As a result, it was found that the plasmids from the above-obtained transformants were such that the base sequence corresponding to the codon encoding the 160$^{th}$ amino acid in the amino acid sequence of the β-subunit of *Pseudonocardia thermophila* JCM3095-derived nitrile hydratase had been changed to a base sequence corresponding to the codon encoding an amino acid other than Arg, as compared with pPT-DB1.

In Table 144 below, the numbers of the obtained transformants as well as the corresponding mutated sites, changes in amino acid sequence and changes in base sequence are given.

TABLE 144

| Number | Mutated site | Change in amino acid sequence | | Change in base sequence | |
|---|---|---|---|---|---|
| | | Before mutation | After mutation | Before mutation | After mutation |
| No. 87 | 160$^{th}$ position in β-subunit | Arg | Leu | cgg | ctg |
| No. 88 | 160$^{th}$ position in β-subunit | Arg | Trp | cgg | tgg |
| No. 88a | 160$^{th}$ position in β-subunit | Arg | Met | cgg | atg |
| No. 88b | 160$^{th}$ position in β-subunit | Arg | Cys | cgg | tgt |

Example 112

Introduction of Mutation for Construction of Modified Enzyme (25)

Onto a plasmid: pPT-DB1 containing the ORF that codes for the *Pseudonocardia thermophila* JCM3095-derived nitrile hydratase as constructed from MT10822 in Example 83, mutation was performed to change the 68$^{th}$ Thr of the amino acid sequence of the β-subunit, which is the target of mutation as extracted in Example 86 or 87, to another amino acid.

Using 10 ng of pPT-DB1 as the template, PCRs of two different types were carried out. For the PCR reaction No. 1, a reaction system of 50 μl in total comprising 50 pmol of the primer having the sequence as forth in SEQ ID NO: 134 in the Sequence Listing and 50 pmol of an M13 primer M4 (having the sequence as set forth in SEQ ID NO: 107 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes. For the PCR reaction No. 2, a reaction system of 50 μl in total comprising 50 pmol of an MUT4 primer (having the sequence as set forth in SEQ ID NO: 108 in the Sequence Listing) and 50 pmol of an M13 primer RV (having the sequence as set forth in SEQ ID NO: 109 in the Sequence Listing) (for the composition of the system, the manufacturer's instructions for the kit were followed) was used, and the reaction was carried out following the same procedure as the PCR reaction No. 1.

Thereafter, the same procedure as in Example 89 was carried out to obtain a number of transformants. Plasmids were prepared from the respective transformants, and the plasmids were subjected to addition of 30 μg of RNase A and incubation at 37° C. for 1 hour. Subsequently, the mixtures were subjected to phenol extraction/chloroform extraction and ethanol precipitation to purify the DNAs, and they were each dissolved in a TE solution to a final concentration of 1.0 μg/μl.

The base sequences thereof were determined by the dideoxy chain termination method using a sequencing kit and an Autosequencer 373A manufactured by ABI.

As a result, it was found that the plasmids from the above-obtained transformants were such that the base sequence corresponding to the codon encoding the $168^{th}$ amino acid in the amino acid sequence of the β-subunit of *Pseudonocardia thermophila* JCM3095-derived nitrile hydratase had been changed to a base sequence corresponding to the codon encoding an amino acid other than Thr, as compared with pPT-DB1.

In Table 145 below, the numbers of the obtained transformants as well as the corresponding mutated sites, changes in amino acid sequence and changes in base sequence are given.

TABLE 145

| Number | Mutated site | Change in amino acid sequence | | Change in base sequence | |
|---|---|---|---|---|---|
| | | Before mutation | After mutation | Before mutation | After mutation |
| No. 88c | $168^{th}$ position in β-subunit | Thr | Glu | acg | gag |

Example 113

Introduction of Mutation for Construction of Modified Enzyme (26)

Onto a plasmid: pPT-DB1 containing the ORF that codes for the *Pseudonocardia thermophila* JCM3095-derived nitrile hydratase as constructed from MT10822 in Example 83, mutation was performed to change the $171^{st}$ Lys of the amino acid sequence of the β-subunit, which is the target of mutation as extracted in Example 86 or 87, to another amino acid.

Using 10 ng of pPT-DB1 as the template, PCRs of two different types were carried out. For the PCR reaction No. 1, a reaction system of 50 μl in total comprising 50 pmol of the primer having the sequence as forth in SEQ ID NO: 135 in the Sequence Listing and 50 pmol of an M13 primer M4 (having the sequence as set forth in SEQ ID NO: 107 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes. For the PCR reaction No. 2, a reaction system of 50 μl in total comprising 50 pmol of an MUT4 primer (having the sequence as set forth in SEQ ID NO: 108 in the Sequence Listing) and 50 pmol of an M13 primer RV (having the sequence as set forth in SEQ ID NO: 109 in the Sequence Listing) (for the composition of the system, the manufacturer's instructions for the kit were followed) was used, and the reaction was carried out following the same procedure as the PCR reaction No. 1.

Thereafter, the same procedure as in Example 89 was carried out to obtain a number of transformants. Plasmids were prepared from the respective transformants, and the plasmids were subjected to addition of 30 μg of RNase A and incubation at 37° C. for 1 hour. Subsequently, the mixtures were subjected to phenol extraction/chloroform extraction and ethanol precipitation to purify the DNAs, and they were each dissolved in a TE solution to a final concentration of 1.0 μg/μl.

The base sequences thereof were determined by the dideoxy chain termination method using a sequencing kit and an Autosequencer 373A manufactured by ABI.

As a result, it was found that the plasmids from the above-obtained transformants were such that the base sequence corresponding to the codon encoding the $171^{st}$ amino acid in the amino acid sequence of the β-subunit of *Pseudonocardia thermophila* JCM3095-derived nitrile hydratase had been changed to a base sequence corresponding to the codon encoding an amino acid other than Lys, as compared with pPT-DB1.

In Table 146 below, the numbers of the obtained transformants as well as the corresponding mutated sites, changes in amino acid sequence and changes in base sequence are given.

TABLE 146

| Number | Mutated site | Change in amino acid sequence | | Change in base sequence | |
|---|---|---|---|---|---|
| | | Before mutation | After mutation | Before mutation | After mutation |
| No. 88d | $171^{st}$ position in β-subunit | Lys | Ala | aag | gcg |

Example 114

Introduction of Mutation for Construction of Modified Enzyme (27)

Onto a plasmid: pPT-DB1 containing the ORF that codes for the *Pseudonocardia thermophila* JCM3095-derived nitrile hydratase as constructed from MT10822 in Example 83, mutation was performed to change the $176^{th}$ Tyr of the amino acid sequence of the β-subunit, which is the target of mutation as extracted in Example 86 or 87, to another amino acid.

Using 10 ng of pPT-DB1 as the template, PCRs of two different types were carried out. For the PCR reaction No. 1, a reaction system of 50 μl in total comprising 50 pmol of the primer having the sequence as forth in SEQ ID NO: 136 in the Sequence Listing and 50 pmol of an M13 primer M4 (having the sequence as set forth in SEQ ID NO: 107 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes. For the PCR reaction No. 2, a reaction system of 50 μl in total comprising 50 pmol of an MUT4 primer (having the sequence as set forth in SEQ ID NO: 108 in the Sequence Listing) and 50 pmol of an M13 primer RV (having the sequence as set forth in SEQ ID NO: 109 in the Sequence Listing) (for the composition of the system, the manufacturer's instructions for the kit were followed) was used, and the reaction was carried out following the same procedure as the PCR reaction No. 1.

Thereafter, the same procedure as in Example 89 was carried out to obtain a number of transformants. Plasmids were prepared from the respective transformants, and the plasmids were subjected to addition of 30 μg of RNase A and incubation at 37° C. for 1 hour. Subsequently, the mixtures were subjected to phenol extraction/chloroform extraction and ethanol precipitation to purify the DNAs, and they were each dissolved in a TE solution to a final concentration of 1.0 μg/μl.

The base sequences thereof were determined by the dideoxy chain termination method using a sequencing kit and an Autosequencer 373A manufactured by ABI.

As a result, it was found that the plasmids from the above-obtained transformants were such that the base sequence corresponding to the codon encoding the 176$^{th}$ amino acid in the amino acid sequence of the β-subunit of *Pseudonocardia thermophila* JCM3095-derived nitrile hydratase had been changed to a base sequence corresponding to the codon encoding an amino acid other than Tyr, as compared with pPT-DB1.

In Table 147 below, the numbers of the obtained transformants as well as the corresponding mutated sites, changes in amino acid sequence and changes in base sequence are given.

TABLE 147

| Number | Mutated site | Change in amino acid sequence | | Change in base sequence | |
|---|---|---|---|---|---|
| | | Before mutation | After mutation | Before mutation | After mutation |
| No. 88e | 176$^{th}$ position in β-subunit | Tyr | Ala | tac | gcc |
| No. 88f | 176$^{th}$ position in β-subunit | Tyr | Met | tac | atg |
| No. 88g | 176$^{th}$ position in β-subunit | Tyr | Cys | tac | tgc |
| No. 88h | 176$^{th}$ position in β-subunit | Tyr | Thr | tac | acc |

Example 115

Introduction of Mutation for Construction of Modified Enzyme (28)

Onto a plasmid: pPT-DB1 containing the ORF that codes for the *Pseudonocardia thermophila* JCM3095-derived nitrile hydratase as constructed from MT10822 in Example 83, mutation was performed to change the 186$^{th}$ Leu of the amino acid sequence of the β-subunit, which is the target of mutation as extracted in Example 86 or 87, to another amino acid.

Using 10 ng of pPT-DB1 as the template, PCRs of two different types were carried out. For the PCR reaction No. 1, a reaction system of 50 µl in total comprising 50 pmol of the primer having the sequence as forth in SEQ ID NO: 137 in the Sequence Listing and 50 pmol of an M13 primer M4 (having the sequence as set forth in SEQ ID NO: 107 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes. For the PCR reaction No. 2, a reaction system of 50 µl in total comprising 50 pmol of an MUT4 primer (having the sequence as set forth in SEQ ID NO: 108 in the Sequence Listing) and 50 pmol of an M13 primer RV (having the sequence as set forth in SEQ ID NO: 109 in the Sequence Listing) (for the composition of the system, the manufacturer's instructions for the kit were followed) was used, and the reaction was carried out following the same procedure as the PCR reaction No. 1.

Thereafter, the same procedure as in Example 89 was carried out to obtain a number of transformants. Plasmids were prepared from the respective transformants, and the plasmids were subjected to addition of 30 µg of RNase A and incubation at 37° C. for 1 hour. Subsequently, the mixtures were subjected to phenol extraction/chloroform extraction and ethanol precipitation to purify the DNAs, and they were each dissolved in a TE solution to a final concentration of 1.0 µg/µl. The base sequences thereof were determined by the dideoxy chain termination method using a sequencing kit and an Autosequencer 373A manufactured by ABI.

As a result, it was found that the plasmids from the above-obtained transformants were such that the base sequence corresponding to the codon encoding the 186$^{th}$ amino acid in the amino acid sequence of the β-subunit of *Pseudonocardia thermophila* JCM3095-derived nitrile hydratase had been changed to a base sequence corresponding to the codon encoding an amino acid other than Leu, as compared with pPT-DB1.

In Table 148 below, the numbers of the obtained transformants as well as the corresponding mutated sites, changes in amino acid sequence and changes in base sequence are given.

TABLE 148

| Number | Mutated site | Change in amino acid sequence | | Change in base sequence | |
|---|---|---|---|---|---|
| | | Before mutation | After mutation | Before mutation | After mutation |
| No. 89 | 186$^{th}$ position in β-subunit | Leu | Glu | ctg | gag |
| No. 90 | 186$^{th}$ position in β-subunit | Leu | Asp | ctg | gat |
| No. 91 | 186$^{th}$ position in β-subunit | Leu | Lys | ctg | aag |
| No. 92 | 186$^{th}$ position in β-subunit | Leu | Arg | ctg | cgg |
| No. 93 | 186$^{th}$ position in β-subunit | Leu | Asn | ctg | aac |
| No. 94 | 186$^{th}$ position in β-subunit | Leu | Ser | ctg | tcg |
| No. 95 | 186$^{th}$ position in β-subunit | Leu | Gly | ctg | ggg |

Example 116

Introduction of Mutation for Construction of Modified Enzyme (29)

Onto a plasmid: pPT-DB1 containing the ORF that codes for the *Pseudonocardia thermophila* JCM3095-derived nitrile hydratase as constructed from MT10822 in Example 83, mutation was performed to change the 217$^{th}$ Asp of the amino acid sequence of the β-subunit, which is the target of mutation as extracted in Example 86 or 87, to another amino acid.

Using 10 ng of pPT-DB1 as the template, PCRs of two different types were carried out. For the PCR reaction No. 1, a reaction system of 50 µl in total comprising 50 pmol of the primer having the sequence as forth in SEQ ID NO: 138 in the Sequence Listing and 50 pmol of an M13 primer M4 (having the sequence as set forth in SEQ ID NO: 107 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes. For the PCR reaction No. 2, a reaction system of 50 µl in total comprising 50 pmol of an MUT4 primer (having the sequence as set forth in SEQ ID NO: 108 in the Sequence Listing) and 50 pmol of an M13 primer RV (having the sequence as set forth in SEQ ID NO: 109 in the Sequence Listing) (for the composition of the system, the manufacturer's instructions for the kit were followed) was used, and the reaction was carried out following the same procedure as the PCR reaction No. 1.

Thereafter, the same procedure as in Example 89 was carried out to obtain a number of transformants. Plasmids were prepared from the respective transformants, and the plasmids were subjected to addition of 30 μg of RNase A and incubation at 37° C. for 1 hour. Subsequently, the mixtures were subjected to phenol extraction/chloroform extraction and ethanol precipitation to purify the DNAs, and they were each dissolved in a TE solution to a final concentration of 1.0 μg/μl. The base sequences thereof were determined by the dideoxy chain termination method using a sequencing kit and an Autosequencer 373A manufactured by ABI.

As a result, it was found that the plasmids from the above-obtained transformants were such that the base sequence corresponding to the codon encoding the 217$^{th}$ amino acid in the amino acid sequence of the β-subunit of *Pseudonocardia thermophila* JCM3095-derived nitrile hydratase had been changed to a base sequence corresponding to the codon encoding an amino acid other than Asp, as compared with pPT-DB1.

In Table 149 below, the numbers of the obtained transformants as well as the corresponding mutated sites, changes in amino acid sequence and changes in base sequence are given.

TABLE 149

| Number | Mutated site | Change in amino acid sequence | | Change in base sequence | |
|---|---|---|---|---|---|
| | | Before mutation | After mutation | Before mutation | After mutation |
| No. 96 | 217$^{th}$ position in β-subunit | Asp | Gly | gac | ggc |
| No. 96a | 217$^{th}$ position in β-subunit | Asp | Val | gac | gtc |
| No. 96b | 217$^{th}$ position in β-subunit | Asp | Leu | gac | ctc |
| No. 96c | 217$^{th}$ position in β-subunit | Asp | Met | gac | atg |
| No. 96d | 217$^{th}$ position in β-subunit | Asp | Cys | gac | tgt |
| No. 96e | 217$^{th}$ position in β-subunit | Asp | Ser | gac | agc |
| No. 96f | 217$^{th}$ position in β-subunit | Asp | Thr | gac | acc |
| No. 96g | 217$^{th}$ position in β-subunit | Asp | His | gac | cac |

Example 117

Introduction of Mutation for Construction of Modified Enzyme (30)

Onto a plasmid: pPT-DB1 containing the ORF that codes for the *Pseudonocardia thermophila* JCM3095-derived nitrile hydratase as constructed from MT10822 in Example 83, mutation was performed to change the 218$^{th}$ Cys of the amino acid sequence of the β-subunit, which is the target of mutation as extracted in Example 86 or 87, to another amino acid.

Using 10 ng of pPT-DB1 as the template, PCRs of two different types were carried out. For the PCR reaction No. 1, a reaction system of 50 μl in total comprising 50 pmol of an primer having the sequence as set forth in SEQ ID NO: 139 in the Sequence Listing and 50 pmol of an M13 primer M4 (having the sequence as set forth in SEQ ID NO: 107 in the Sequence Listing) (for the composition of the system, the manufacturer's instructions for the kit were followed) was used, and the reaction consisted of 25 PCR cycles, in which one PCR cycle comprised thermal denaturation (98° C.) for 15 seconds, annealing (55° C.) for 30 seconds and chain extension (72° C.) for 2 minutes. For the PCR reaction No. 2, a reaction system of 50 μl in total comprising 50 pmol of an MUT4 primer (having the sequence as set forth in SEQ ID NO: 108 in the Sequence Listing) and 50 pmol of an M13 primer RV (having the sequence as set forth in SEQ ID NO: 109 in the Sequence Listing) (for the composition of the system, the manufacturer's instructions for the kit were followed) was used, and the reaction was carried out following the same procedure as the PCR reaction No. 1.

Thereafter, the same procedure as in Example 89 was carried out to obtain a number of transformants. Plasmids were prepared from the respective transformants, and the plasmids were subjected to addition of 30 μg of RNase A and incubation at 37° C. for 1 hour. Subsequently, the mixtures were subjected to phenol extraction/chloroform extraction and ethanol precipitation to purify the DNAs, and they were each dissolved in a TE solution to a final concentration of 1.0 μg/μl. The base sequences thereof were determined by the dideoxy chain termination method using a sequencing kit and an Autosequencer 373A manufactured by ABI.

As a result, it was found that the plasmids from the above-obtained transformants were such that the base sequence corresponding to the codon encoding the 218$^{th}$ amino acid in the amino acid sequence of the β-subunit of *Pseudonocardia thermophila* JCM3095-derived nitrile hydratase had been changed to a base sequence corresponding to the codon encoding an amino acid other than Cys, as compared with pPT-DB1.

In Table 150 below, the numbers of the obtained transformants as well as the corresponding mutated sites, changes in amino acid sequence and changes in base sequence are given.

TABLE 150

| Number | Mutated site | Change in amino acid sequence | | Change in base sequence | |
|---|---|---|---|---|---|
| | | Before mutation | After mutation | Before mutation | After mutation |
| No. 96h | 218$^{th}$ position in β-subunit | Cys | Met | tgc | atg |
| No. 96i | 218$^{th}$ position in β-subunit | Cys | Ser | tgc | tcc |

Example 118

Comparison of Character Between Nitrile Hydratase Before Modification and Modified Enzyme after Modification (1)

In a 500 ml Erlenmeyer flask with baffles, 5 sets of a liquid LB medium of 100 ml each containing 40 μg/ml of ferric sulfate.heptahydrate and 10 μg/ml of cobalt chloride.hexahydrate were prepared and sterilized by autoclaving at 121° C. for 20 minutes. To each medium, ampicillin was added to a final concentration of 100 μg/ml.

Five types of transformants such as transformant No. 200 obtained in Example 84 and transformants No. 201 to 204 obtained in Example 88 were inoculated onto the above media such that one platinum loop of each of the transformant was inoculated on each of the five media. The cells were incubated therein at 37° C. for about 20 hours with stirring at 130 rpm. Each of the transformants were separated from the resulting culture by centrifugation (5,000 G×15 minutes).

Subsequently, the separated transformants were resuspended in 50 ml of physiological saline, and then subjected to another centrifugation (5,000 G×15 minutes), thereby each transformant being separated.

0.1 g of each of the transformants were suspended in 20 ml of an aqueous solution (pH 7.0) of 50 mM potassium phosphate, and then the suspensions were divided into 10 ml×2 sets. Thus, two suspensions per each tranformant, that is, 10 suspensions in total, were prepared. To one suspension of each transformant, 1 ml of acrylonitrile was added, and to the other suspension, methacrylonitrile was added. The suspensions were gently stirred at 30° C. for 10 minutes to react.

After completion of the reaction, an analysis of the reaction mixtures was carried out with HPLC, and it was found that each mixture contained a nitrile compound (acrylonitrile or methacrylonitrile), which was unreacted substrate, and an amide compound (acrylamide or methacrylamide), which was the corresponding product from the reaction. Further, the presence of a corresponding organic acid (acrylic acid or methacrylic acid) was not detected.

Comparison was made on the molar ratios for the respective transformants between the acrylamide which was produced from the reaction employing acrylonitrile as the substrate, and the methacrylamide which was produced from the reaction employing methacrylonitrile as the substrate. Differences as indicated in Table 151 below were observed. When a comparison is made in terms of acrylonitrile versus methacrylonitrile, from the viewpoint that methacrylonitirle is a bulkier nitrile compound, the results show that the obtained modified enzymes had increased facility in hydration of a bulkier substrate.

TABLE 151

| Number | 48$^{th}$ amino acid in β-subunit (base sequence) | Ratio of hydration activation (relative ratio) [case with methacrylonitrile as substrate] ÷ [case with acrylonitrile as substrate] |
| --- | --- | --- |
| No. 200 | Trp (tgg) | 0.41 (100%) |
| No. 201 | Tyr (tat) | 0.87 (211%) |
| No. 202 | Val (gtg) | 0.79 (192%) |
| No. 203 | Ala (gcg) | 0.67 (163%) |
| No. 204 | Gly (ggg) | 0.82 (198%) |

Example 119

Comparison of Character Between Nitrile Hydratase Before Modification and Modified Enzyme after Modification (2)

In a 500 ml Erlenmeyer flask with baffles, 56 sets of a liquid LB medium of 100 ml each containing 40 μg/ml of ferric sulfate.heptahydrate and 10 μg/ml of cobalt chloride.hexahydrate were prepared and sterilized by autoclaving at 121° C. for 20 minutes. To each medium, ampicillin was added to a final concentration of 100 μg/ml.

Fifty-six types of transformants such as a transformant No. 0 obtained by transforming HB101 with pPT-DB1 and the following transformants obtained in Examples 89 to 117: No. 40, No. 40e, No. 40f, No. 42, No. 42a, No. 43, No. 44, No. 45, No. 46, No. 47, No. 48, No. 49, No. 50, No. 51, No. 52, No. 54, No. 55, No. 56, No. 57, No. 58, No. 59, No. 60, No. 61, No. 62, No. 63, No. 64, No. 65, No. 66, No. 67, No. 68, No. 69, No. 70, No. 71, No. 72, No. 73, No. 74, No. 75, No. 76, No. 77, No. 78, No. 79, No. 80, No. 81, No. 82, No. 83, No. 84, No. 85, No. 87, No. 88, No. 89, No. 90, No. 91, No. 92, No. 93, No. 94 and No. 95, were inoculated onto the above media such that one platinum loop of each of the transformant was inoculated on each of the 57 media. The cells were incubated therein at 37° C. for about 20 hours with stirring at 130 rpm. Each of the transformants was separated from the resulting culture by centrifugation (5,000 G x 15 minutes). Subsequently, the separated transformants were resuspended in 50 ml of physiological saline, and then subjected to another centrifugation (5,000 G x 15 minutes), thereby each transformant being separated.

0.1 g of each of the transformants were suspended in 20 ml of an aqueous solution (pH 7.0) of 50 mM potassium phosphate, and then the suspensions were divided into 10 ml×2 sets. Thus, two suspensions per each tranformant, that is, 112 suspensions in total, were prepared. To one suspension of each transformant, 1 ml of acrylonitrile was added, and to the other suspension, methacrylonitrile was added. The suspensions were gently stirred at 20° C. for 10 minutes to react.

After completion of the reaction, an analysis of the reaction mixtures was carried out with HPLC, and it was found that each mixture contained a nitrile compound (acrylonitrile or methacrylonitrile), which was unreacted substrate, and an amide compound (acrylamide or methacrylamide), which was the corresponding product from the reaction. Further, the presence of a corresponding organic acid (acrylic acid or methacrylic acid) was not detected.

Comparison was made on the molar ratios for the respective transformants between the acrylamide which was produced from the reaction employing acrylonitrile as the substrate, and the methacrylamide which was produced from the reaction employing methacrylonitrile as the substrate. Thus, such diversity as indicated in Table 152, Table 153 and Table 154 could be observed. When acrylonitrile and methacrylonitrile are compared for their bulkiness, methacrylonitrile is the bulkier nitrile compound. These results show that modified enzymes with changed substrate specificity was obtained, as compared with nitrile hydratase before modification.

TABLE 152

| Number | Ratio of hydration activation (relative ratio) [case with methacrylonitrile as substrate] ÷ [case with acrylonitrile as substrate] | Ratio of hydration activation (relative ratio) [case with acrylonitrile as substrate] ÷ [case with methacrylonitrile as substrate] |
| --- | --- | --- |
| No. 0 | 0.189 (100%) | 5.29 (100%) |
| No. 40 | 0.219 (116%) | 4.55 (86%) |
| No. 40e | 0.211 (112%) | 4.71 (89%) |
| No. 40f | 0.206 (109%) | 4.87 (92%) |
| No. 42 | 0.200 (106%) | 4.97 (94%) |
| No. 42a | 0.202 (107%) | 4.92 (93%) |
| No. 43 | 0.185 (98%) | 5.40 (102%) |
| No. 44 | 0.185 (98%) | 5.40 (102%) |
| No. 45 | 0.187 (99%) | 5.34 (101%) |
| No. 46 | 0.185 (98%) | 5.40 (102%) |
| No. 47 | 0.181 (96%) | 5.50 (104%) |
| No. 48 | 0.187 (99%) | 5.34 (101%) |
| No. 49 | 0.208 (110%) | 4.81 (91%) |
| No. 50 | 0.198 (105%) | 5.03 (95%) |
| No. 51 | 0.187 (99%) | 5.34 (101%) |
| No. 52 | 0.202 (107%) | 4.92 (93%) |
| No. 54 | 0.153 (81%) | 6.51 (123%) |
| No. 55 | 0.159 (84%) | 6.30 (119%) |
| No. 56 | 0.204 (108%) | 4.92 (93%) |
| No. 57 | 0.168 (89%) | 5.92 (112%) |

TABLE 153

| Number | Ratio of hydration activation (relative ratio) [case with methacrylonitrile as substrate] ÷ [case with acrylonitrile as substrate] | Ratio of hydration activation (relative ratio) [case with acrylonitrile as substrate] ÷ [case with methacrylonitrile as substrate] |
|---|---|---|
| No. 58 | 0.159 (84%) | 6.30 (119%) |
| No. 59 | 0.183 (97%) | 5.45 (103%) |
| No. 60 | 0.160 (85%) | 6.24 (118%) |
| No. 61 | 0.195 (103%) | 5.13 (97%) |
| No. 62 | 0.210 (111%) | 4.76 (90%) |
| No. 63 | 0.198 (105%) | 5.03 (95%) |
| No. 64 | 0.155 (82%) | 6.45 (122%) |
| No. 65 | 0.206 (109%) | 4.87 (92%) |
| No. 66 | 0.180 (95%) | 5.55 (105%) |
| No. 67 | 0.172 (91%) | 5.82 (110%) |
| No. 68 | 0.399 (211%) | 2.49 (47%) |
| No. 69 | 0.259 (137%) | 3.86 (73%) |
| No. 70 | 0.212 (112%) | 4.71 (89%) |
| No. 71 | 0.223 (118%) | 4.50 (85%) |
| No. 72 | 0.206 (109%) | 4.87 (92%) |
| No. 73 | 0.229 (121%) | 4.39 (83%) |
| No. 74 | 0.233 (123%) | 4.28 (81%) |
| No. 75 | 0.204 (108%) | 4.92 (93%) |
| No. 76 | 0.191 (101%) | 5.24 (99%) |
| No. 77 | 0.271 (142%) | 3.70 (70%) |

TABLE 154

| Number | Ratio of hydration activation (relative ratio) [case with methacrylonitrile as substrate] ÷ [case with acrylonitrile as substrate] | Ratio of hydration activation (relative ratio) [case with acrylonitrile as substrate] ÷ [case with methacrylonitrile as substrate] |
|---|---|---|
| No. 78 | 0.268 (137%) | 3.86 (73%) |
| No. 79 | 0.170 (90%) | 5.87 (111%) |
| No. 80 | 0.183 (97%) | 5.45 (103%) |
| No. 81 | 0.180 (95%) | 5.56 (105%) |
| No. 82 | 0.164 (87%) | 6.08 (115%) |
| No. 83 | 0.174 (92%) | 5.77 (109%) |
| No. 84 | 0.208 (110%) | 4.81 (91%) |
| No. 85 | 0.164 (87%) | 6.08 (115%) |
| No. 87 | 0.176 (93%) | 5.71 (108%) |
| No. 88 | 0.166 (88%) | 6.03 (114%) |
| No. 89 | 0.191 (101%) | 5.24 (99%) |
| No. 90 | 0.197 (104%) | 5.08 (96%) |
| No. 91 | 0.187 (99%) | 5.34 (101%) |
| No. 92 | 0.185 (98%) | 5.40 (102%) |
| No. 93 | 0.187 (99%) | 5.34 (101%) |
| No. 94 | 0.193 (102%) | 5.18 (98%) |
| No. 95 | 0.187 (99%) | 5.34 (101%) |

INDUSTRIAL APPLICABILITY

The present invention is useful in the art of material production using biological catalyst. An example thereof may include the case of material production by conversion of a nitrile compound to a corresponding amide compound by means of hydration using an enzyme called nitrile hydratase or an organism expressing the enzyme activity as the biological catalyst.

---

The invention claimed is:

1. An isolated nitrile hydratase comprising an α-subunit and a β-subunit, wherein:
    (a) the α-subunit comprises the polypeptide of SEQ ID NO: 1, except that the amino acid sequence of the polypeptide of SEQ ID NO: 1 is substituted at positions:
    36 to Met,
    71 to His,
    148 to Asp,
    204 to Arg, Lys, Trp or Thr,
    148 and 204 to Asp and Arg respectively,
    36, 148 and 204 to Met, Asp and Arg respectively,
    36 and 126 to Met and Tyr respectively,
    6, 36, and 126 to Met, Thr and Tyr respectively, or
    19, 71, and 126 to His, Val and Tyr respectively; and
    (b) the β-subunit comprises the polypeptide of SEQ ID NO: 2.

2. The nitrile hydratase according to claim 1, wherein the β-subunit consists of the polypeptide of SEQ ID NO: 2.

3. An isolated nitrile hydratase comprising an α-subunit and a β-subunit, wherein:
    (a)(i) the α-subunit comprises the polypeptide of SEQ ID NO: 1, except that the amino acid sequence of the polypeptide of SEQ ID NO: 1 is substituted at positions 36, 148 and 204 of SEQ ID NO: 1 to Met, Asp and Arg respectively, and (ii) the β-subunit comprises the polypeptide of SEQ ID NO: 2, except that the amino acid sequence of the polypeptide of SEQ ID NO: 2 is substituted at positions 41, 51 and 108 of SEQ ID NO: 2 to Ile, Val, and Asp respectively;

(b)(i) the α-subunit comprises the polypeptide of SEQ ID NO: 1, except that the amino acid sequence of the polypeptide of SEQ ID NO: 1 is substituted at positions 6, 36 and 126 of SEQ ID NO: 1 to Thr, Met and Tyr respectively, and (ii) the β-subunit comprises the polypeptide of SEQ ID NO: 2, except that the amino acid sequence of the polypeptide of SEQ ID NO: 2 is substituted at positions 10, 118, and 200 of SEQ ID NO: 2 to Asp, Val and Glu respectively;

(c)(i) the α-subunit comprises the polypeptide of SEQ ID NO: 1, except that the amino acid sequence of the polypeptide of SEQ ID NO: 1 is substituted at positions 19, 71 and 126 of SEQ ID NO: 1 to Val, His and Tyr respectively, and (ii) the β-subunit comprises the polypeptide of SEQ ID NO: 2, except that the amino acid sequence of the polypeptide of SEQ ID NO: 2 is substituted at positions 37, 108, and 200 of SEQ ID NO: 2 to Leu, Asp, and Glu respectively;

(d)(i) the α-subunit comprises the polypeptide of SEQ ID NO: 1, except that the amino acid sequence of the polypeptide of SEQ ID NO: 1 is substituted at positions 19, 71 and 126 of SEQ ID NO: 1 to Val, His and Tyr respectively, and (ii) the β-subunit comprises the polypeptide of SEQ ID NO: 2, except that the amino acid sequence of the polypeptide of SEQ ID NO: 2 is substituted at positions 37, 108, and 200 of SEQ ID NO: 2 to Val, Asp, and Glu respectively; or (e)(i) the α-subunit comprises the polypeptide of SEQ ID NO: 1, except that the amino acid sequence of the polypeptide of SEQ ID NO: 1 is substituted at positions 148 and 204 of SEQ ID NO: 1 to Asp and Arg respectively, and (ii) the β-subunit comprises the polypeptide of SEQ ID NO: 2, except that the amino acid sequence of the polypeptide of SEQ ID NO: 2 is substituted at positions 108, and 200 of SEQ ID NO: 2 to Asp, and Glu respectively.

4. An isolated nitrile hydratase comprising an α-subunit and a β-subunit, wherein:
(a) the α-subunit comprises the polypeptide of SEQ ID NO: 1; and
(b) the β-subunit comprises the polypeptide of SEQ ID NO: 2, except that the amino acid sequence of the polypeptide of SEQ ID NO: 2 is substituted at positions;
10 to Asp, Glu, Trp, Gly, Tyr or Cys,
32 to Gly,
37 to Thr, Ala, Leu, Ile or Val,
41 to Glu, Thr, Ala, Leu, Ile, or Val,
46 to Gly, Tyr, Leu, Lys or Asp,
48 to Gly, Ala, Val, Ser, Thr or Arg,
51 to Ala or Val,
72 to Phe,
118 to Ala, Leu, Ile or Val,
127 to Ala, Val or Ser,
146 to Gly,
160 to Leu or Trp,
186 to Glu, Asp, Lys, Arg, Asn, Ser or Gly
217 to Gly,
160 and 186 to Trp and Arg respectively,
127, 160 and 186 to Ser, Trp and Arg respectively,
51 and 108 to Val and Asp respectively,
118 and 200 to Val and Glu respectively,
10, 118 and 200 to Asp, Val and Glu respectively,
37, 108 and 200 to Leu, Asp and Glu respectively,
37, 108 and 200 to Val, Asp and Glu respectively,
41, 51 and 109 to Ile, Val and Asp respectively,
46, 108 and 212 to Lys, Arg and Tyr respectively, or
48, 108 and 212 to Val, Arg and Tyr respectively.

5. The nitrile hydratase according to claim 4, wherein the α-subunit consists of the polypeptide of SEQ ID NO: 1.

6. An isolated nitrile hydratase comprising an α-subunit and a β-subunit, wherein:
(a)(i) the α-subunit comprises the polypeptide of SEQ ID NO: 1, except that the amino acid sequence of the polypeptide of SEQ ID NO: 1 is substituted at positions 6, 19 and 126 of SEQ ID NO: 1 to Thr, Val and Tyr respectively, and (ii) the β-subunit comprises the polypeptide of SEQ ID NO: 2, except that the amino acid sequence of the polypeptide of SEQ ID NO: 2 is substituted at positions 46, 108 and 212 of SEQ ID NO: 2 to Lys, Arg and Tyr respectively;

(b)(i) the α-subunit comprises the polypeptide of SEQ ID NO: 1, except that the amino acid sequence of the polypeptide of SEQ ID NO: 1 is substituted at positions 6, 19 and 126 of SEQ ID NO: 1 to Thr, Val and Tyr respectively, and (ii) the β-subunit comprises the polypeptide of SEQ ID NO: 2, except that the amino acid sequence of the polypeptide of SEQ ID NO: 2 is substituted at positions 48, 108 and 212 of SEQ ID NO: 2 to Val, Arg and Tyr respectively, or (c)(i) the α-subunit comprises the polypeptide of SEQ ID NO: 1, except that the amino acid sequence of the polypeptide of SEQ ID NO: 1 is substituted at positions 6, 19 and 126 of SEQ ID NO: 1 to Ala, Val and Tyr respectively, and (ii) the β-subunit comprises the polypeptide of SEQ ID NO: 2, except that the amino acid sequence of the polypeptide of SEQ ID NO: 2 is substituted at positions 127, 160 and 186 of SEQ ID NO: 2 to Ser, Trp and Arg respectively.

7. An isolated host cell comprising the nitrile hydratase of claim 1.

8. An isolated host cell comprising the nitrile hydratase of claim 4.

9. An isolated host cell comprising the nitrile hydratase of claim 6.

10. An isolated host cell comprising the nitrile hydratase of claim 3.

11. An isolated nitrile hydratase comprising an α-subunit and a β-subunit, wherein:
(a) the α-subunit comprises the polypeptide of SEQ ID NO: 1, except that the amino acid sequence of the polypeptide of SEQ ID NO: 1 is substituted at one or more positions selected from the group consisting of positions 36, 71, 148, and 204 by another amino acid; and
(b) the β-subunit comprises the polypeptide of SEQ ID NO: 2, except that the amino acid sequence of the polypeptide of SEQ ID NO: 2 is substituted at one or more positions selected from the group consisting of positions 10, 32, 37, 41, 46, 48, 51, 72, 118, 127, 146, 160, 186, and 217 by another amino acid.

12. An isolated host cell comprising the nitrile hydratase of claim 11.

* * * * *